US011309497B2

(12) United States Patent
Parham et al.

(10) Patent No.: US 11,309,497 B2
(45) Date of Patent: Apr. 19, 2022

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt Am Main (DE); Tobias Grossmann, Darmstadt (DE); Thomas Eberle, Landau (DE); Anja Jatsch, Frankfurt Am Main (DE); Jonas Valentin Kroeber, Frankfurt Am Main (DE); Lars Dobelmann-Mara, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 22 days.

(21) Appl. No.: 15/329,099

(22) PCT Filed: Jul. 3, 2015

(86) PCT No.: PCT/EP2015/001353
§ 371 (c)(1),
(2) Date: Jan. 25, 2017

(87) PCT Pub. No.: WO2016/015810
PCT Pub. Date: Feb. 4, 2016

(65) Prior Publication Data
US 2017/0207399 A1 Jul. 20, 2017

(30) Foreign Application Priority Data
Jul. 29, 2014 (EP) .................................... 14002642

(51) Int. Cl.
| | | |
|---|---|---|
| H01L 51/00 | (2006.01) | |
| C09K 11/06 | (2006.01) | |
| C07D 409/14 | (2006.01) | |
| C07D 405/14 | (2006.01) | |
| C07D 405/04 | (2006.01) | |
| C07D 491/048 | (2006.01) | |
| C07D 471/04 | (2006.01) | |
| C07D 495/04 | (2006.01) | |
| C07D 471/14 | (2006.01) | |
| C09K 11/02 | (2006.01) | |
| C07D 487/04 | (2006.01) | |
| H05B 33/20 | (2006.01) | |
| C07D 409/04 | (2006.01) | |
| H01L 51/50 | (2006.01) | |

(52) U.S. Cl.
CPC ........ H01L 51/0072 (2013.01); C07D 405/04 (2013.01); C07D 405/14 (2013.01); C07D 409/04 (2013.01); C07D 409/14 (2013.01); C07D 471/04 (2013.01); C07D 471/14 (2013.01); C07D 487/04 (2013.01); C07D 495/04 (2013.01); C07D 491/048 (2013.01); C09K 11/025 (2013.01); C09K 11/06 (2013.01); H01L 51/006 (2013.01); H01L 51/0061 (2013.01); H01L 51/0067 (2013.01); H01L 51/0071 (2013.01); H01L 51/0073 (2013.01); H01L 51/0074 (2013.01); H05B 33/20 (2013.01); C09K 2211/1007 (2013.01); C09K 2211/1059 (2013.01); C09K 2211/185 (2013.01); H01L 51/0052 (2013.01); H01L 51/0056 (2013.01); H01L 51/0058 (2013.01); H01L 51/5012 (2013.01); H01L 51/5016 (2013.01); H01L 51/5028 (2013.01); H01L 51/5056 (2013.01); H01L 51/5072 (2013.01); H01L 51/5096 (2013.01)

(58) Field of Classification Search
None
See application file for complete search history.

(56) References Cited

U.S. PATENT DOCUMENTS

| | | | |
|---|---|---|---|
| 9,136,484 B2 | 9/2015 | Kim et al. | |
| 9,257,651 B2 | 2/2016 | Konuma et al. | |
| 9,614,166 B2 | 4/2017 | Kai et al. | |
| 2006/0125380 A1* | 6/2006 | Nagara ............... | H01L 51/5016 313/504 |
| 2011/0233530 A1* | 9/2011 | Nowatari et al. ............... | 257/40 |
| 2014/0158992 A1 | 6/2014 | Xia et al. | |
| 2014/0225046 A1 | 8/2014 | Jatsch et al. | |
| 2014/0326987 A1 | 11/2014 | Park et al. | |
| 2017/0186965 A1 | 6/2017 | Parham et al. | |

FOREIGN PATENT DOCUMENTS

| | | | |
|---|---|---|---|
| CN | 103534251 A | | 1/2014 |
| JP | 2009021336 A | * | 1/2009 |
| JP | 2011084531 A | | 4/2011 |
| JP | 201249518 A | | 3/2012 |
| JP | 201360396 A | | 4/2013 |
| JP | 2017514878 A | | 6/2017 |
| WO | WO-2011158592 A1 | | 12/2011 |
| WO | WO-2013041176 A1 | | 3/2013 |
| WO | WO-2013081315 A1 | | 6/2013 |

(Continued)

OTHER PUBLICATIONS

Machine English translation of Katakura et al. (JP 2011-084531 A). Jun. 29, 2018.*
Machine English translation of Yasukawa et al. (JP 2009-021336 A). Jan. 26, 2021.*
International Search Report for PCT/EP2015/001353 dated Oct. 6, 2015.
Written Opinion of the International Searching Authority for PCT/EP2015/001353 dated Oct. 6, 2015.

*Primary Examiner* — Jay Yang
(74) *Attorney, Agent, or Firm* — Faegre Drinker Biddle & Reath LLP

(57) ABSTRACT

The present invention describes dibenzofuran and dibenzothiophene derivatives, in particular for use as triplet matrix materials in organic electroluminescent devices. The invention furthermore relates to a process for the preparation of the compounds according to the invention and to electronic devices comprising same.

9 Claims, No Drawings

(56) References Cited

FOREIGN PATENT DOCUMENTS

| WO | WO-2013102992 A1 | | 7/2013 |
|----|------------------|---|--------|
| WO | WO-2014013936 A1 | | 1/2014 |
| WO | WO-2014/042420 A1 | * | 3/2014 |
| WO | WO-2014042420 A1 | | 3/2014 |

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/001353, filed Jul. 3, 2015, which claims benefit of European Application No. 14002642.8, filed Jul. 29, 2014, both of which are incorporated herein by reference in their entirety.

The present invention describes dibenzofuran and dibenzothiophene derivatives, in particular for use as triplet matrix materials in organic electroluminescent devices. The invention furthermore relates to a process for the preparation of the compounds according to the invention and to electronic devices comprising these compounds.

BACKGROUND OF THE INVENTION

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed are frequently organometallic complexes which exhibit phosphorescence instead of fluorescence. For quantum-mechanical reasons, an up to four-fold increase in energy and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence). The properties of phosphorescent OLEDs are not determined only by the triplet emitters employed. In particular, the other materials used, such as, for example, matrix materials, are also of particular importance here. Improvements in these materials may thus also result in significant improvements in the OLED properties.

In accordance with the prior art, inter alia carbazole derivatives (for example in accordance with WO 2014/015931), indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine, are used as matrix materials for phosphorescent emitters. Furthermore, bis-dibenzofuran derivatives (for example in accordance with EP 2301926), for example, are used as matrix materials for phosphorescent emitters. WO 2013/077352 discloses triazine derivatives in which the triazine group is bonded to a dibenzofuran group via a divalent arylene group. These compounds are described as hole-blocking materials. Use of these materials as host for phosphorescent emitters is not disclosed.

In general, there is still a need for improvement in the case of materials for use as matrix materials, in particular with respect to the lifetime, but also with respect to the efficiency and the operating voltage of the device.

BRIEF SUMMARY OF THE INVENTION

The object of the present invention is the provision of compounds which are suitable for use in a phosphorescent or fluorescent OLED, in particular as matrix material. In particular, it is an object of the present invention to provide matrix materials which are suitable for red-, yellow- and green-phosphorescent OLEDs and optionally also for blue-phosphorescent OLEDs and which result in a long lifetime, good efficiency and a low operating voltage.

Surprisingly, it has been found that electroluminescent devices which comprise compounds of the following formula (1) have improvements over the prior art, in particular on use as matrix material for phosphorescent dopants.

DETAILED DESCRIPTION OF THE INVENTION

The present invention therefore relates to a compound of the following formula (1),

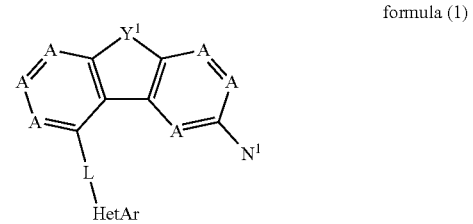

formula (1)

where the following applies to the symbols used:

A is on each occurrence, identically or differently, $CR^1$ or N, where a maximum of two groups A per ring stand for N;

$Y^1$ is O or S;

L is a single bond or an aromatic or heteroaromatic ring system having 5 to 30 aromatic ring atoms, which may be substituted by one or more radicals $R^1$;

HetAr is a group of the following formula (2), (3) or (4),

formula (2)

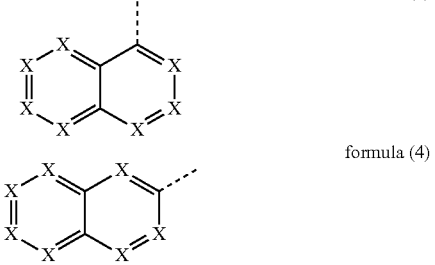

formula (3)

formula (4)

where the dashed bond represents the linking of this group;

X is on each occurrence, identically or differently, $CR^2$ or N, with the proviso that at least one symbol X stands for N;

$N^1$ is a group of the following formula (5) or (6),

formula (5)

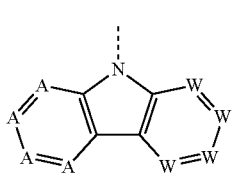

formula (6)

where the dashed bond represents the linking of this group, and A in formula (6) has the meanings given above;

$Ar^1$ is on each occurrence, identically or differently, an aromatic or heteroaromatic ring system having 5 to 30 aromatic ring atoms, which may be substituted by one or more radicals $R^3$;

W is on each occurrence, identically or differently, $CR^1$ or N, where a maximum of two groups W stand for N, or precisely two adjacent groups W together stand for a group of the following formula (7) or (8), and the remaining groups W stand, identically or differently on each occurrence, for $CR^1$ or N,

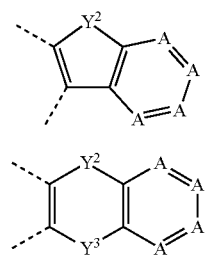

formula (7)

formula (8)

where the dashed bonds indicate the linking of this group, and A has the meanings given above;

$Y^2$, $Y^3$ are, identically or differently on each occurrence, O, $NR^4$, S, $C(R^4)_2$, $Si(R^4)_2$, $BR^4$ or C=O, where the radical $R^4$ which is bonded to N is not equal to H;

$R^1$, $R^2$, $R^3$, $R^4$ are selected on each occurrence, identically or differently, from the group consisting of H, D, F, Cl, Br, I, CN, $NO_2$, $N(Ar^2)_2$, $N(R^5)_2$, C(=O)$Ar^2$, C(=O)$R^5$, P(=O)$(Ar^2)_2$, P($Ar^2)_2$, B($Ar^2)_2$, Si($Ar^2)_3$, Si($R^5)_3$, a straight-chain alkyl, alkoxy or thioalkyl group having 1 to 20 C atoms or a branched or cyclic alkyl, alkoxy or thioalkyl group having 3 to 20 C atoms or an alkenyl group having 2 to 20 C atoms, each of which may be substituted by one or more radicals $R^5$, where one or more non-adjacent $CH_2$ groups may be replaced by $R^5C=CR^5$, $Si(R^5)_2$, C=O, C=$NR^5$, P(=O)($R^5$), SO, $SO_2$, $NR^5$, O, S or $CONR^5$ and where one or more H atoms may be replaced by D, F, Cl, Br, I, CN or $NO_2$, an aromatic or heteroaromatic ring system having 5 to 40 aromatic ring atoms, which may in each case be substituted by one or more radicals $R^5$, an aryloxy or heteroaryloxy group having 5 to 40 aromatic ring atoms, which may be substituted by one or more radicals $R^5$, or an aralkyl or heteroaralkyl group having 5 to 40 aromatic ring atoms, which may be substituted by one or more radicals $R^5$; two adjacent substituents $R^1$ or two adjacent substituents $R^3$ here may optionally form an aliphatic ring system, which may be substituted by one or more radicals $R^5$, and two adjacent substituents $R^4$ may form an aliphatic or aromatic ring system, which may be substituted by one or more radicals $R^5$;

$Ar^2$ is on each occurrence, identically or differently, an aromatic or heteroaromatic ring system having 5 to 30 aromatic ring atoms, which may be substituted by one or more non-aromatic radicals $R^5$; two radicals $Ar^2$ which are bonded to the same N atom, P atom or B atom here may also be bridged to one another by a single bond or a bridge selected from $N(R^5)$, $C(R^5)_2$, O or S;

$R^5$ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^5$ here may form an aliphatic ring system with one another.

Adjacent substituents in the sense of the present invention are substituents which are bonded to carbon atoms which are linked directly to one another or which are bonded to the same carbon atom.

The formulation that two or more radicals may form a ring with one another is, for the purposes of the present application, intended to be taken to mean, inter alia, that the two radicals are linked to one another by a chemical bond. This is illustrated by the following scheme:

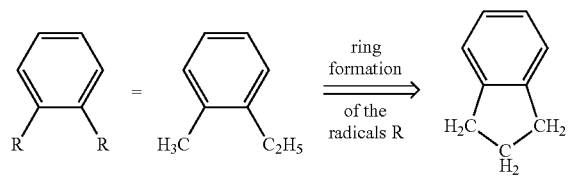

Furthermore, however, the above-mentioned formulation is also intended to be taken to mean that, in the case where one of the two radicals represents hydrogen, the second radical is bonded at the position at which the hydrogen atom was bonded, with formation of a ring.

A condensed aryl group in the sense of the present invention is a group in which two or more aromatic groups are condensed, i.e. annellated, onto one another via a common edge, such as, for example, in naphthalene. By contrast, for example, fluorene is not a condensed aryl group in the sense of the present invention, since the two aromatic groups in fluorene do not have a common edge.

An aromatic ring system in the sense of this invention contains 6 to 40 C atoms in the ring system. An aromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as fluorene, 9,9'-spirobifluorene, 9,9-diarylfluorene, triarylamine, etc., are also intended to be taken to be aromatic ring systems in the sense of this invention, as are systems in which two or more aryl groups are connected, for example, by a short alkyl group. Furthermore, aromatic rings linked to one another by a single bond, i.e. oligoarylenes or oligoheteroarylenes, such as, for example, biphenyl, terphenyl or quaterphenyl, are referred to as aromatic ring systems in the sense of this application.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethyhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-40 aromatic ring atoms is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

In a preferred embodiment of the invention, a maximum of one group A per ring stands for N and the other groups A stand for $CR^1$. A particularly preferably stands for $CR^1$, so that the compound of the formula (1) is a compound of the following formula (1a),

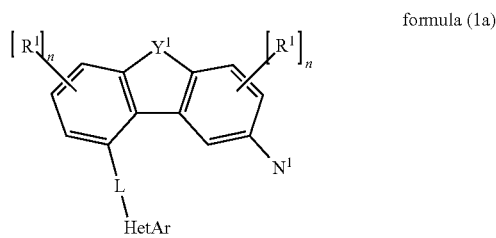

formula (1a)

where the symbols used have the meanings given above and n stands, identically or differently on each occurrence, for 0, 1, 2 or 3.

In a preferred embodiment of the invention, the index n in formula (1a) is, identically or differently on each occurrence, 0, 1 or 2, particularly preferably, 0 or 1 and very particularly preferably equal to 0.

Preferred embodiments of the formula (1a) are the compounds of the following formulae (1b) to (1f),

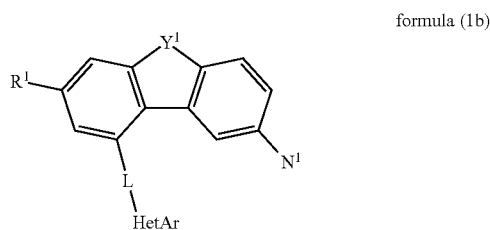

formula (1b)

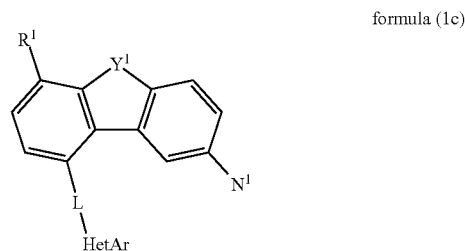

formula (1c)

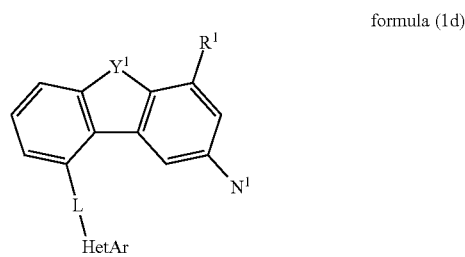

formula (1d)

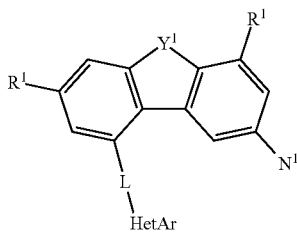

formula (1e)

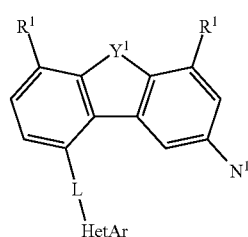

formula (1f)

where the symbols used have the meanings given above.
A particularly preferred embodiment is the compound of the following formula (1g),

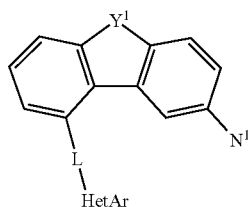

formula (1g)

where the symbols used have the meanings given above.
Preferred embodiments of the group HetAr are described below.
Preferred embodiments of the groups of the formulae (2), (3) and (4) are the groups of the following formulae (2-1) to (2-10), (3-1) and (4-1),

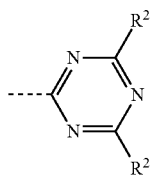

formula (2-1)

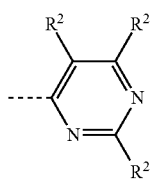

formula (2-2)

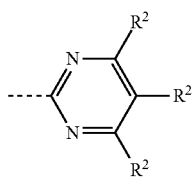

formula (2-3)

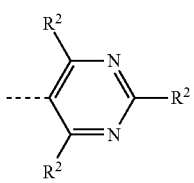

formula (2-4)

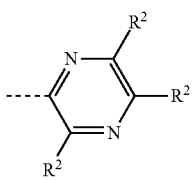

formula (2-5)

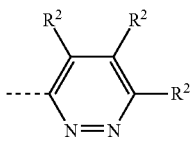

formula (2-6)

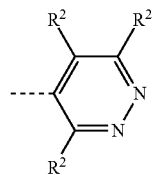

formula (2-7)

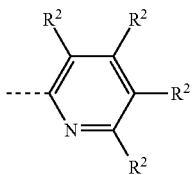

formula (2-8)

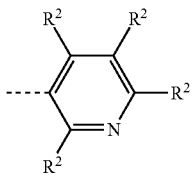

formula (2-9)

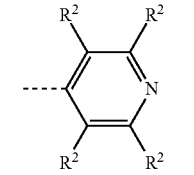

formula (2-10)

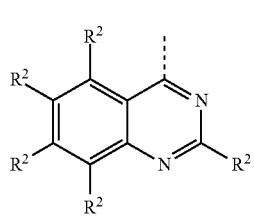

formula (3-1)

formula (4-1)

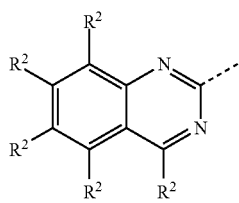

where the dashed bond represents the linking of these groups and $R^2$ has the meanings given above.

Preference is given to the groups of the formulae (2-1) to (2-3) and particular preference is given to the group of the formula (2-1).

Preferred embodiments of the above-mentioned groups are the groups of the following formulae (2-1a) to (4-1a), formula (2-1a)

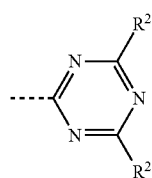

formula (2-2a)

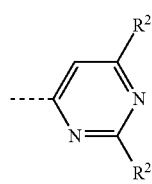

formula (2-3a)

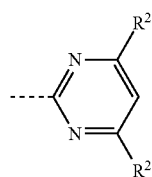

formula (2-4a)

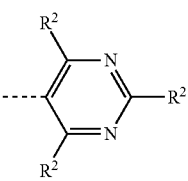

formula (2-5a)

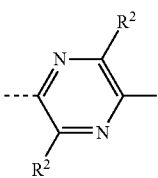

formula (2-6a)

formula (2-7a)

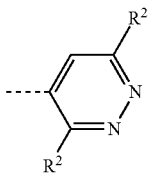

formula (2-8a)

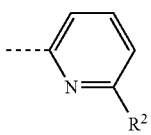

formula (2-9a)

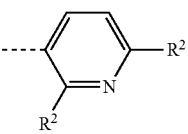

formula (2-10a)

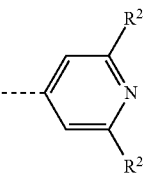

formula (3-1a)

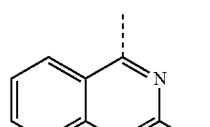

formula (4-1a)

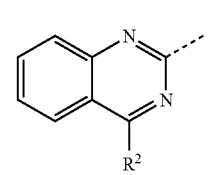

where the dashed bond represents the linking of these groups and $R^2$ represents a substituent in accordance with the definition given above other than hydrogen.

The substituent $R^2$ on the group HetAr is preferably, identically or differently on each occurrence, H or an aromatic or heteroaromatic ring system having 6 to 24 aromatic ring atoms, which may be substituted by one or more radicals $R^5$. $R^2$ in the groups of the formulae (2-1a) to (4-1a) here is not equal to hydrogen. The aromatic or heteroaromatic ring system preferably has 6 to 18 aromatic ring atoms. It is particularly preferably an aromatic ring system having 6 to 12 aromatic ring atoms or a heteroaromatic ring system having 6 to 13 aromatic ring atoms, each of which may be substituted by one or more radicals $R^5$, but is preferably unsubstituted. Examples of suitable groups $R^2$ are selected from the group consisting of phenyl, biphenyl, in particular ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^5$, but is preferably unsubstituted.

Examples of suitable groups R² are the structures R²-1 to R²-18 shown below,
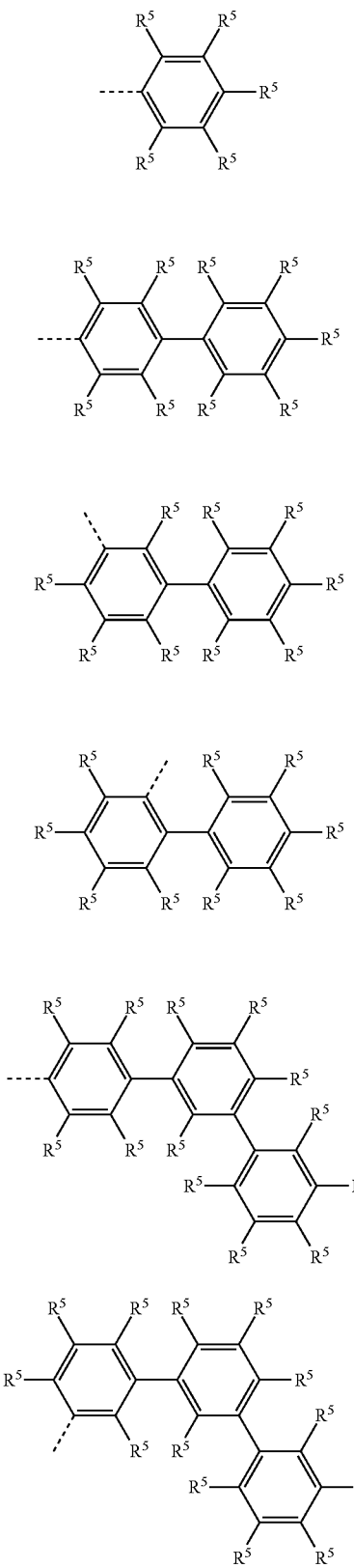
R²-1
R²-2
R²-3
R²-4
R²-5
R²-6
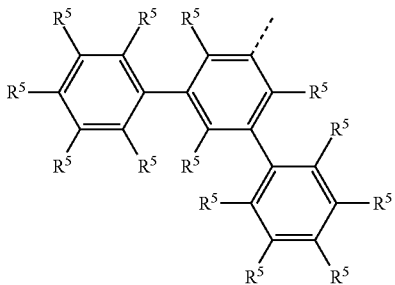
R²-7
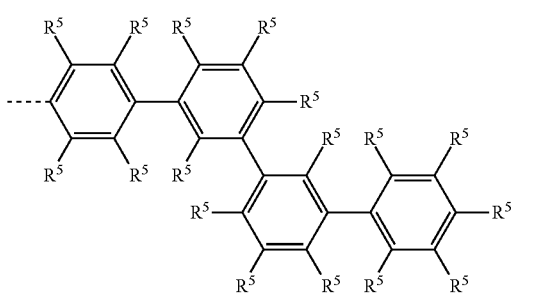
R²-8
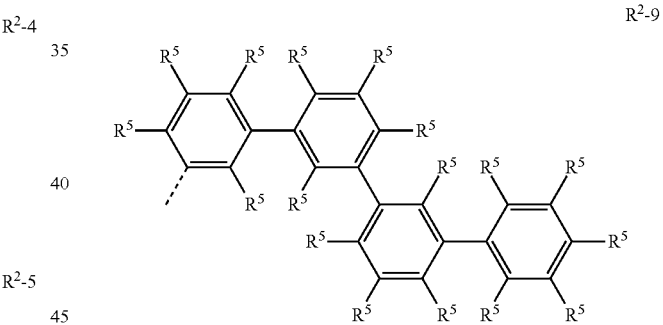
R²-9
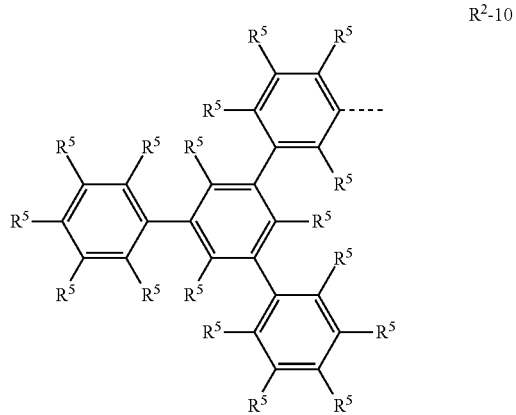
R²-10

-continued

R²-11
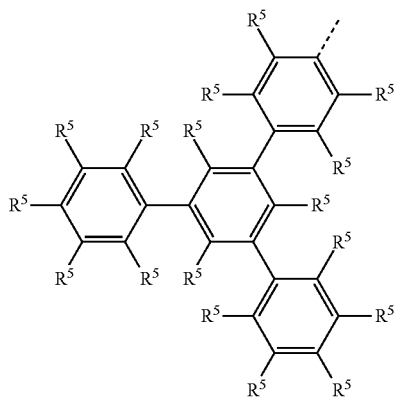

R²-12
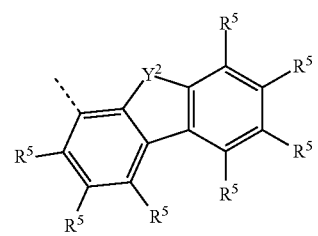

R²-13
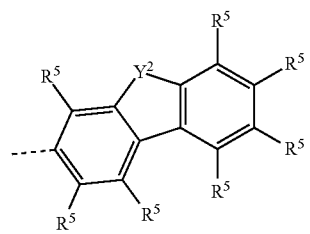

R²-14
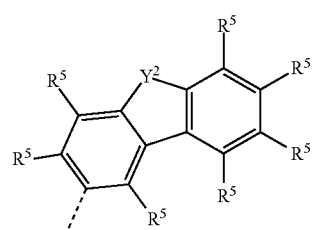

R²-15
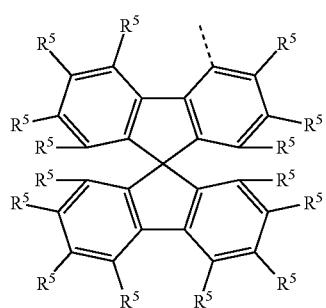

-continued

R²-16
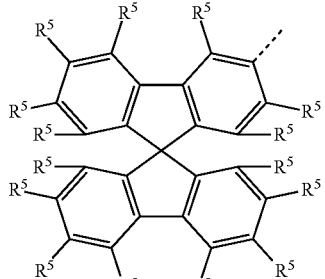

R²-17
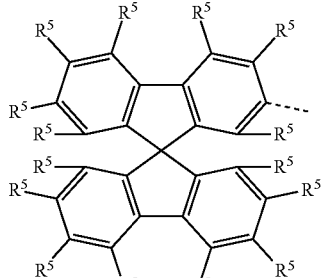

R²-18
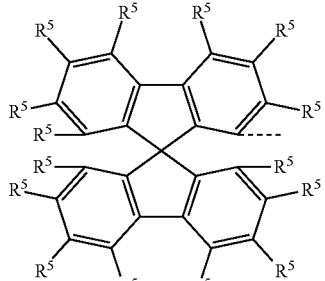

where $Y^2$ and $R^5$ have the meanings given above, and the dashed bond represents the bond to the heteroaryl group.

Preferred embodiments of the group $N^1$ are shown below. As described above, the group $N^1$ stands for a group of the formula (5) or (6).

In a preferred embodiment of the invention, the group $Ar^1$ in the group of the formula (5) stands, identically or differently on each occurrence, for an aromatic or heteroaromatic ring system having 6 to 24 aromatic ring atoms, preferably having 6 to 18 aromatic ring atoms, particularly preferably for an aromatic ring system having 6 to 12 aromatic ring atoms or a heteroaromatic ring system having 6 to 13 aromatic ring atoms, each of which may be substituted by one or more radicals $R^3$, but is preferably unsubstituted. Examples of suitable groups $Ar^1$ are selected from the group consisting of phenyl, biphenyl, in particular ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^3$, but is preferably unsubstituted.

Particularly preferred groups $Ar^1$ are the groups of the following formulae ($Ar^1$-1) to ($Ar^1$-20),

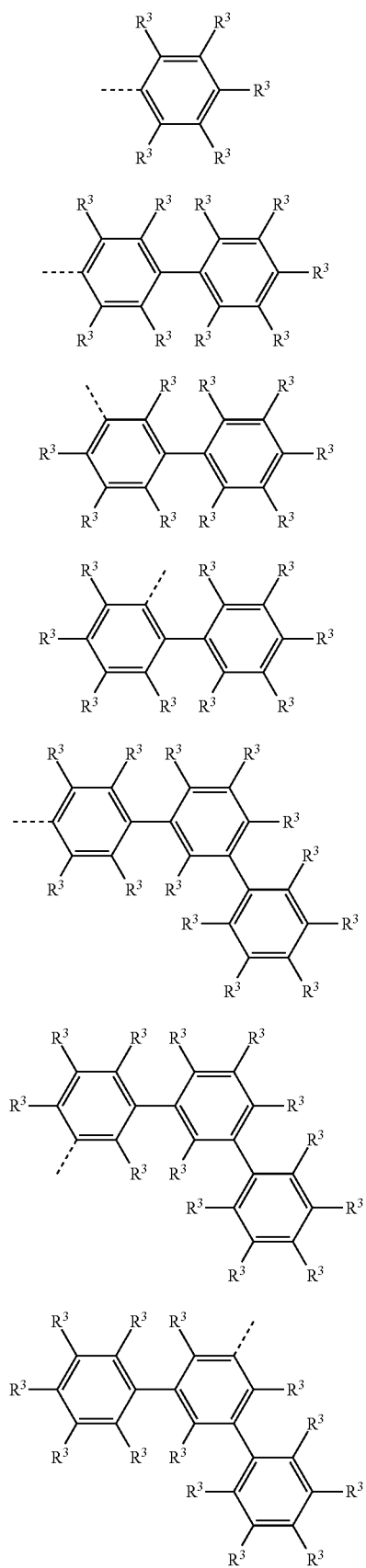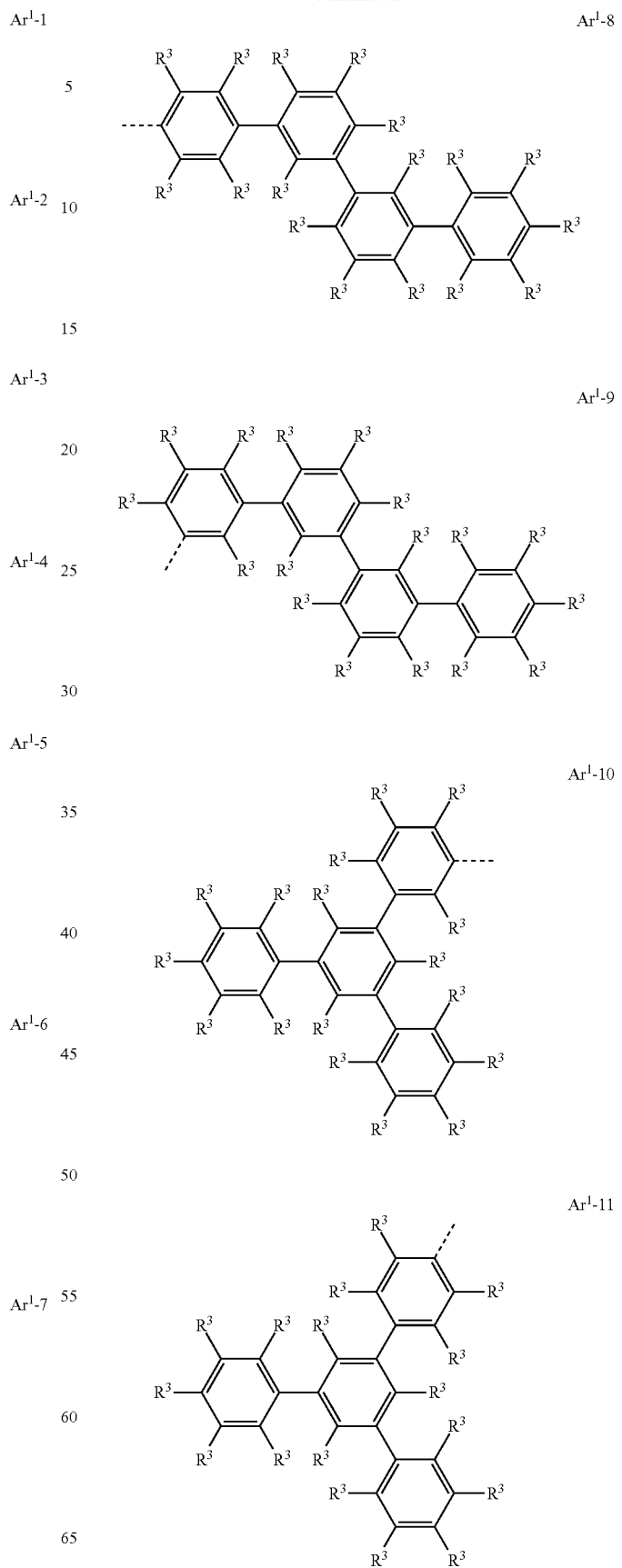

Ar¹-12
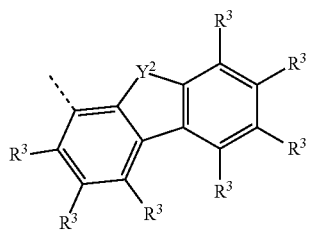

Ar¹-13
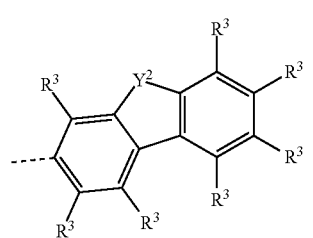

Ar¹-14
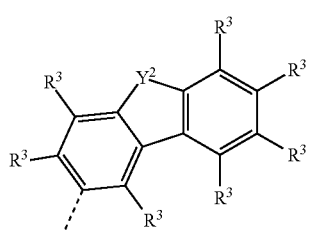

Ar¹-15
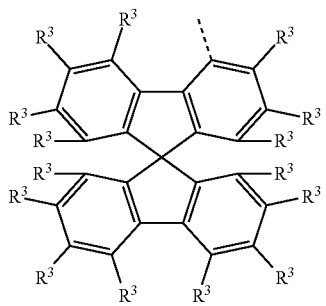

Ar¹-16
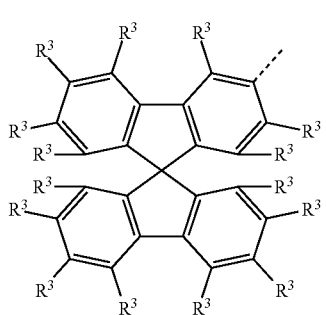

Ar¹-17
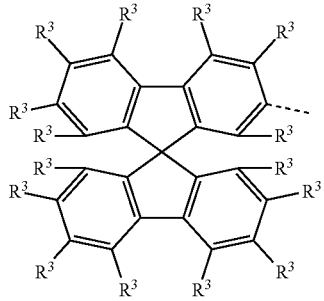

Ar¹-18
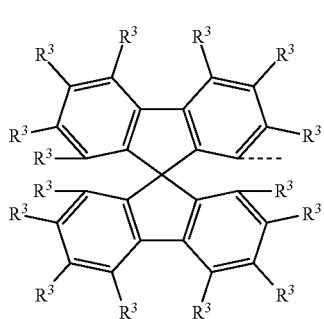

Ar¹-19
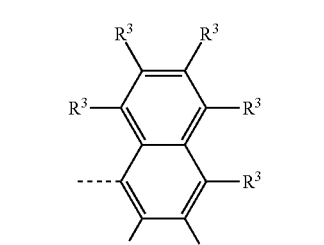

Ar¹-20
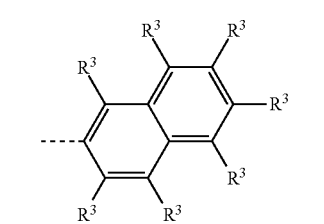

where $Y^2$ and $R^3$ have the meanings given above, and the dashed bond represents the bond to the nitrogen in formula (5).

In a preferred embodiment of the invention, $R^3$ stands, identically or differently on each occurrence, for H, an alkyl group having 1 to 4 C atoms or an aromatic or heteroaromatic ring system having 5 to 14 aromatic ring atoms. $R^3$ particularly preferably stands, identically or differently on each occurrence, for H or an alkyl group having 1 to 4 C atoms.

In the group of the formula (6), it is preferred if a maximum of one group A stands for N and the other groups A stand for $CR^1$. Particularly preferably, all groups A in formula (6) stand for $CR^1$. Particularly preferred groups of the formula (6) are thus the groups of the following formulae (6-1) and (6-2), formula (6-1)

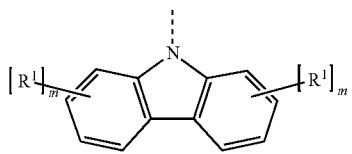

formula (6-2)

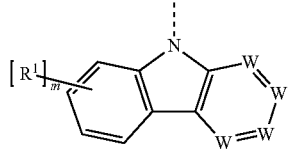

where R¹ has the meanings given above and furthermore:
two adjacent groups W together stand for a group of the following formula (7a) or (8a) and the other two groups W stand for CR¹ and preferably for CH, formula (7a)

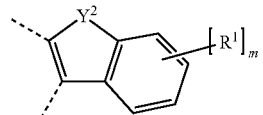

formula (8a)

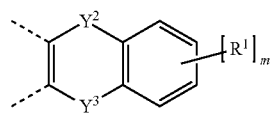

where $Y^2$, $Y^3$ and $R^1$ have the meanings given above;

m is, identically or differently on each occurrence, 0, 1, 2, 3 or 4.

In a preferred embodiment of the invention, the index m stands for 0, 1, 2 or 3, particularly preferably for 0, 1 or 2 and very particularly preferably for 0 or 1.

Preferred embodiments of the group of the formula (6-1) are the groups of the following formulae (6-1a) to (6-1f), formula (6-1a)

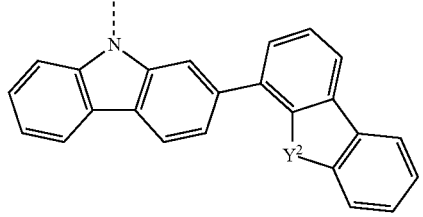

formula (6-1b)

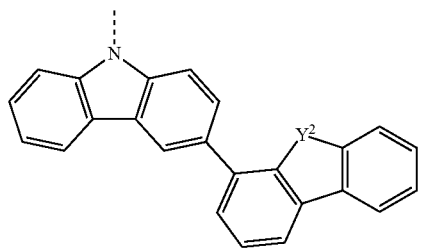

formula (6-1c)

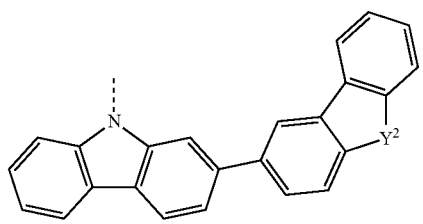

formula (6-1d)

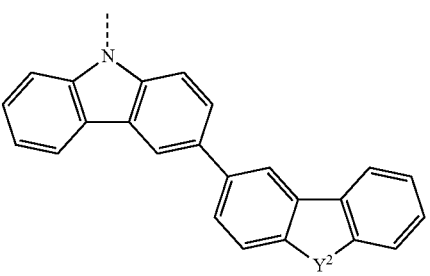

formula (6-1e)

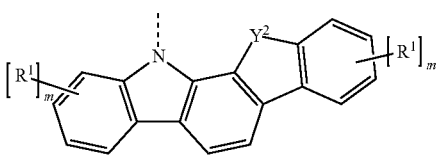

formula (6-1f)

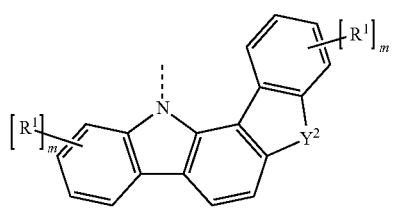

where $Y^2$ has the meanings given above and preferably stands for $NR^4$, O or S.

Preferred embodiments of the group of the formula (6-2) are the groups of the following formulae (6-2a) to (6-2f), formula (6-2a)

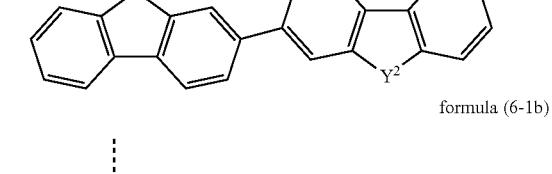

formula (6-2b)

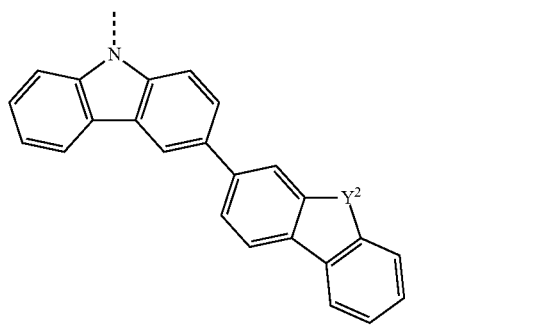

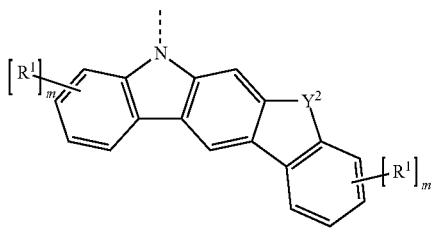

formula (6-2c)

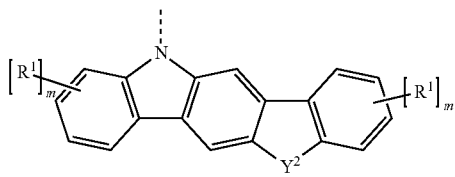

formula (6-2d)

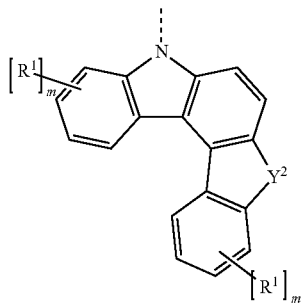

formula (6-2e)

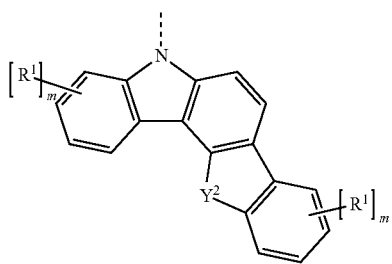

formula (6-2f)

where the symbols and indices used have the meanings given above.

In a further preferred embodiment of the invention, $Y^2$ and $Y^3$ stand, identically or differently on each occurrence, for O, $C(R^4)_2$ or $NR^4$, where the radical $R^4$ bonded to the nitrogen is not equal to H, particularly preferably for $C(R^4)_2$ or $NR^4$, where the radical $R^4$ bonded to the nitrogen is not equal to H, and very particularly preferably for $C(R^4)_2$.

If $Y^2$ or $Y^3$ stands for $NR^4$, it is preferred if this radical $R^4$ stands on each occurrence, identically or differently, for an aromatic or heteroaromatic ring system having 5 to 24 aromatic ring atoms, which may in each case be substituted by one or more radicals $R^5$, particularly preferably for an aromatic or heteroaromatic ring system having 6 to 18 aromatic ring atoms, which may be substituted by one or more radicals $R^5$. Examples of suitable substituents $R^4$ are selected from the group consisting of phenyl, biphenyl, in particular ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by a radical $R^5$ other than H or D. These groups may each be substituted by one or more radicals $R^5$, but are preferably unsubstituted. Suitable structures $R^4$ are the same structures as depicted above for $R^2$-1 to $R^2$-18.

If $Y^2$ stands for $C(R^4)_2$, it is preferred if these radicals $R^4$ stand on each occurrence, identically or differently, for a straight-chain alkyl group having 1 to 10 C atoms or a branched or cyclic alkyl group having 3 to 10 C atoms or an alkenyl group having 2 to 10 C atoms, each of which may be substituted by one or more radicals $R^5$, where one or more non-adjacent $CH_2$ groups may be replaced by O and where one or more H atoms may be replaced by D or F, or for an aromatic or heteroaromatic ring system having 5 to 24 aromatic ring atoms, which may in each case be substituted by one or more radicals $R^5$; the two substituents $R^4$ here may optionally form a monocyclic or polycyclic, aliphatic, aromatic or heteroaromatic ring system, which may be substituted by one or more radicals $R^5$. Ring formation of the two substituents $R^4$ forms a spiro system, for example a spirobifluorene or a derivative of a spirobifluorene, if the groups $R^4$ stand for phenyl groups.

In a further preferred embodiment of the invention, L stands for a single bond or an aromatic or heteroaromatic ring system having 5 to 24 aromatic ring atoms, which may be substituted by one or more radicals $R^1$. L particularly preferably stands, identically or differently on each occurrence, for a single bond or an aromatic ring system having 6 to 12 aromatic ring atoms or a heteroaromatic ring system having 6 to 13 aromatic ring atoms, each of which may be substituted by one or more radicals $R^1$, but is preferably unsubstituted. L very particularly preferably stands for a single bond. Examples of suitable aromatic or heteroaromatic ring systems L are selected from the group consisting of phenylene, biphenyl, fluorene, pyridine, pyrimidine, triazine, dibenzofuran, dibenzothiophene and carbazole, each of which may be substituted by one or more radicals $R^1$, but is preferably unsubstituted.

If the compounds according to the invention contain substituents $R^1$, these are then preferably selected from the group consisting of H, D, F, CN, $N(Ar^2)_2$, $C(=O)Ar^2$, $P(=O)(Ar^2)_2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals $R^5$, where one or more non-adjacent $CH_2$ groups may be replaced by O and where one or more H atoms may be replaced by D or F, an aromatic or heteroaromatic ring system having 5 to 24 aromatic ring atoms, which may in each case be substituted by one or more radicals $R^5$, or an aralkyl or heteroaralkyl group having 5 to 25 aromatic ring atoms, which may be substituted by one or more radicals $R^1$; two substituents $R^1$ which are bonded to adjacent carbon atoms here may optionally form a monocyclic or polycyclic, aliphatic ring system, which may be substituted by one or more radicals $R^5$.

The substituents $R^1$ are particularly preferably selected from the group consisting of H, D, F, CN, $N(Ar^2)_2$, a straight-chain alkyl group having 1 to 8 C atoms, preferably having 1, 2, 3 or 4 C atoms, or a branched or cyclic alkyl group having 3 to 8 C atoms, preferably having 3 or 4 C atoms, or an alkenyl group having 2 to 8 C atoms, preferably having 2, 3 or 4 C atoms, each of which may be substituted by one or more radicals $R^5$, but is preferably unsubstituted, or an aromatic or heteroaromatic ring system having 6 to 24 aromatic ring atoms, preferably having 6 to 18 aromatic ring atoms, particularly preferably having 6 to 13 aromatic ring atoms, which may in each case be substituted by one or more non-aromatic radicals $R^5$, but is preferably unsubstituted; two substituents $R^1$ which are bonded to adjacent carbon atoms here may optionally form a monocyclic or polycyclic, aliphatic ring system, which may be substituted by one or more radicals $R^5$, but is preferably unsubstituted.

The substituents $R^1$ are very particularly preferably selected from the group consisting of H or an aromatic or heteroaromatic ring system having 6 to 18 aromatic ring atoms, preferably having 6 to 13 aromatic ring atoms, which may in each case be substituted by one or more non-aromatic radicals $R^5$, but is preferably unsubstituted. Examples of suitable substituents $R^1$ are selected from the group consisting of phenyl, biphenyl, in particular ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^5$, but is preferably unsubstituted. Suitable structures $R^1$ here are the same structures as depicted above for $R^2$-1 to $R^2$-18.

In a further preferred embodiment of the invention, $R^5$ is selected on each occurrence, identically or differently, from the group consisting of H, D, F, CN, an aliphatic hydrocarbon radical having 1 to 10 C atoms, preferably having 1, 2, 3 or 4 C atoms, or an aromatic or heteroaromatic ring system having 5 to 30 aromatic ring atoms, preferably having 5 to 13 aromatic ring atoms, which may be substituted by one or more alkyl groups, each having 1 to 4 carbon atoms, but is preferably unsubstituted.

If the compound according to the invention is substituted by aromatic or heteroaromatic groups, it is preferred if these contain no aryl or heteroaryl groups having more than two aromatic six-membered rings condensed directly onto one another. The substituents particularly preferably contain absolutely no aryl or heteroaryl groups having six-membered rings condensed directly onto one another. This preference is due to the low triplet energy of such structures. Condensed aryl groups having more than two aromatic six-membered rings condensed directly onto one another which are nevertheless also suitable in accordance with the invention are phenanthrene and triphenylene, since these also have a high triplet level.

The preferences mentioned above may occur individually or together. It is preferred if the preferences mentioned above occur together.

Preference is thus given to compounds of the above-mentioned formula (1a) for which:
L is on each occurrence, identically or differently, a single bond or an aromatic or heteroaromatic ring system having 5 to 24 aromatic ring atoms, which may be substituted by one or more radicals $R^1$;
HetAr is a group of one of the above-mentioned formulae (2-1) to (2-10), (3-1) or (4-1);
$N^1$ is a group of the following formula (5), (6-1) or (6-2),

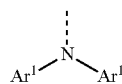

formula (5)

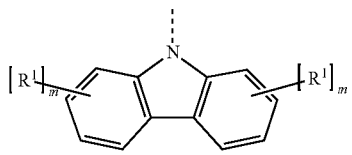

formula (6-1)

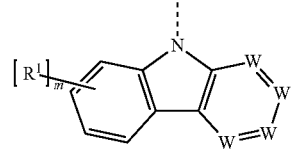

formula (6-2)

two adjacent groups W together stand for a group of the following formula (7a) or (8a) and the other two groups W stand for $CR^1$ and preferably for CH,

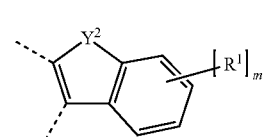

formula (7a)

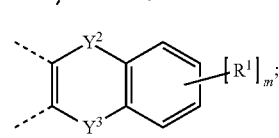

formula (8a)

$Ar^1$ is on each occurrence, identically or differently, an aromatic or heteroaromatic ring system having 6 to 24 aromatic ring atoms, preferably having 6 to 18 aromatic ring atoms, which may be substituted by one or more radicals $R^3$;
$Y^2$, $Y^3$ are, identically or differently on each occurrence, O, $NR^4$ or $C(R^4)_2$, where the radical $R^4$ which is bonded to N is not equal to H;
$R^1$ is selected on each occurrence, identically or differently, from the group consisting of H, D, F, CN, $N(Ar^2)_2$, $C(=O)Ar^2$, $P(=O)(Ar^2)_2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals $R^5$, where one or more non-adjacent $CH_2$ groups may be replaced by O and where one or more H atoms may be replaced by D or F, an aromatic or heteroaromatic ring system having 5 to 24 aromatic ring atoms, which may in each case be substituted by one or more radicals $R^5$, or an aralkyl or heteroaralkyl group having 5 to 25 aromatic ring atoms, which may be substituted by one or more radicals $R^1$; two substituents $R^1$ which are bonded to adjacent carbon atoms here may optionally form a monocyclic or polycyclic, aliphatic ring system, which may be substituted by one or more radicals $R^5$;
$R^2$ is on each occurrence, identically or differently, H or an aromatic or heteroaromatic ring system having 6 to 24 aromatic ring atoms, in particular having 6 to 18 aromatic ring atoms, which may in each case be substituted by one or more radicals $R^5$;
$R^3$ is on each occurrence, identically or differently, H, an alkyl group having 1 to 4 C atoms or an aromatic or heteroaromatic ring system having 5 to 14 aromatic ring atoms;
$R^4$ is, for $Y^2$ or $Y^3$=$NR^4$, an aromatic or heteroaromatic ring system having 5 to 24 aromatic ring atoms, preferably having 6 to 18 aromatic ring atoms, which may in each case be substituted by one or more radicals $R^5$;
and is, for $Y^2$ or $Y^3$=$C(R^4)_2$, on each occurrence, identically or differently, a straight-chain alkyl group having 1 to 10 C atoms or a branched or cyclic alkyl group having 3 to 10 C atoms or an alkenyl group having 2 to 10 C atoms, each of which may be substituted by one or more radicals $R^5$, where one or more non-adjacent $CH_2$ groups may be replaced by O and where one or more H atoms may be replaced by D or F, or an aromatic or heteroaromatic ring system having 5 to 24 aromatic ring atoms, which may in each case be substituted by one or more radicals $R^5$; the two substituents $R^4$ here may optionally form a monocyclic or polycyclic, aliphatic, aromatic or heteroaromatic ring system, which may be substituted by one or more radicals $R^5$;

$R^5$ is selected on each occurrence, identically or differently, from the group consisting of H, D, F, CN, an aliphatic hydrocarbon radical having 1 to 10 C atoms or an aromatic or heteroaromatic ring system having 5 to 30 aromatic ring atoms, which may be substituted by one or more alkyl groups, each having 1 to 4 carbon atoms;

n is on each occurrence, identically or differently, 0, 1, 2 or 3, preferably 0, 1 or 2;

m is, identically or differently on each occurrence, 0, 1, 2, 3 or 4, preferably 0, 1, 2 or 3;

the other symbols have the meanings given above.

Particular preference is given to the compounds of the above-mentioned formulae (1b) to (1g) for which:

L is on each occurrence, identically or differently, a single bond or an aromatic ring system having 6 to 12 aromatic ring atoms or a heteroaromatic ring system having 6 to 13 aromatic ring atoms, each of which may be substituted by one or more radicals $R^1$, but is preferably unsubstituted;

HetAr is a group of one of the above-mentioned formulae (2-1a) to (2-10a), (3-1a) or (4-1a);

$N^1$ is a group of the above-mentioned formulae (5), (6-1) or (6-2a) to (6-2f);

$Ar^1$ is selected on each occurrence, identically or differently, from the group consisting of phenyl, biphenyl, terphenyl, quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals R, but is preferably unsubstituted, and is in particular selected from the above-mentioned groups of the formulae ($Ar^1$-1) to ($Ar^1$-20);

$Y^2$, $Y^3$ are, identically or differently on each occurrence, $NR^4$ or $C(R^4)_2$, where the radical $R^4$ which is bonded to N is not equal to H, and are in particular $C(R^4)_2$;

$R^1$ is selected on each occurrence, identically or differently, from the group consisting of H, D, F, CN, $N(Ar^2)_2$, a straight-chain alkyl group having 1 to 8 C atoms, preferably having 1, 2, 3 or 4 C atoms, or a branched or cyclic alkyl group having 3 to 8 C atoms, preferably having 3 or 4 C atoms, or an alkenyl group having 2 to 8 C atoms, preferably having 2, 3 or 4 C atoms, each of which may be substituted by one or more radicals $R^5$, but is preferably unsubstituted, or an aromatic or heteroaromatic ring system having 6 to 24 aromatic ring atoms, preferably having 6 to 18 aromatic ring atoms, particularly preferably having 6 to 13 aromatic ring atoms, which may in each case be substituted by one or more non-aromatic radicals $R^5$, but is preferably unsubstituted; two substituents $R^1$ which are bonded to adjacent carbon atoms here may optionally form a monocyclic or polycyclic, aliphatic ring system, which may be substituted by one or more radicals $R^5$, but is preferably unsubstituted; $R^1$ is particularly preferably selected, identically or differently on each occurrence, from the group consisting of H or an aromatic or heteroaromatic ring system having 6 to 18 aromatic ring atoms, preferably having 6 to 13 aromatic ring atoms, which may in each case be substituted by one or more non-aromatic radicals $R^5$, but is preferably unsubstituted;

$R^2$ is selected, identically or differently on each occurrence, from the group consisting of phenyl, biphenyl, terphenyl, quaterphenyl, in particular branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^5$, and is in particular selected from the groups of the above-mentioned structures $R^2$-1 to $R^2$-18;

$R^3$ is H or an alkyl group having 1 to 4 C atoms;

$R^4$ is, for $Y^2$ or $Y^3=NR^4$, selected from the group consisting of phenyl, biphenyl, terphenyl, quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by a radical $R^5$ other than H or D, where these groups may each be substituted by one or more radicals $R^5$; particular preference is given to the structures $R^2$-1 to $R^2$-18 depicted above;

and is, for $Y^2$ or $Y^3=C(R^4)_2$, on each occurrence, Identically or differently, a straight-chain alkyl group having 1 to 5 C atoms or a branched or cyclic alkyl group having 3 to 8 C atoms or an alkenyl group having 2 to 8 C atoms, each of which may be substituted by one or more radicals $R^5$, where one or more non-adjacent $CH_2$ groups may be replaced by O and where one or more H atoms may be replaced by D or F, or an aromatic or heteroaromatic ring system having 6 to 18 aromatic ring atoms, which may in each case be substituted by one or more radicals $R^5$; the two substituents $R^4$ here may optionally form a monocyclic or polycyclic, aliphatic, aromatic or heteroaromatic ring system, which may be substituted by one or more radicals $R^5$;

$R^5$ is selected on each occurrence, identically or differently, from the group consisting of H, D, F, CN, an aliphatic hydrocarbon radical having 1, 2, 3 or 4 C atoms or an aromatic or heteroaromatic ring system having 5 to 13 aromatic ring atoms, which may be substituted by one or more alkyl groups, each having 1 to 4 carbon atoms, but is preferably unsubstituted;

n is on each occurrence, identically or differently, 0 or 1;

m is, identically or differently on each occurrence, 0, 1 or 2, preferably 0 or 1;

the other symbols have the meanings given above.

Examples of suitable compounds according to the invention are the structures shown below.

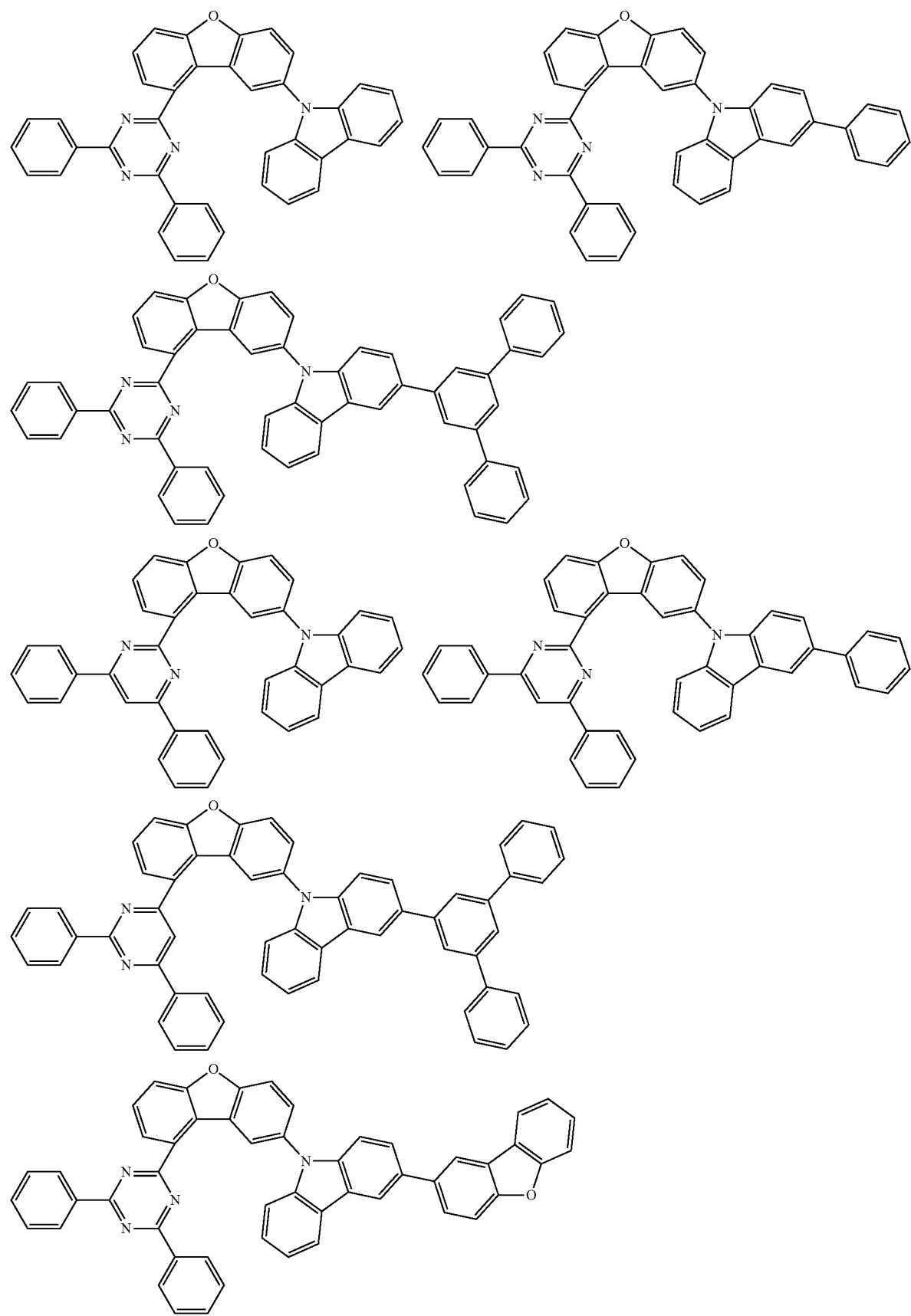

-continued
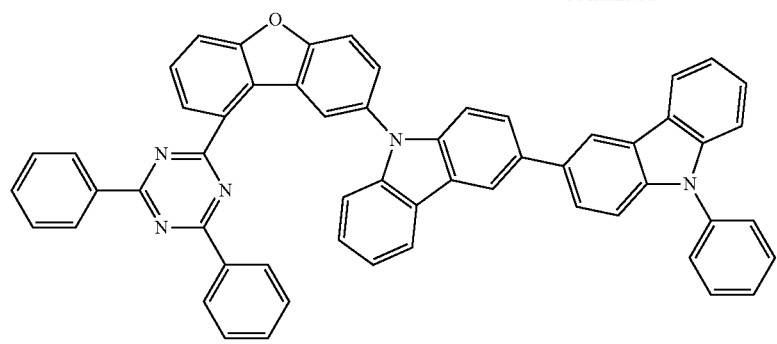
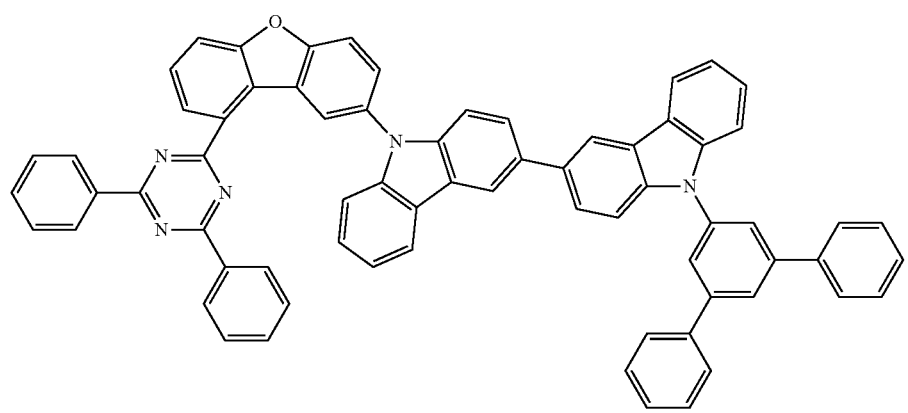
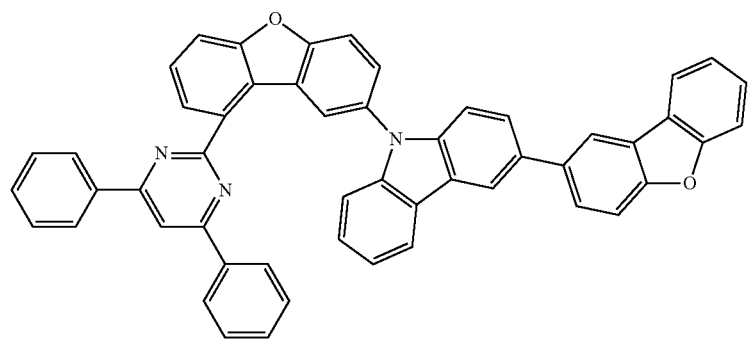
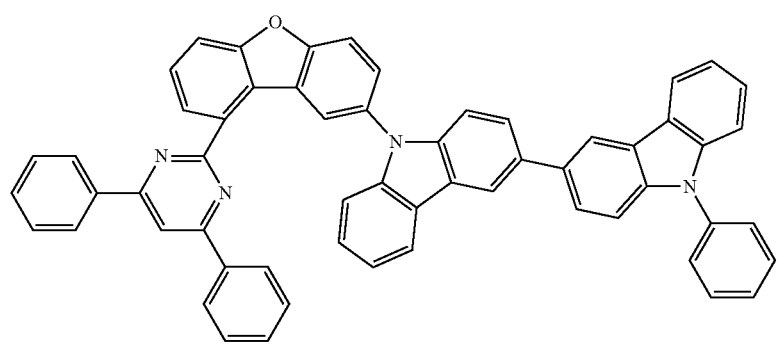

-continued
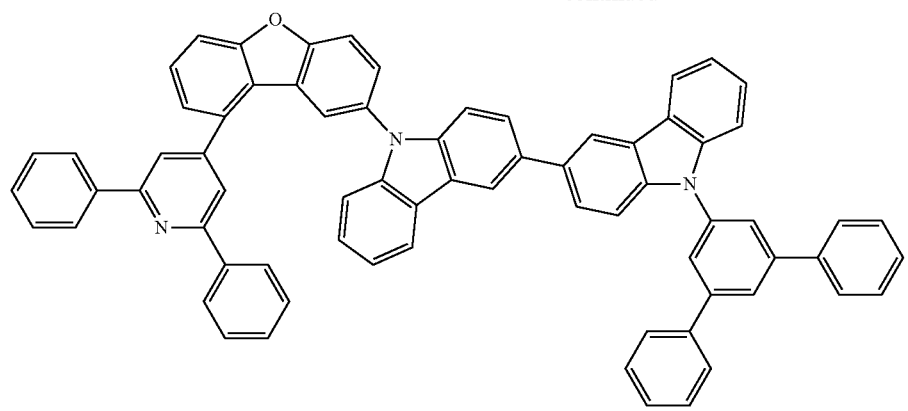
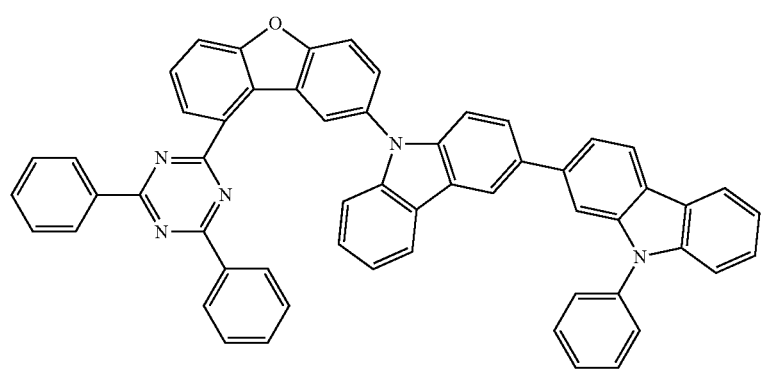
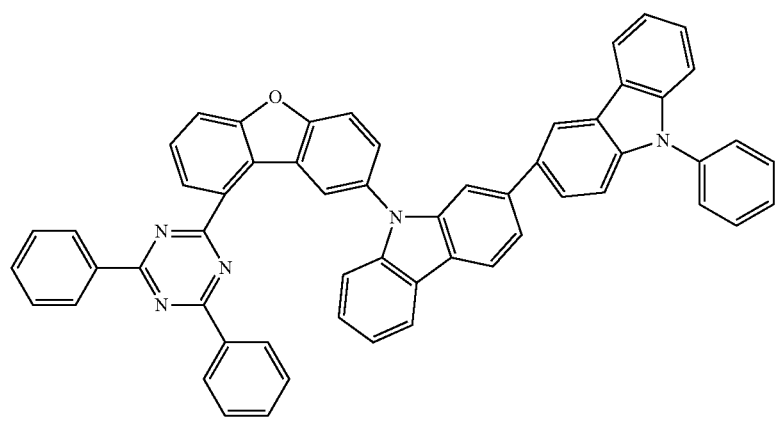
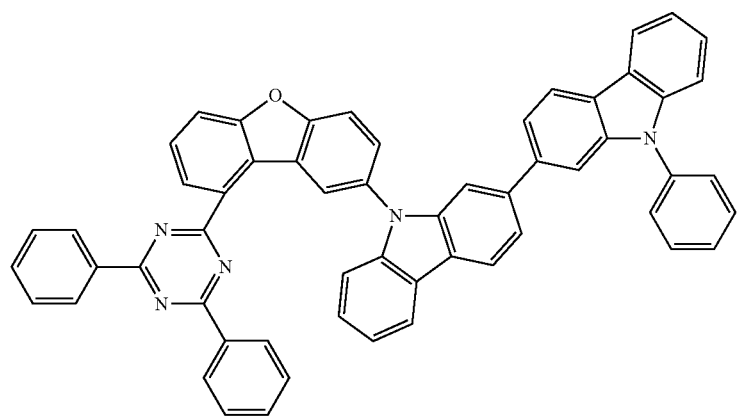

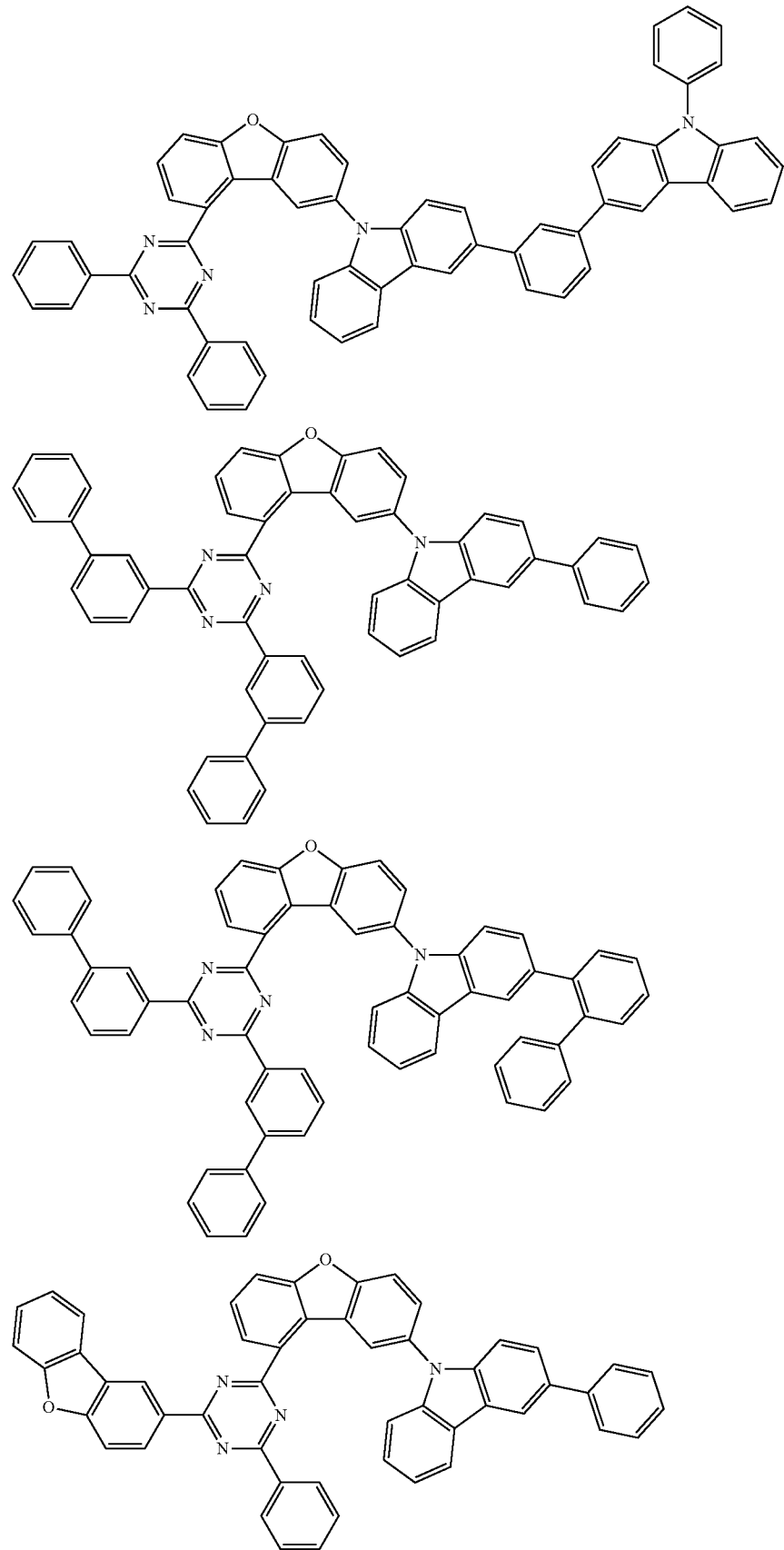

-continued
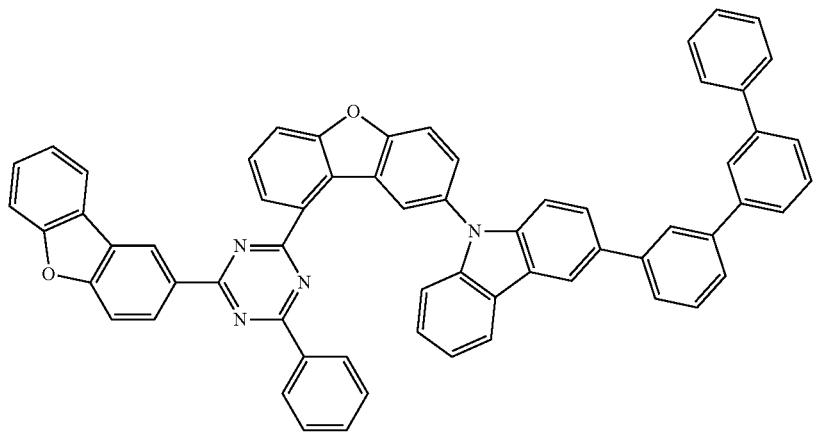
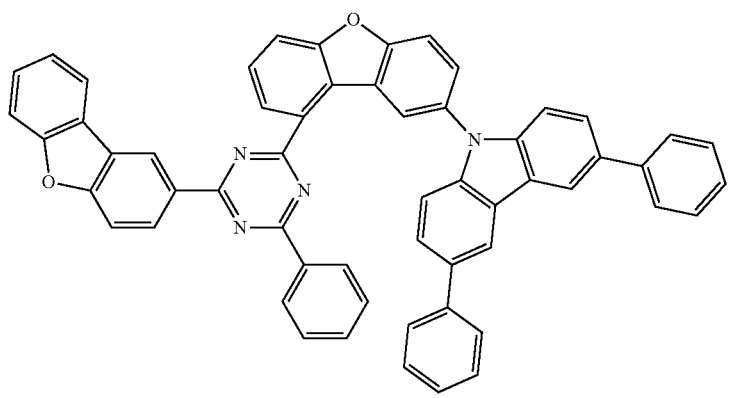
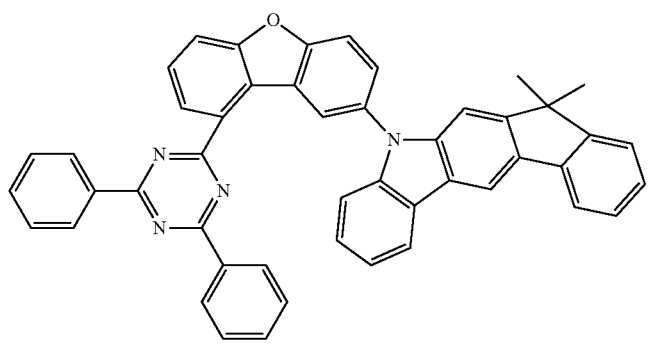
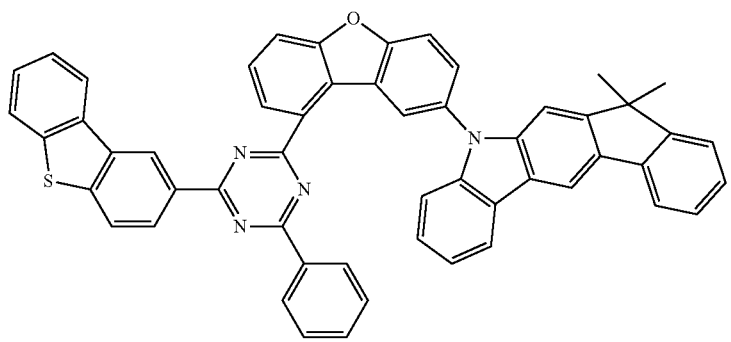

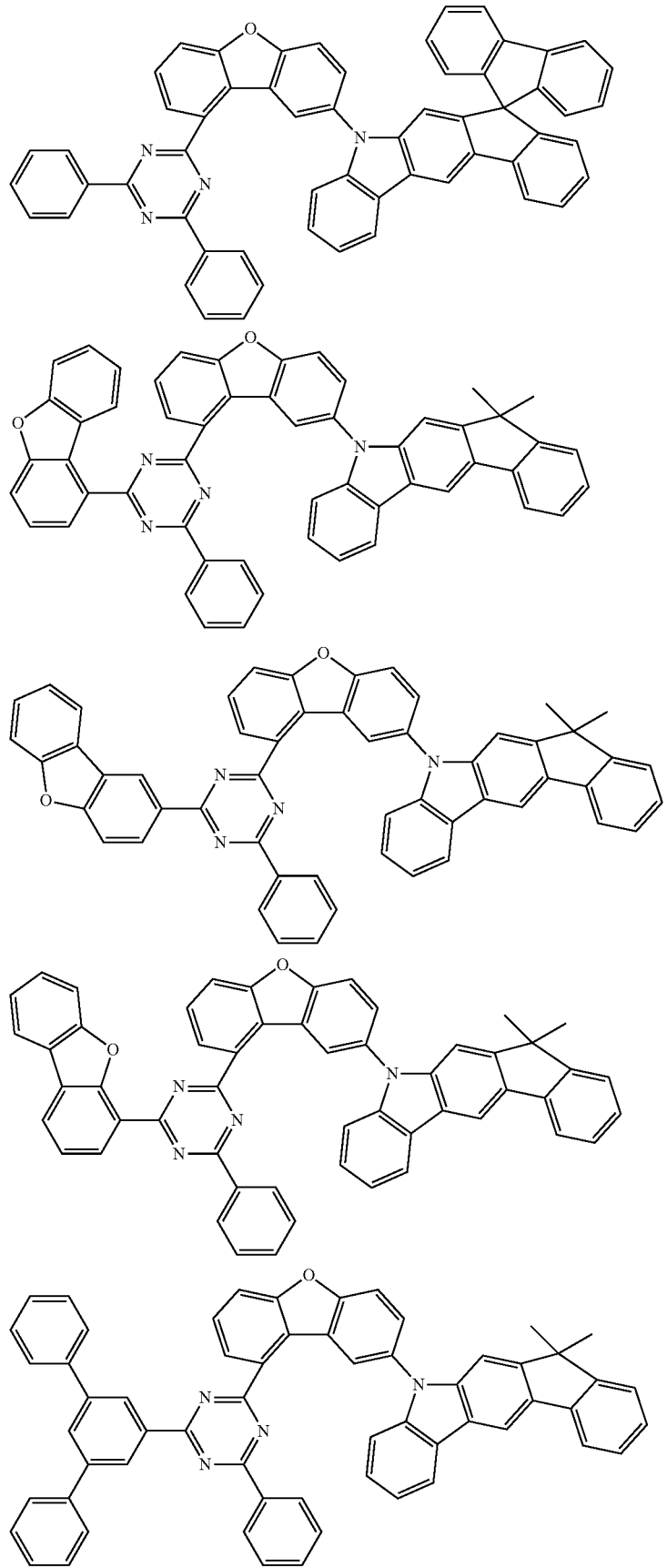

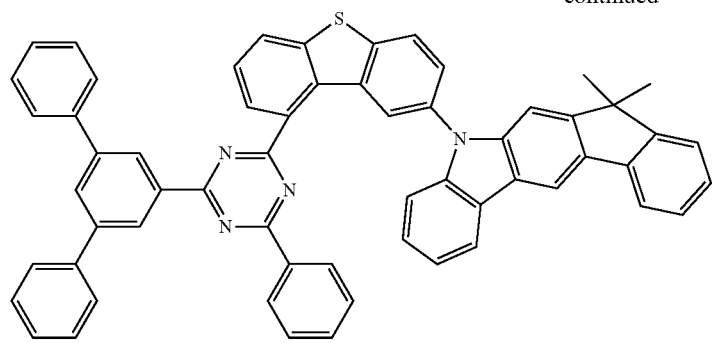
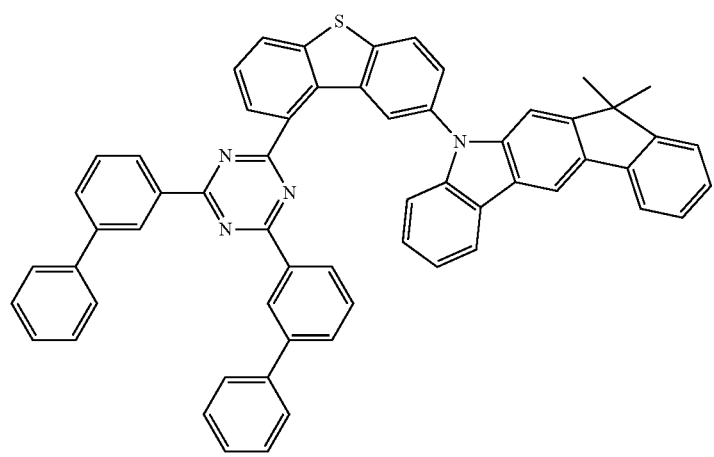
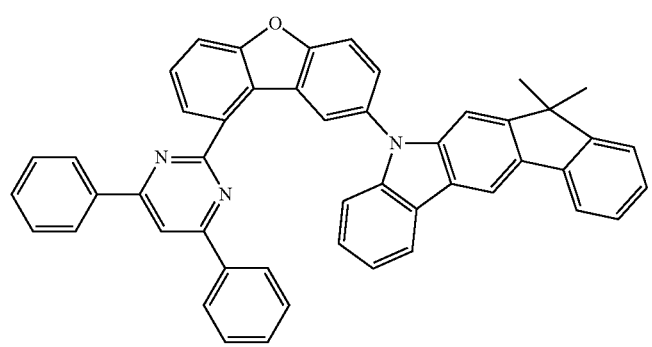
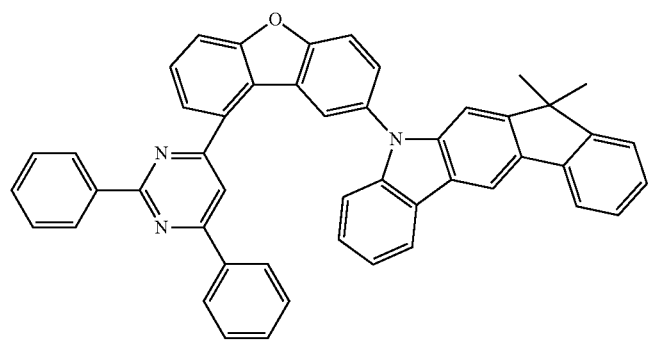

-continued
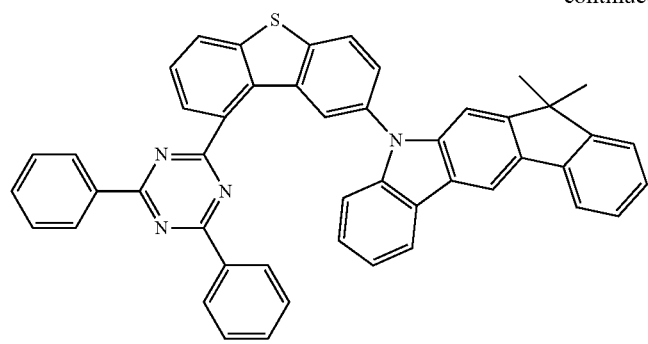
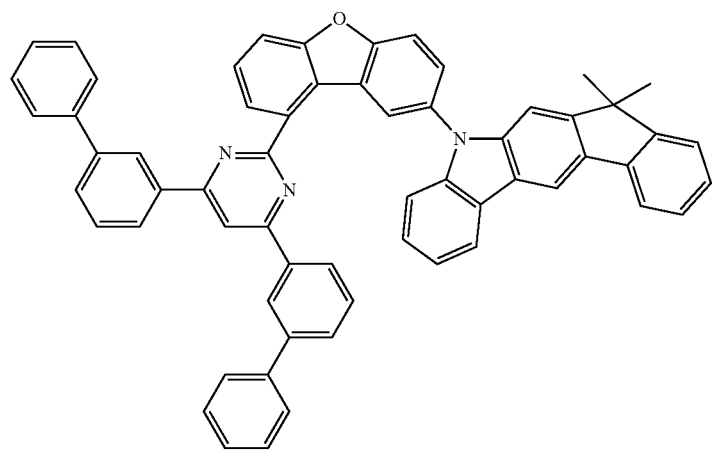
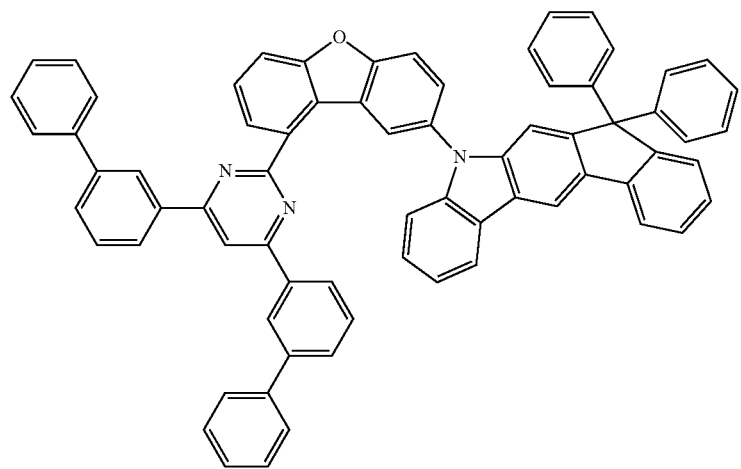
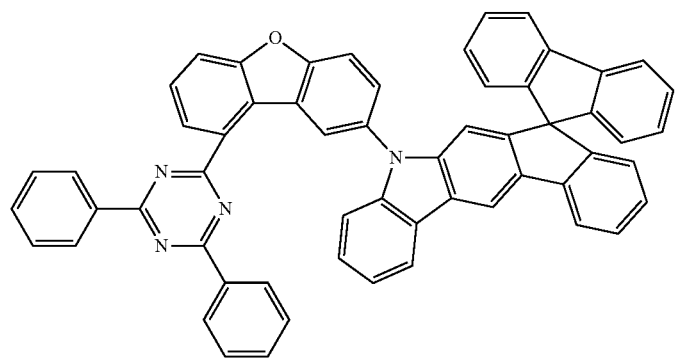

-continued
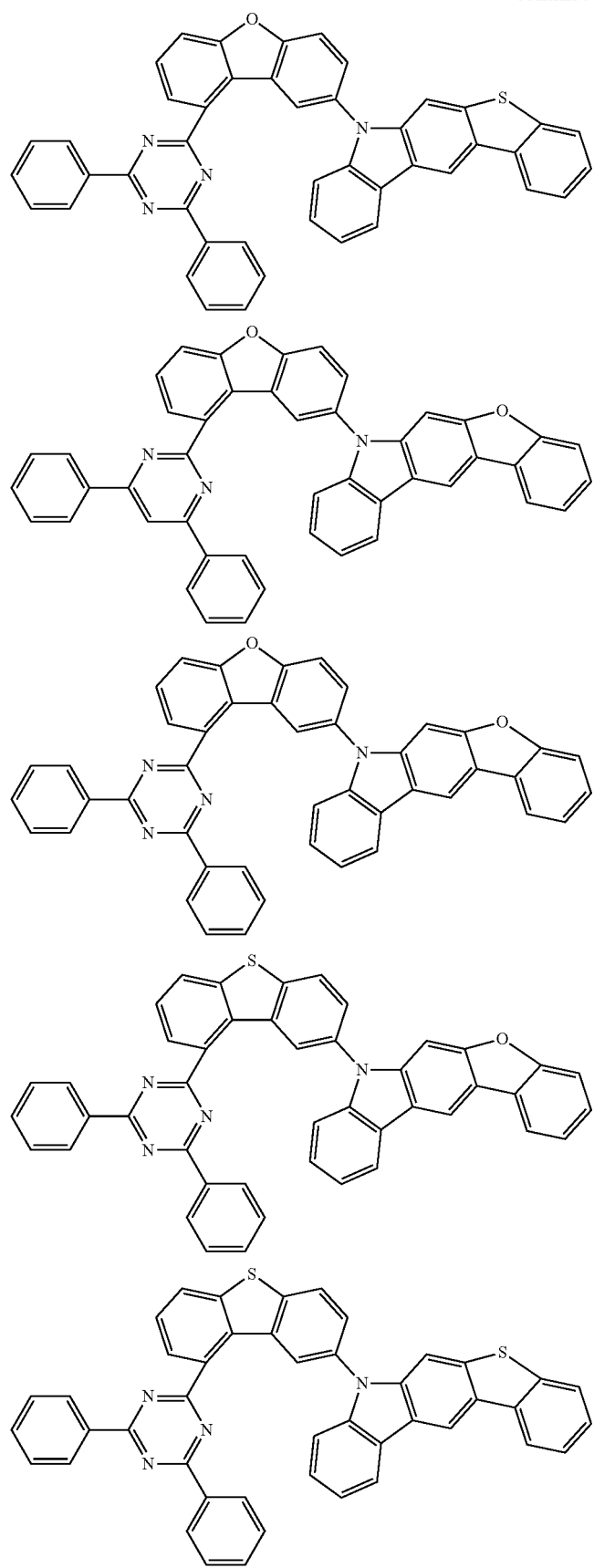

-continued
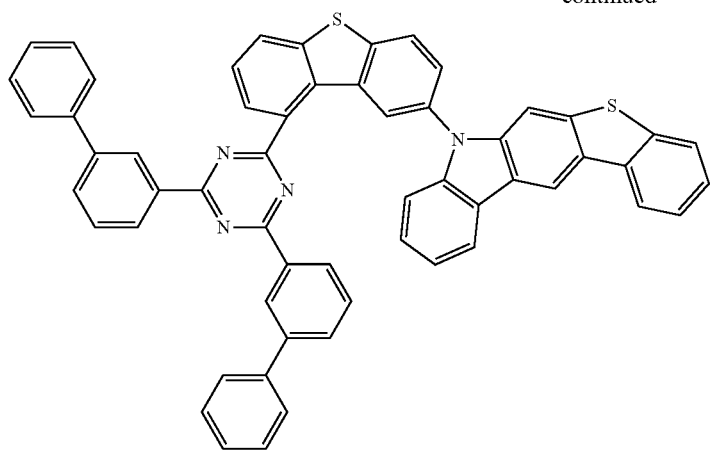
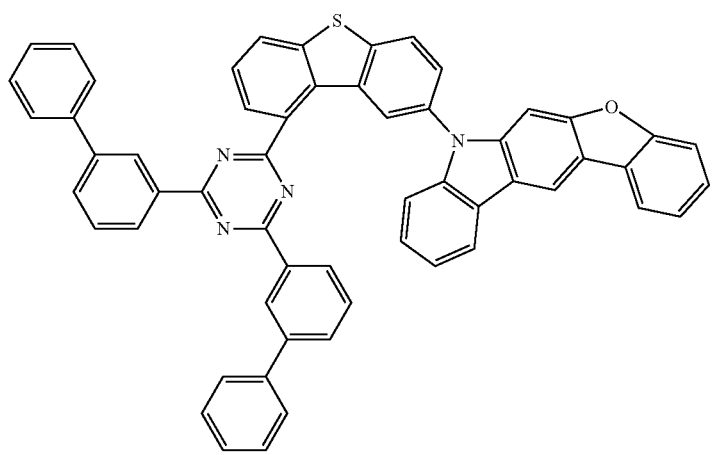
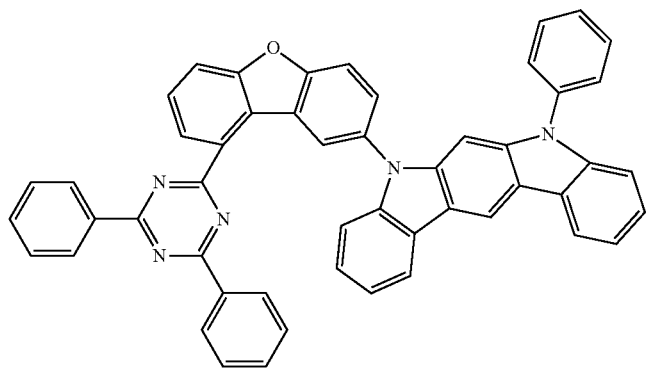

-continued
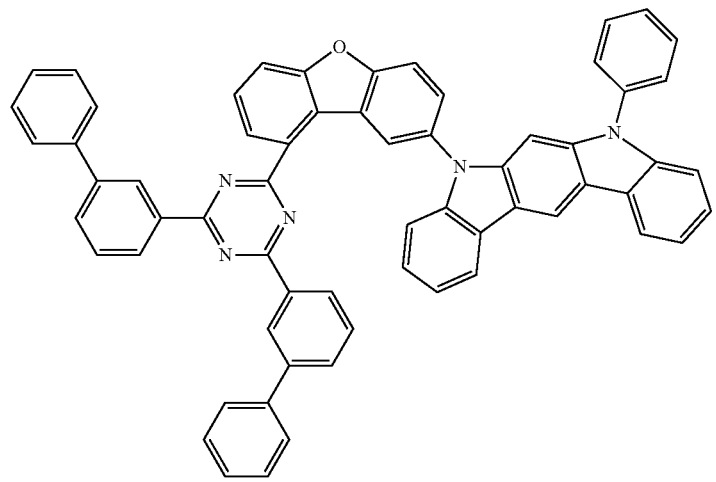
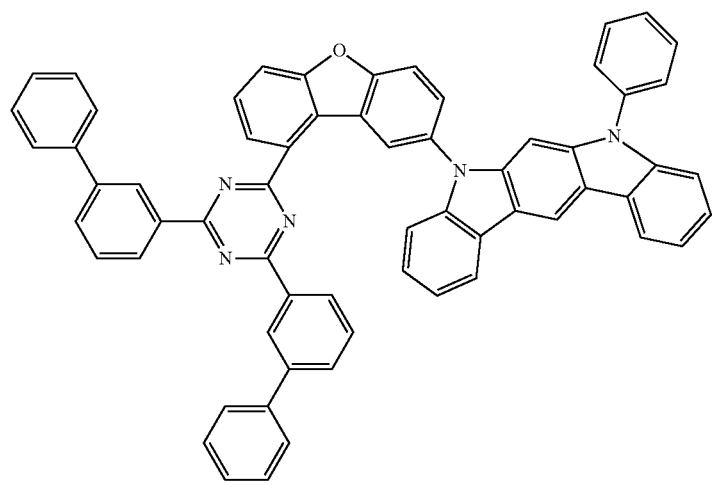
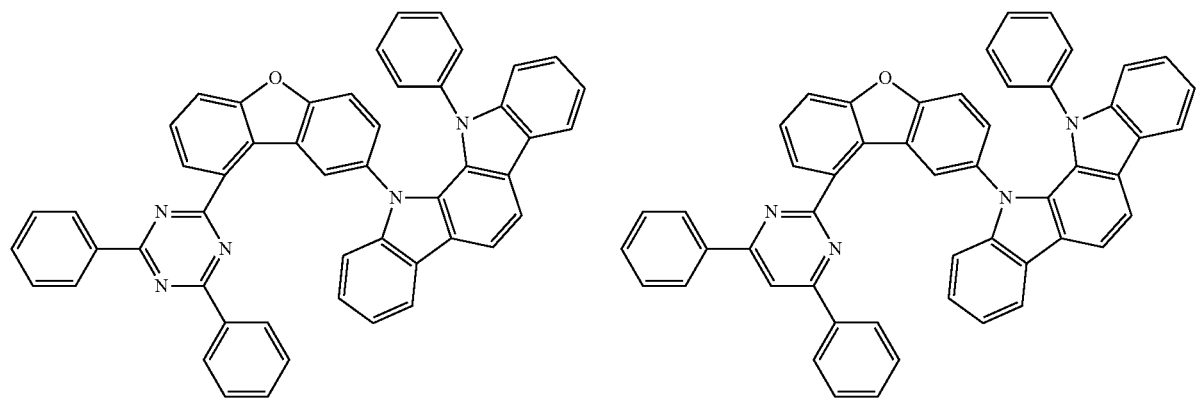

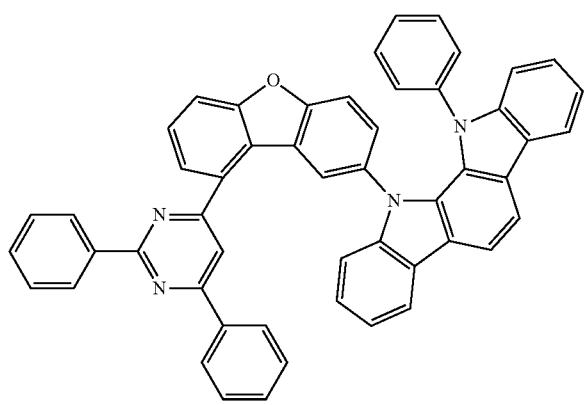
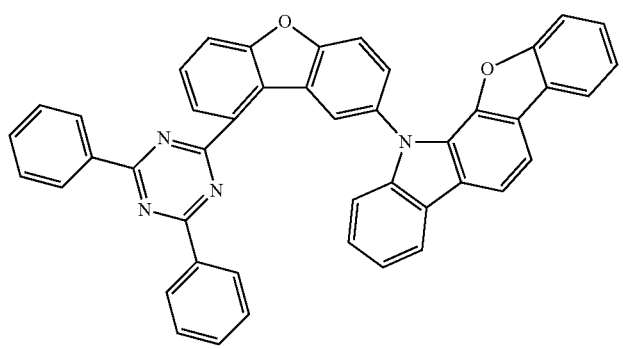
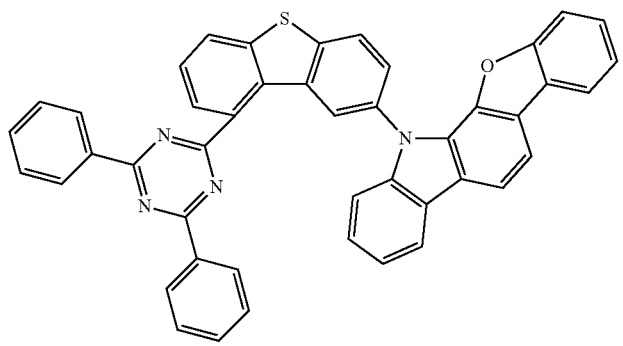
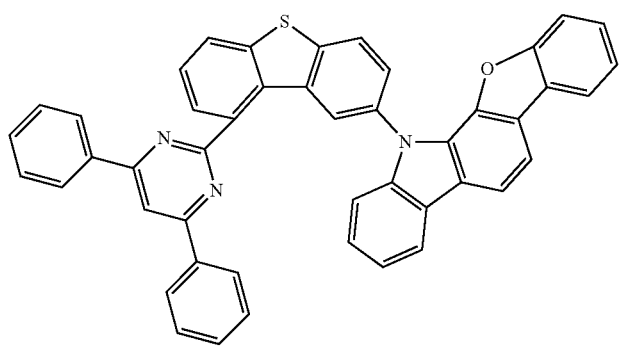

-continued
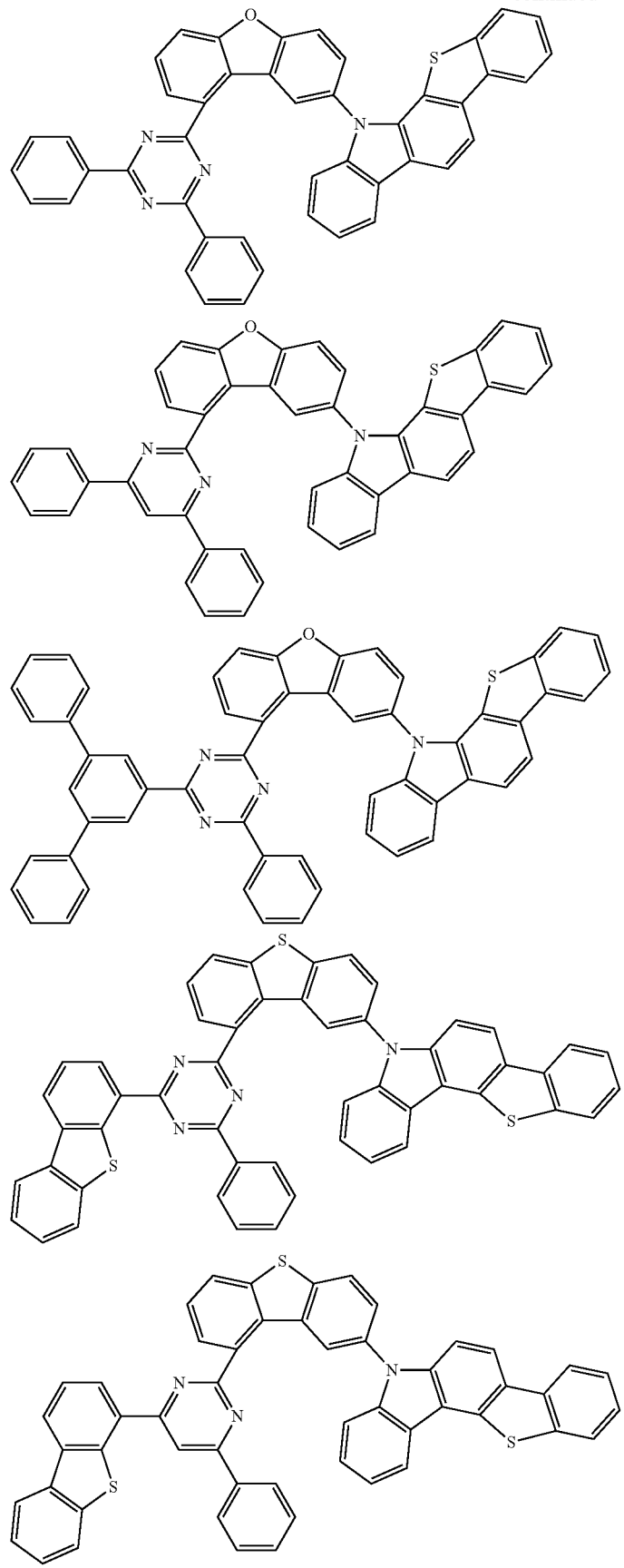

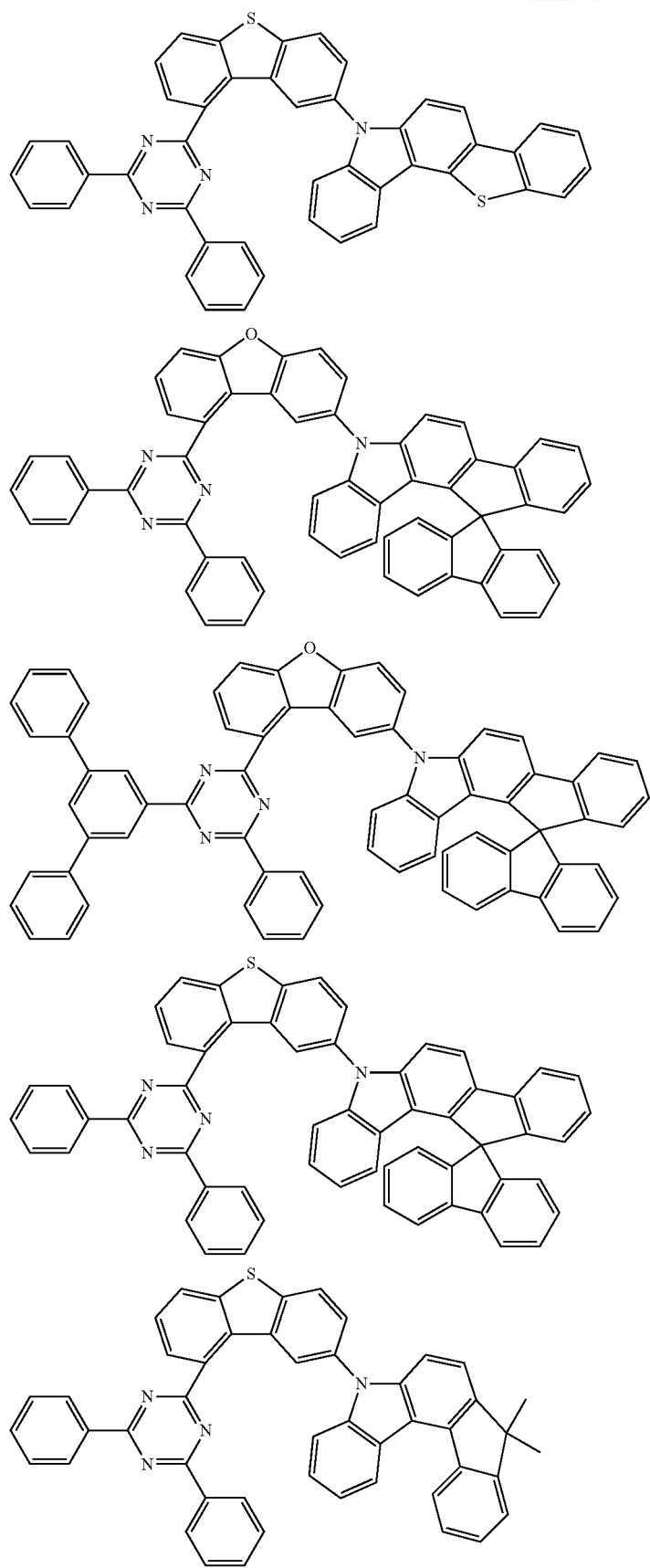

-continued
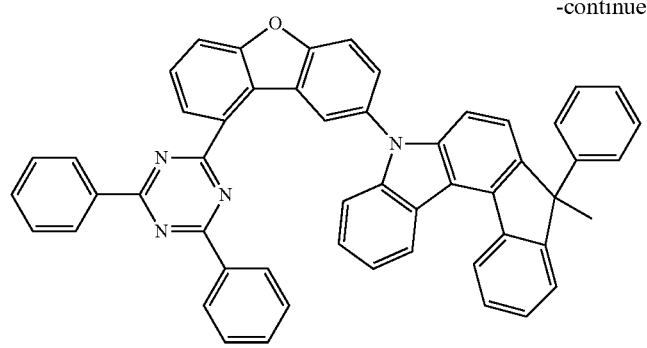
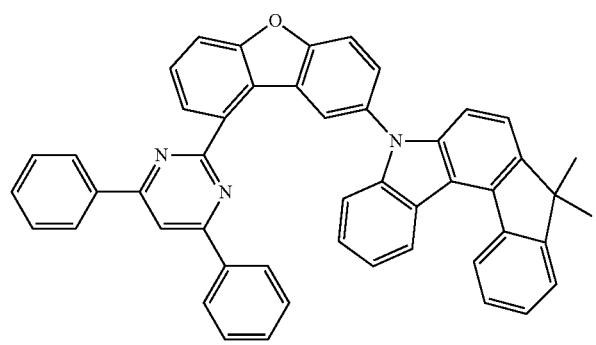
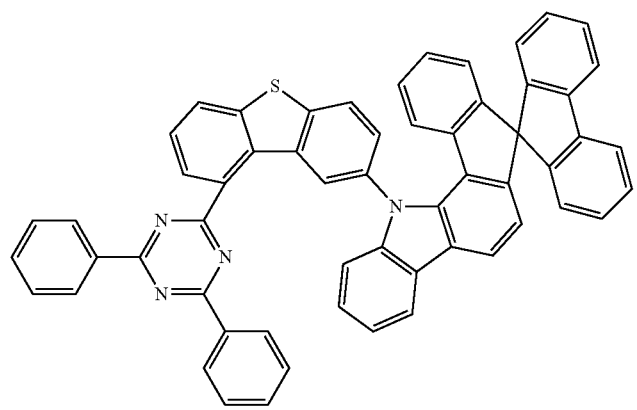
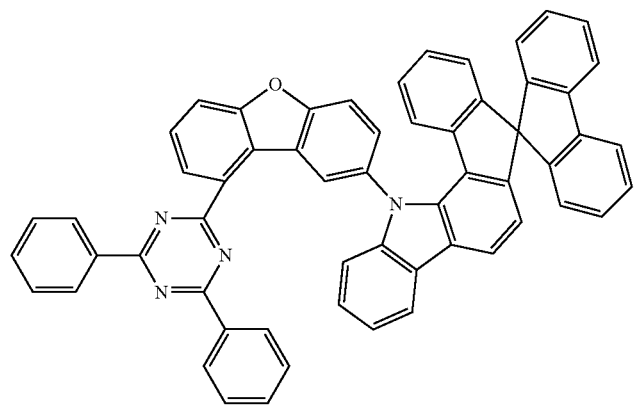

-continued
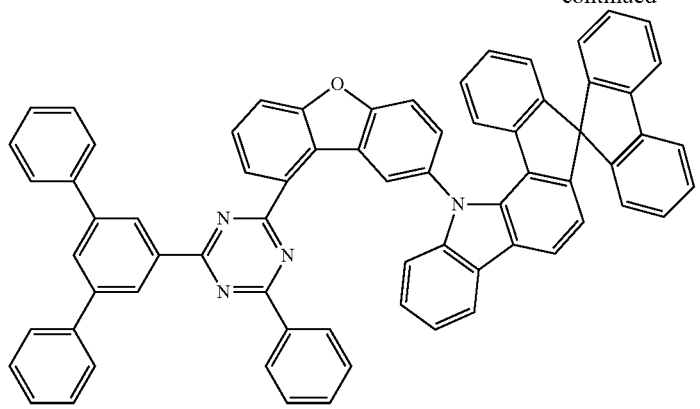
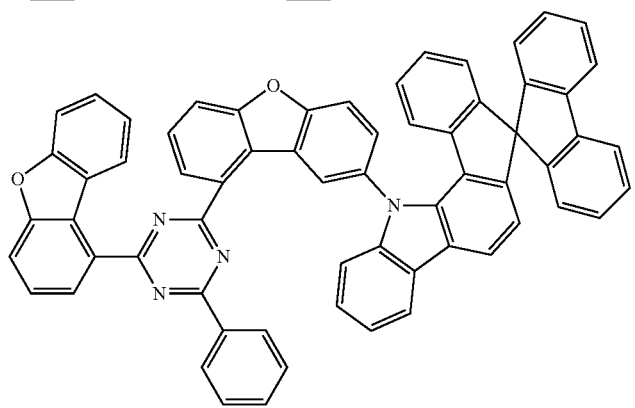
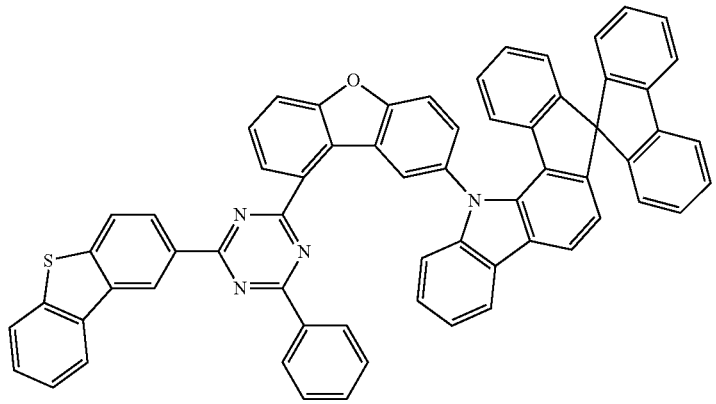
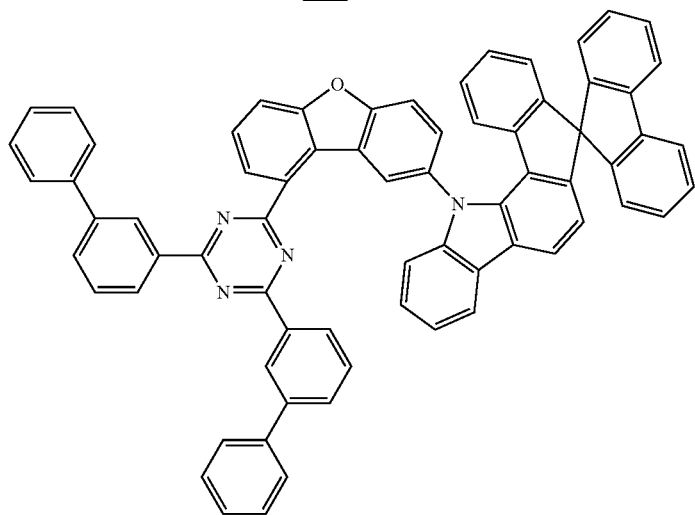

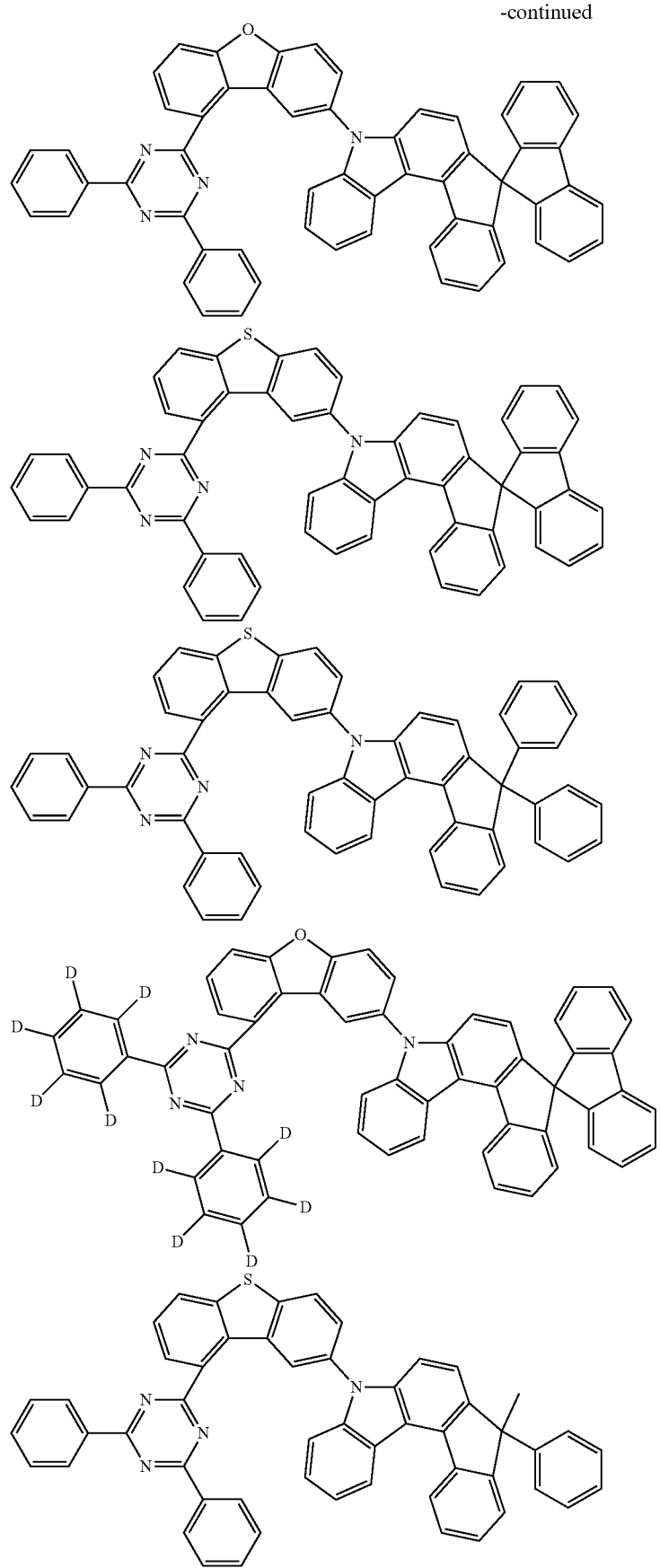

-continued
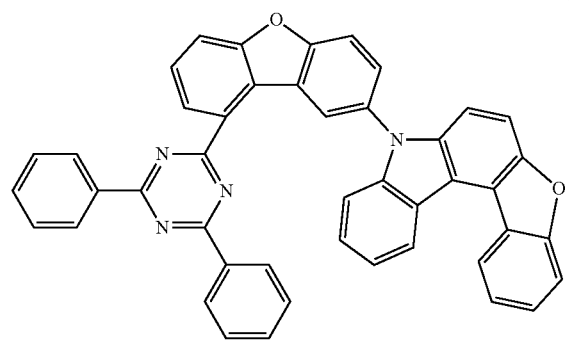
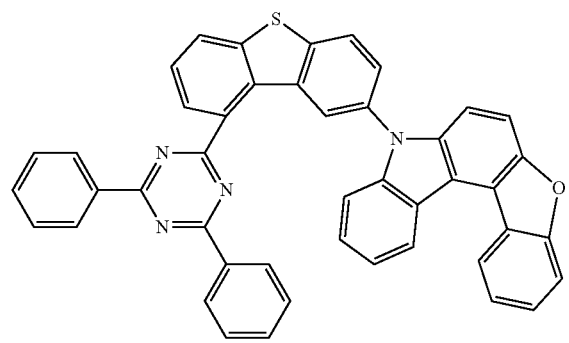
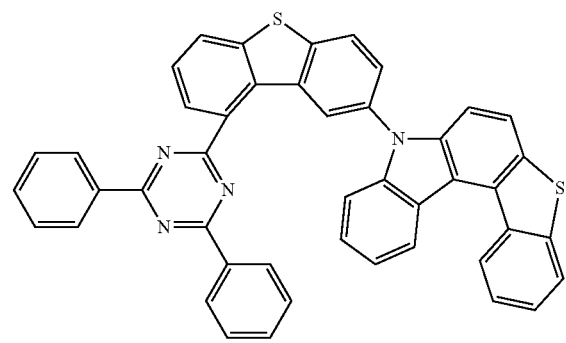
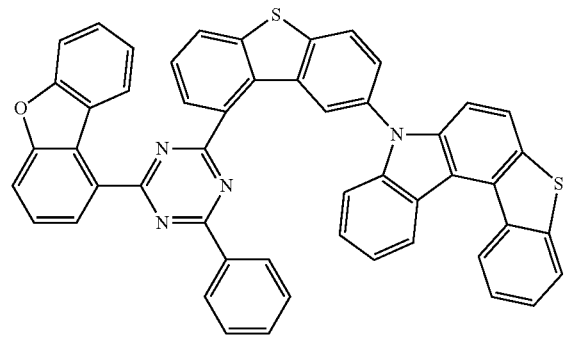
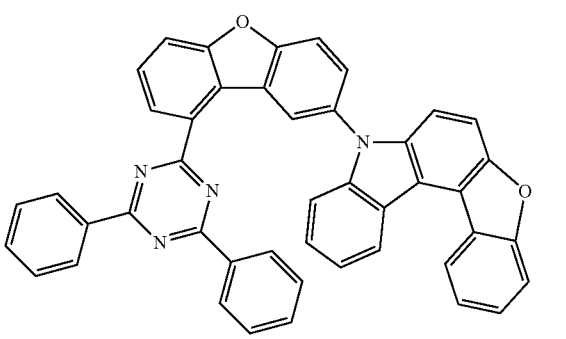
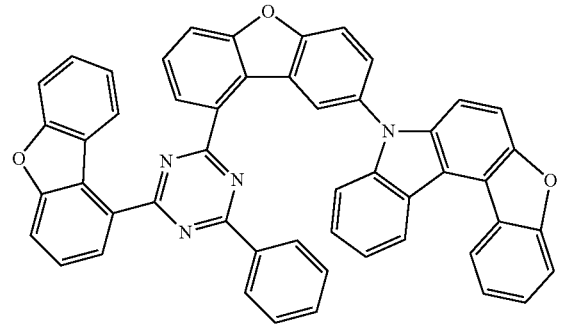
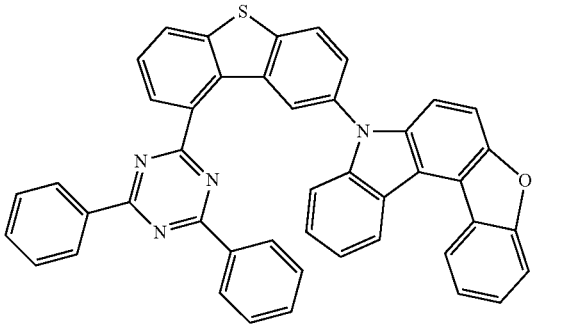
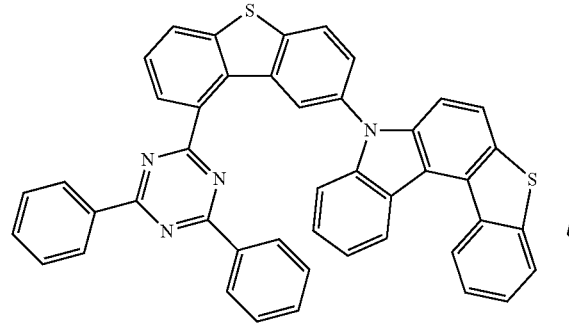
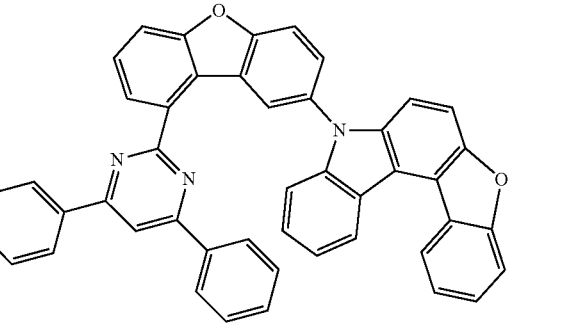

-continued
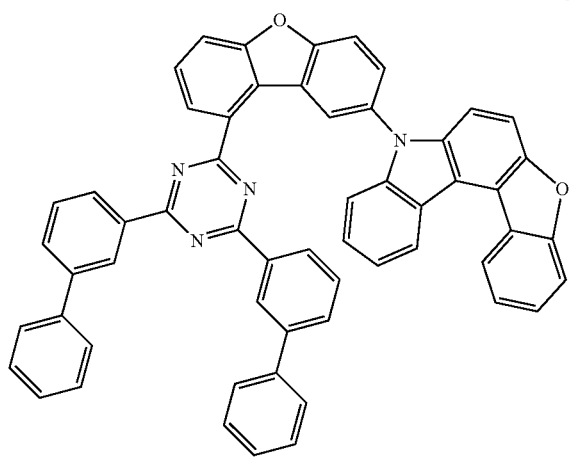
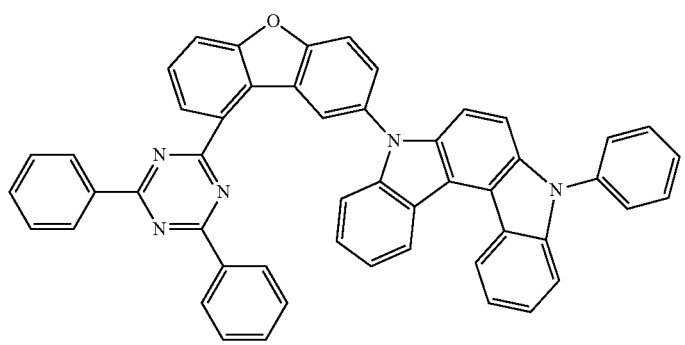
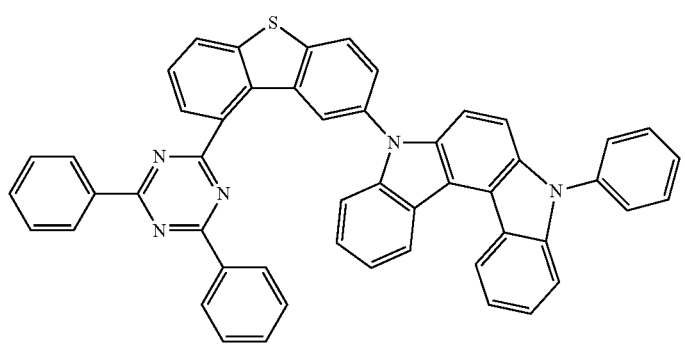
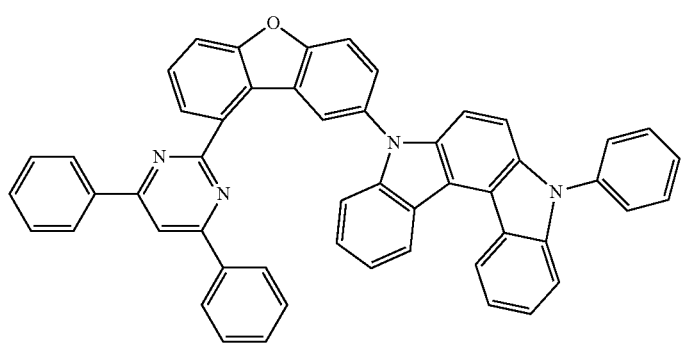

-continued
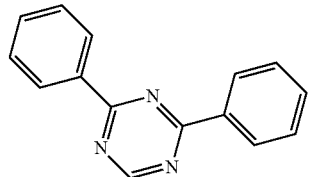
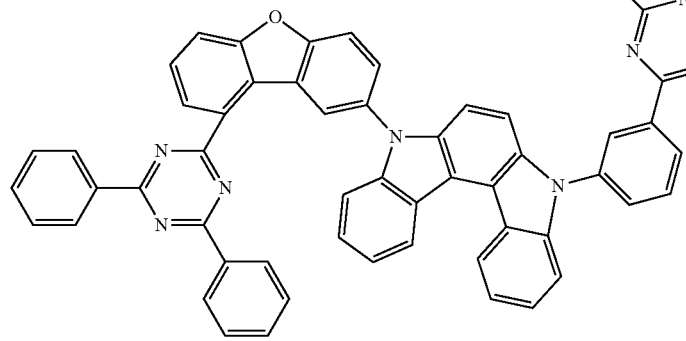
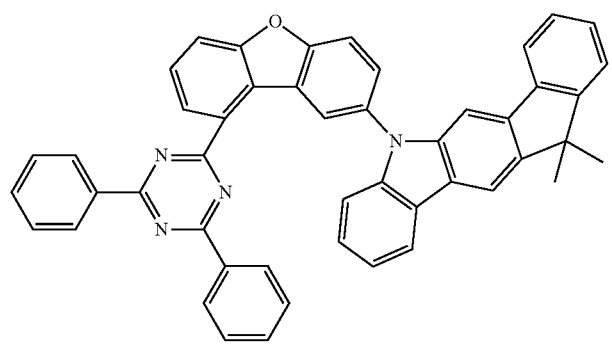
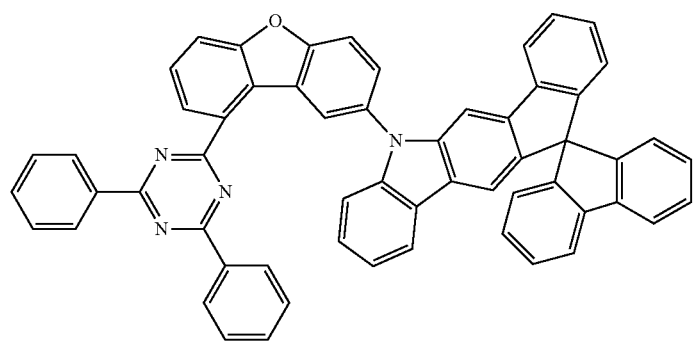
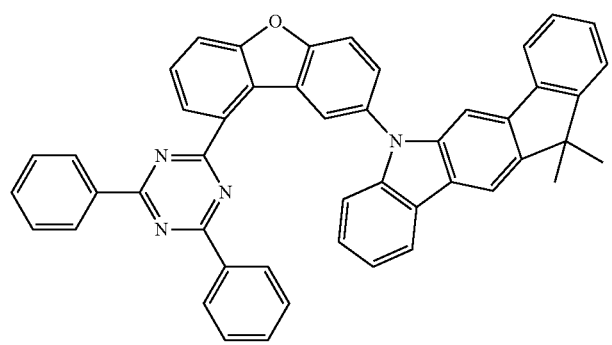

-continued
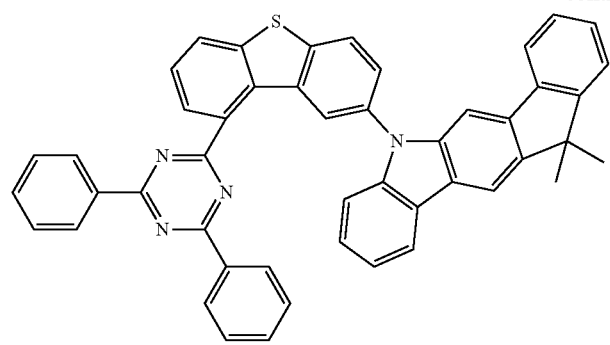
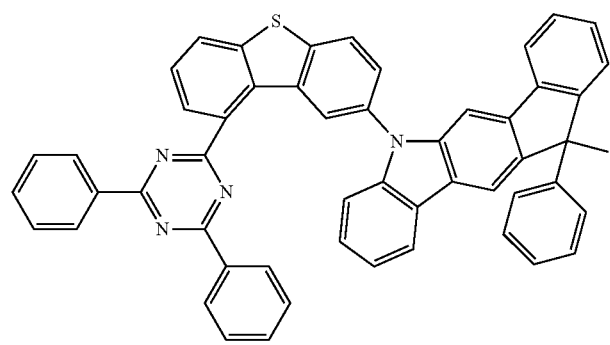
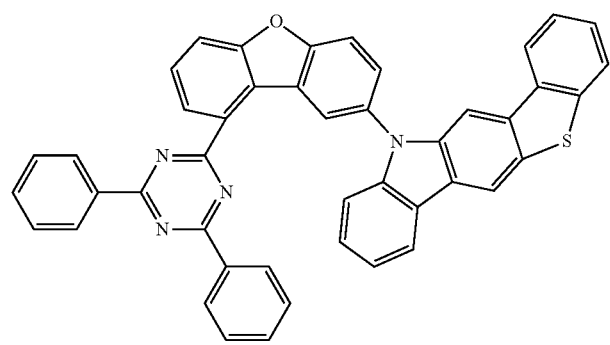
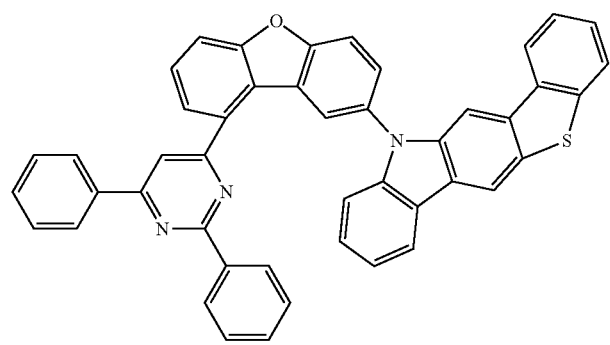
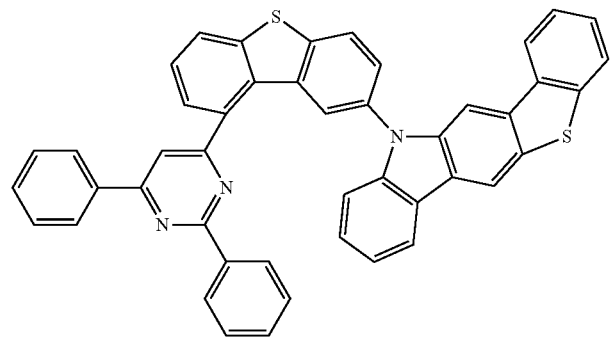

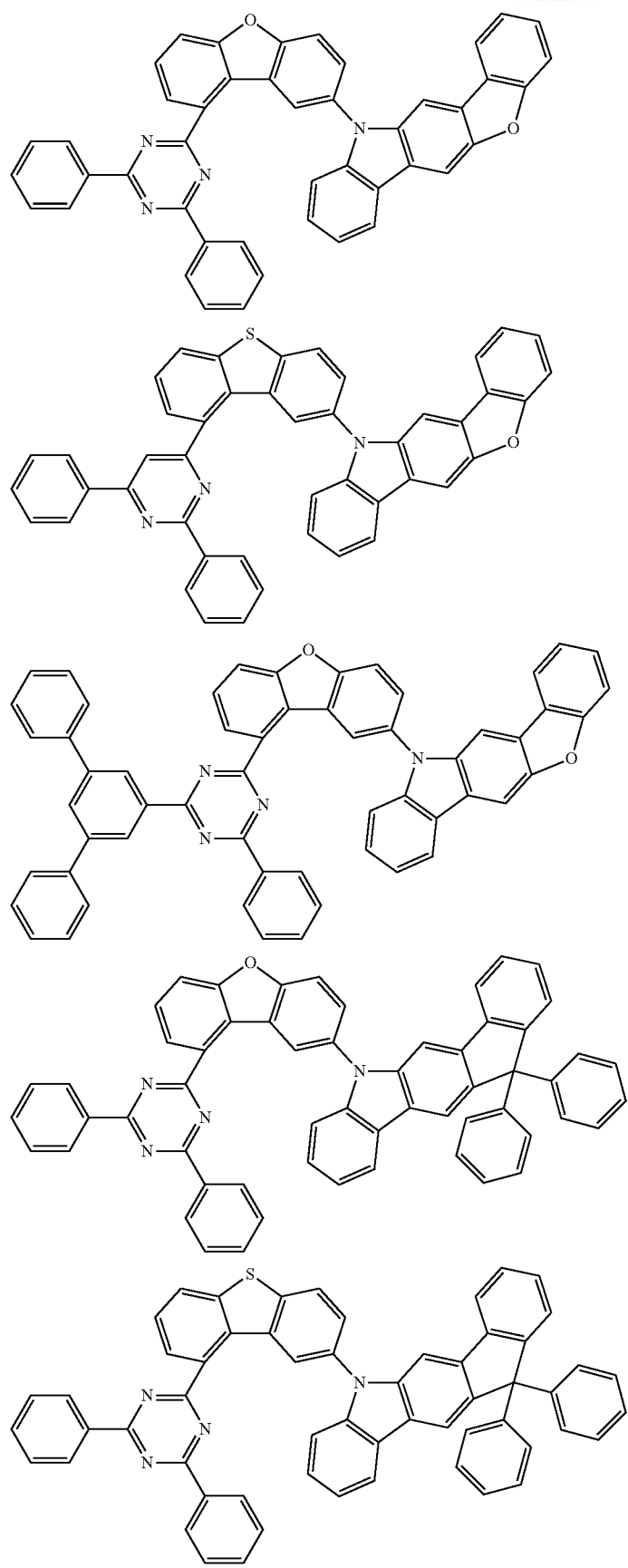

-continued
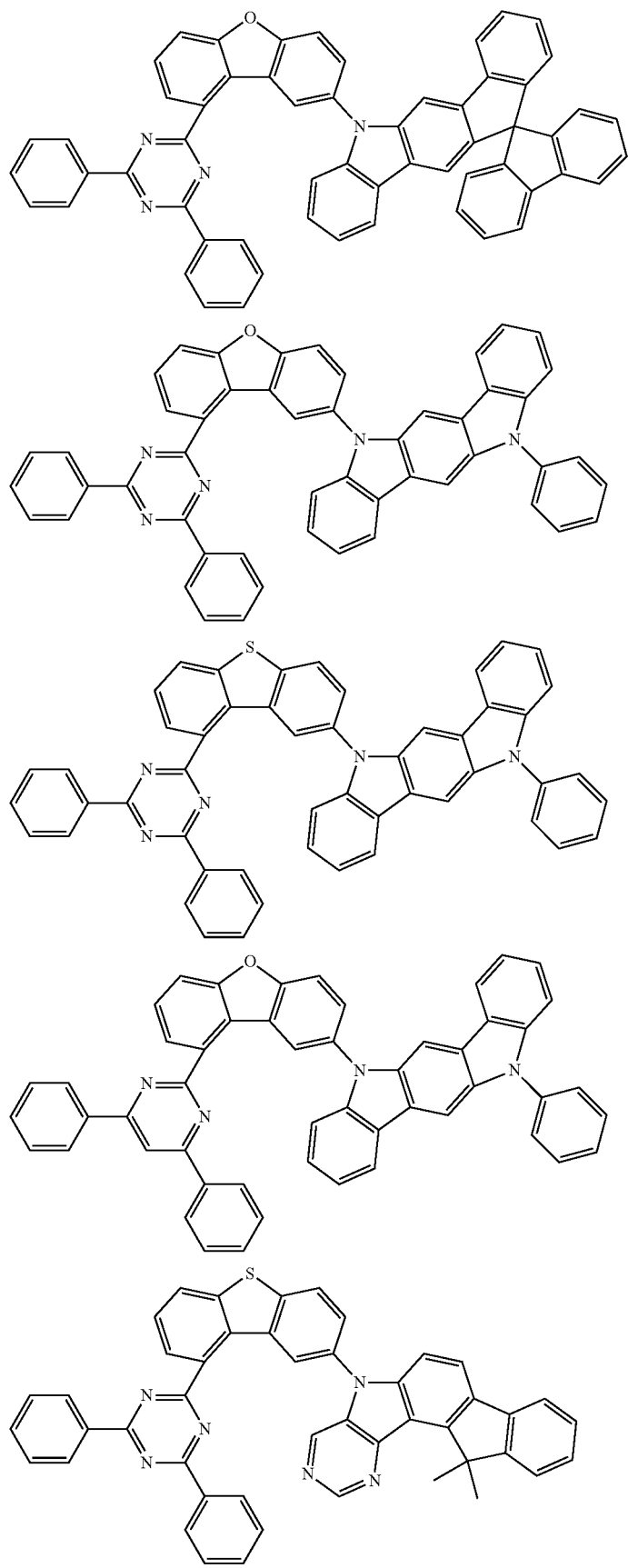

-continued
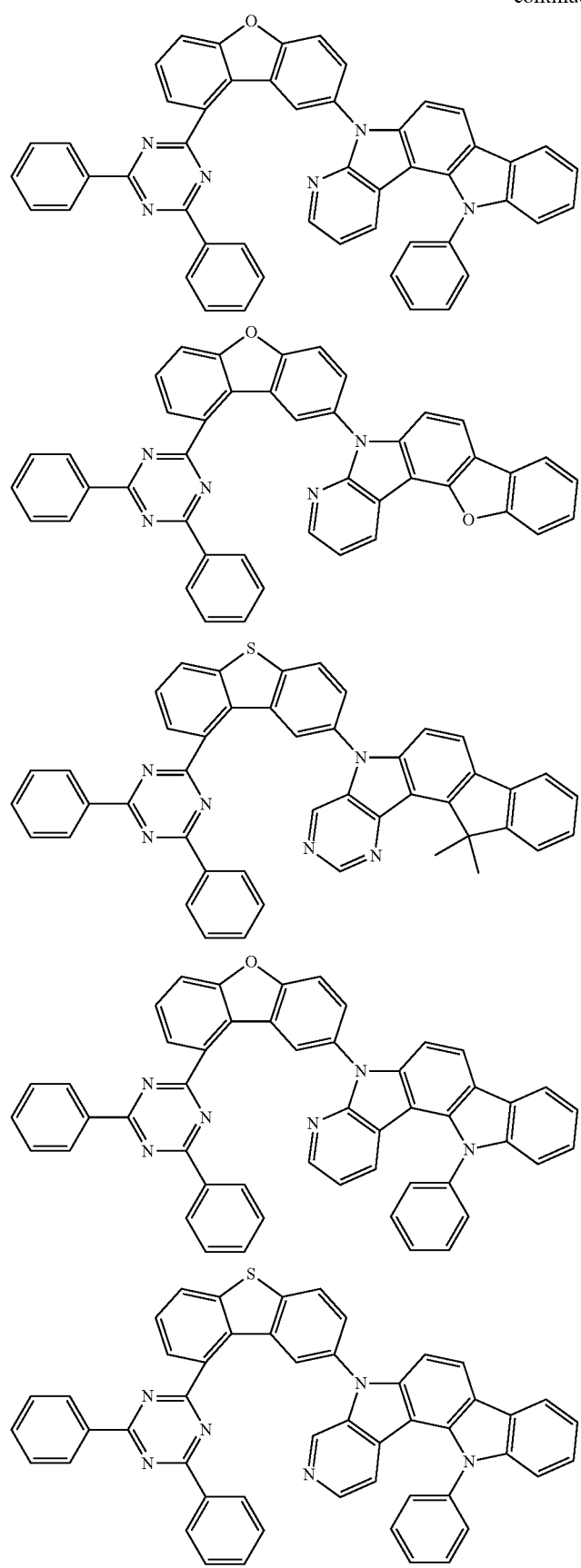

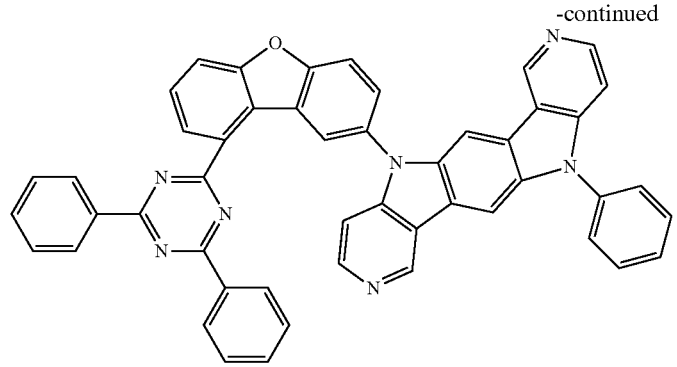
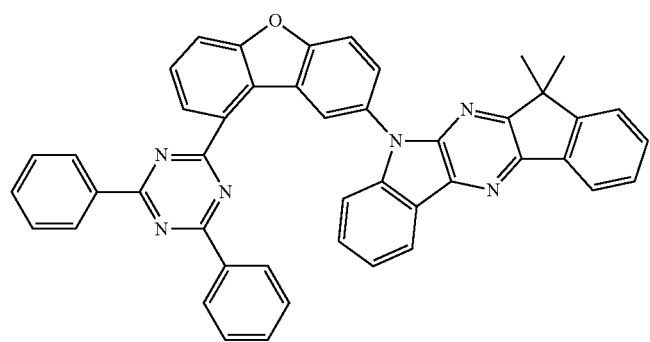
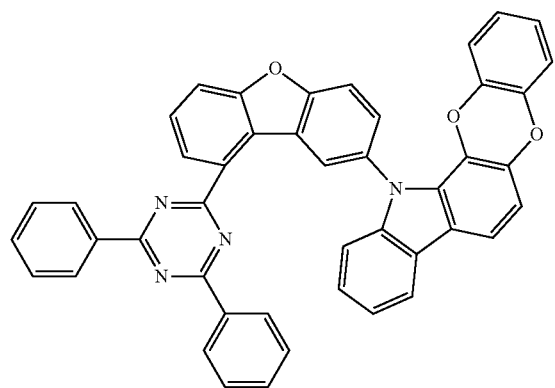
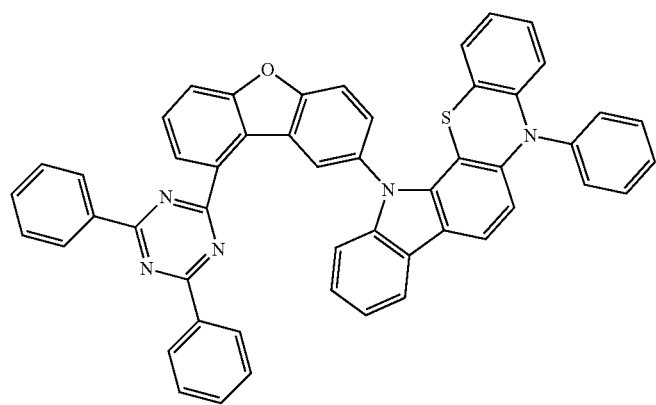

-continued
77
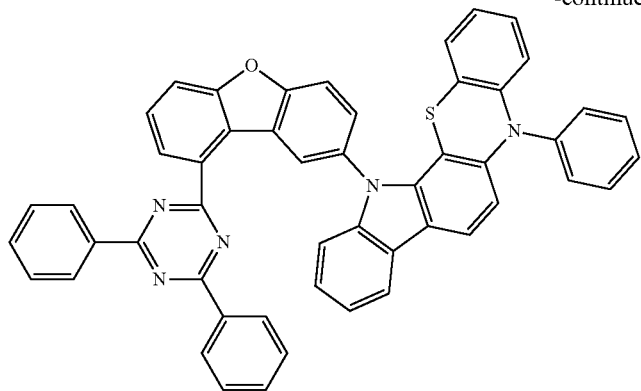
78
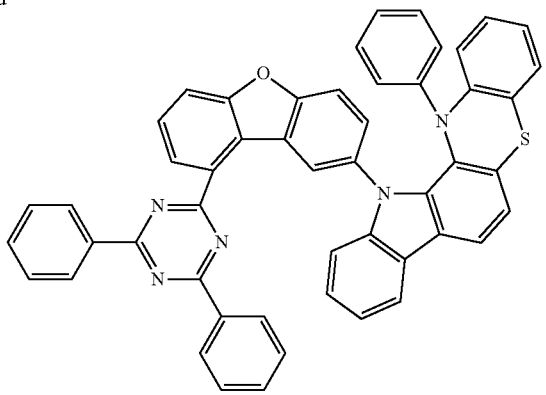
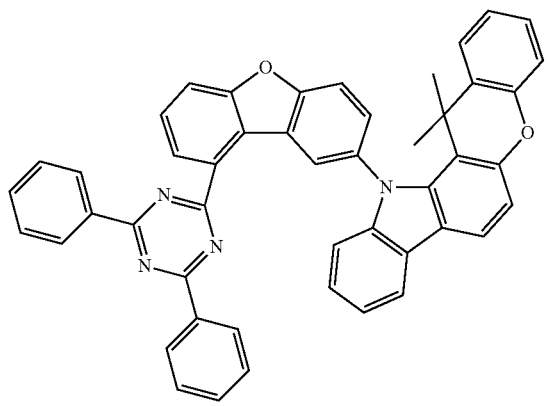
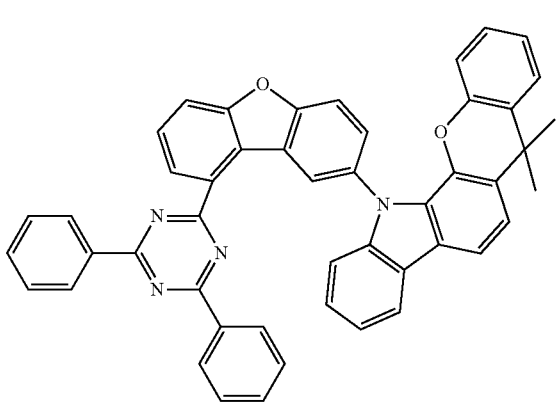
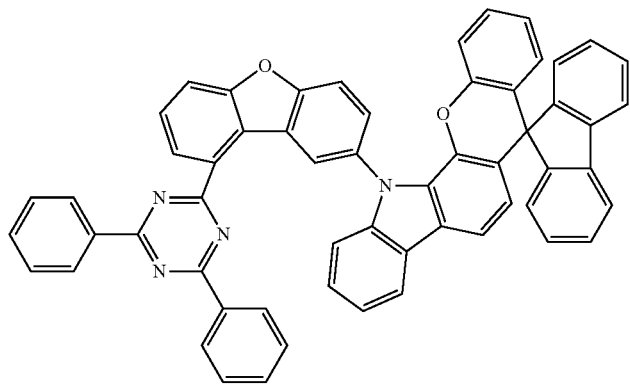
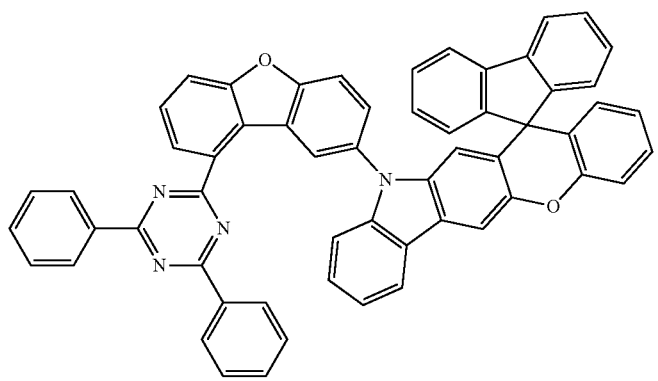

-continued
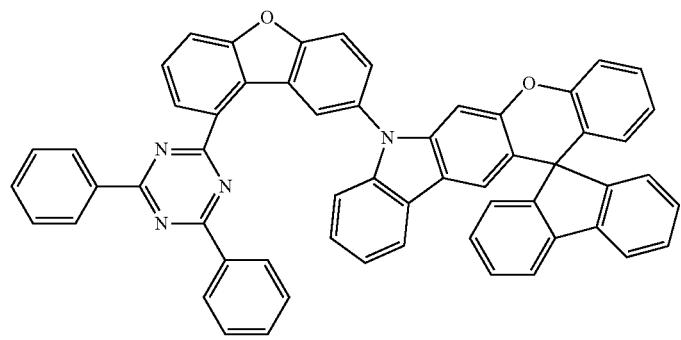
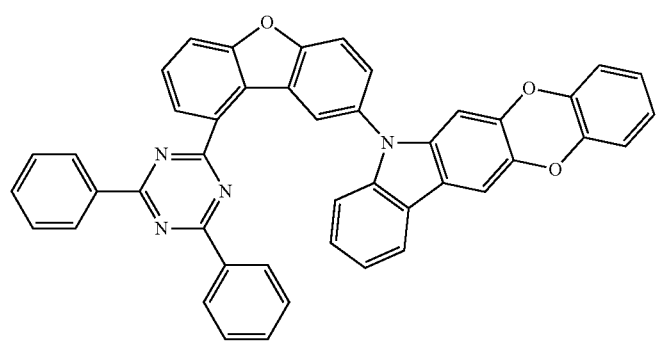
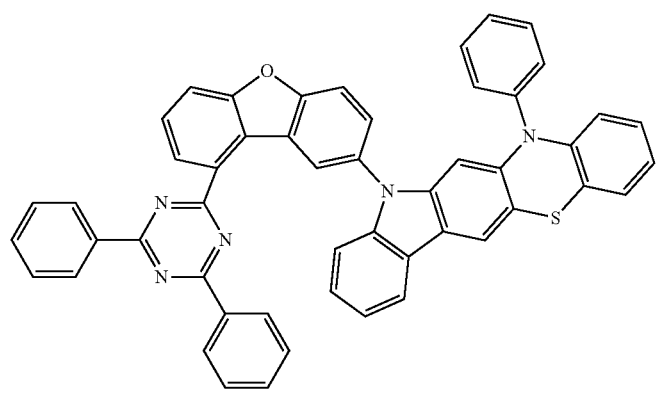
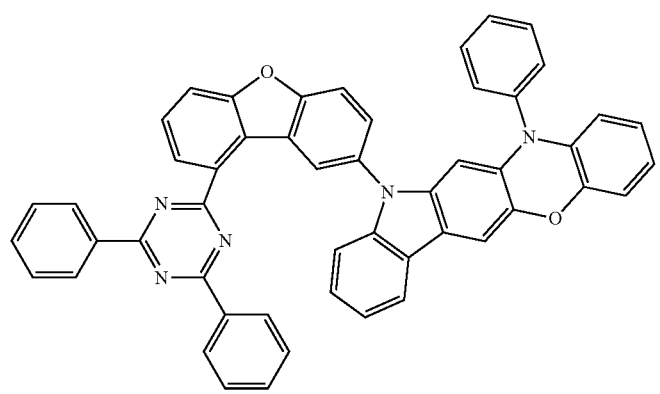

-continued
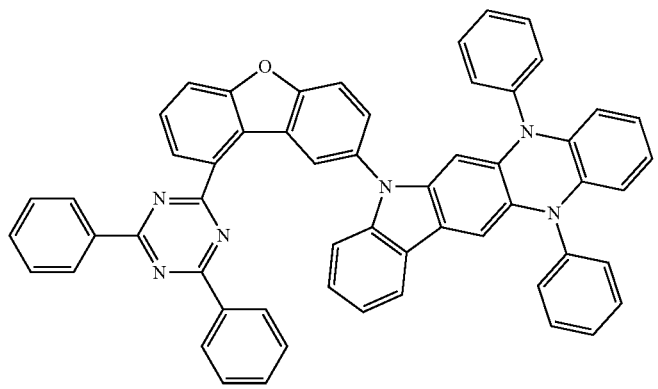
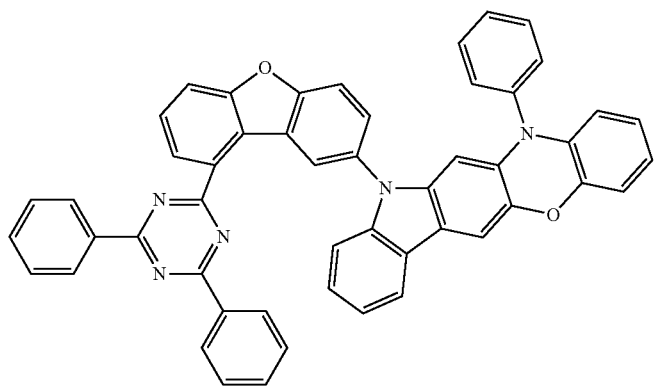
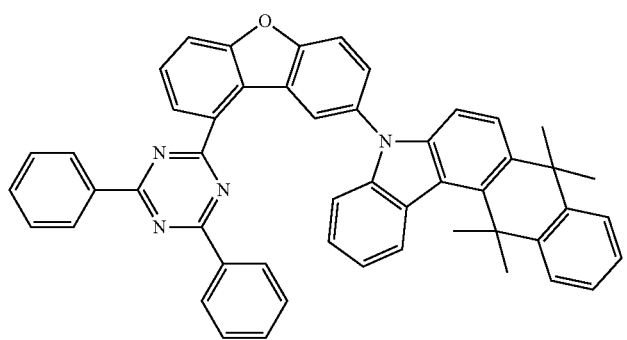
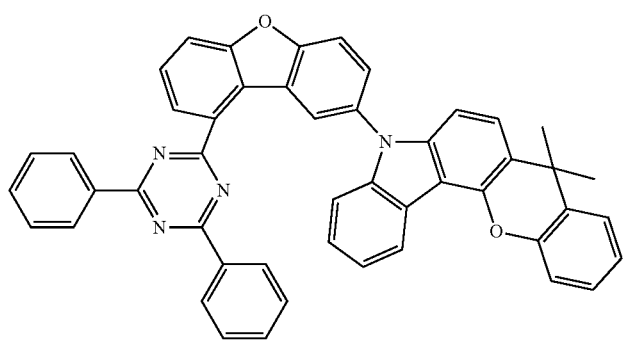

-continued
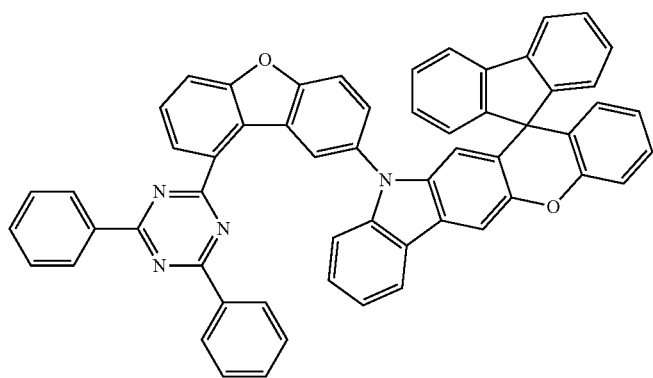
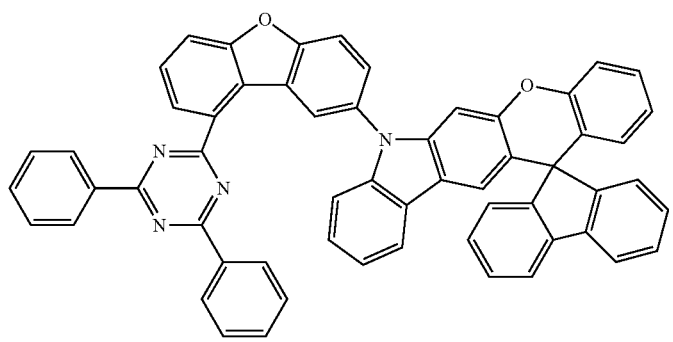
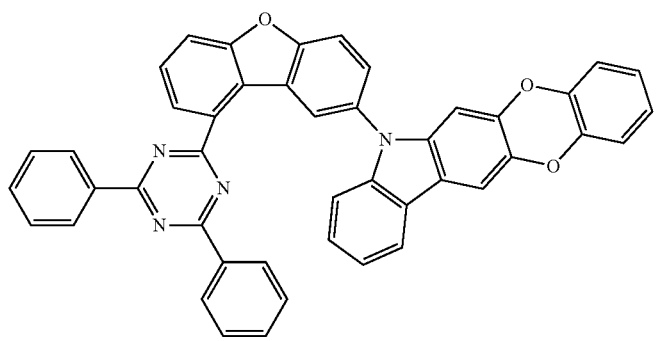
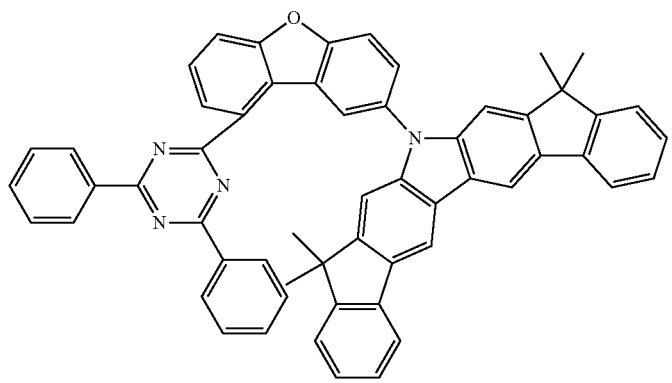

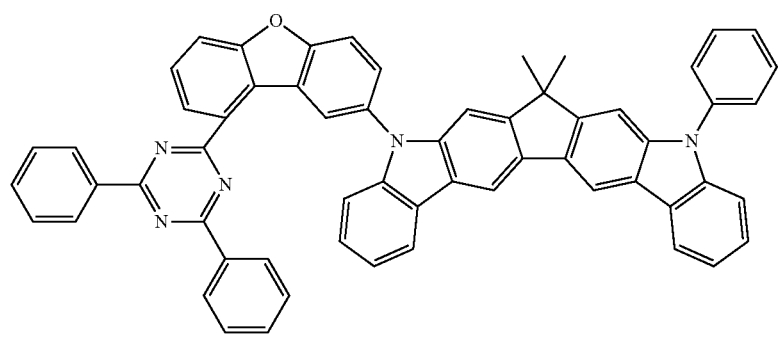
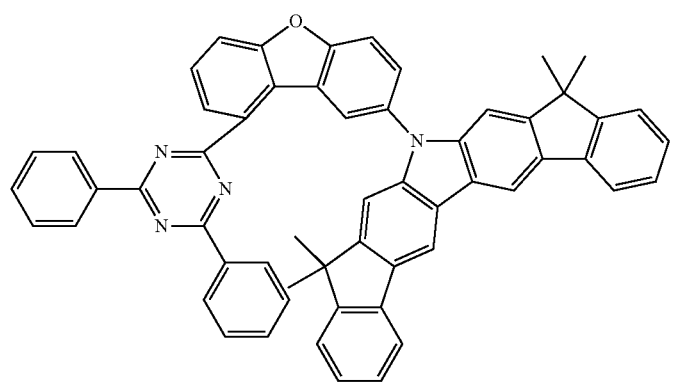
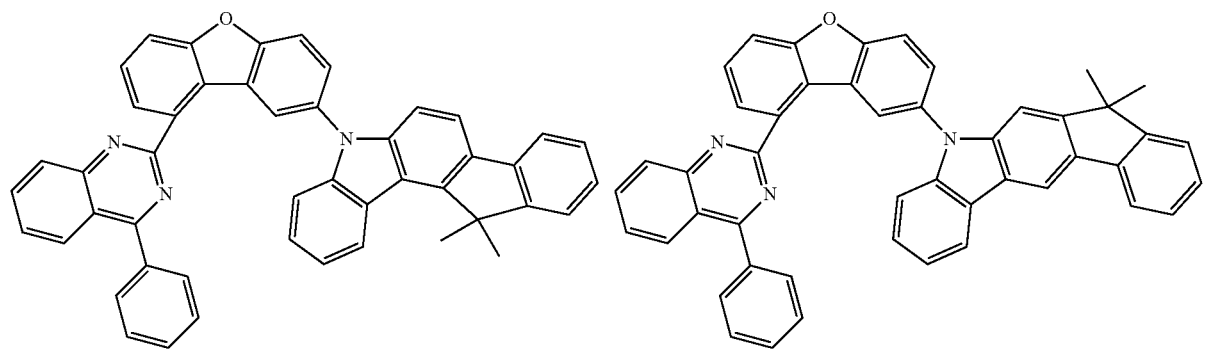
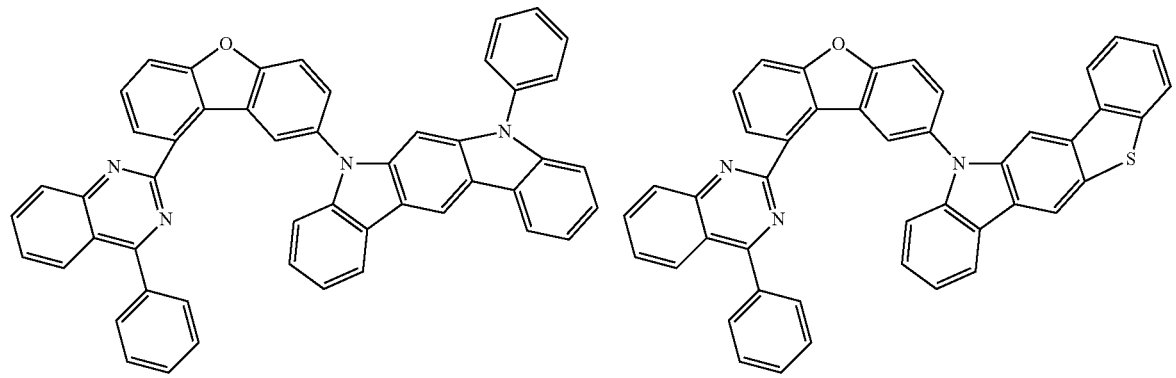

87
-continued
88
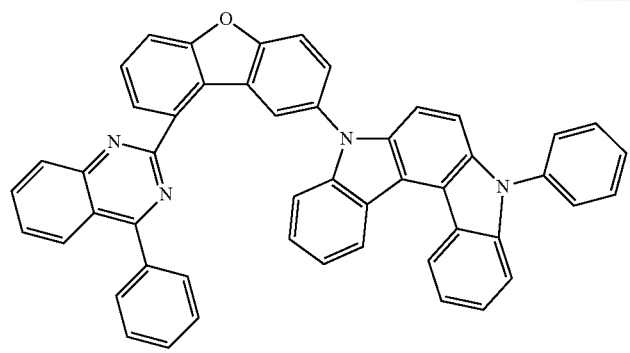
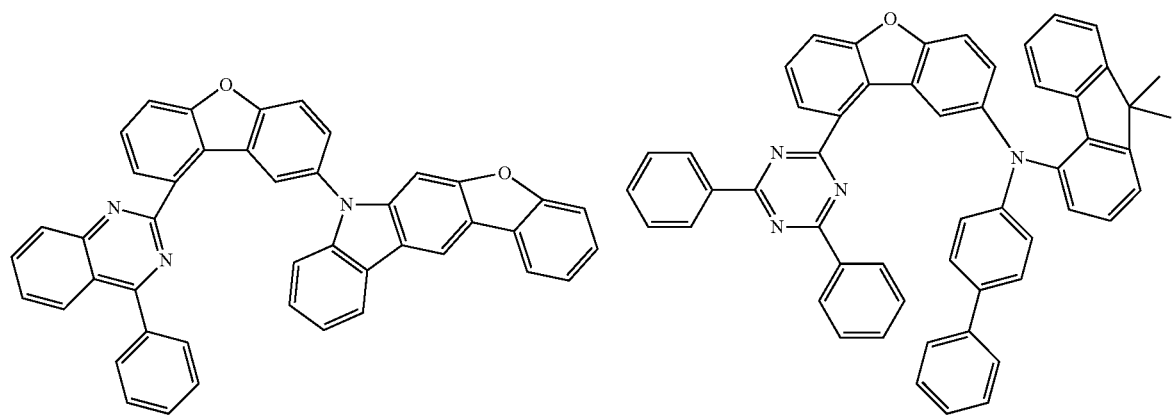
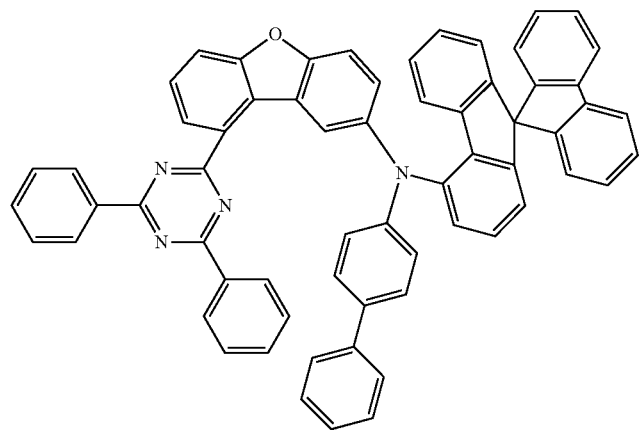
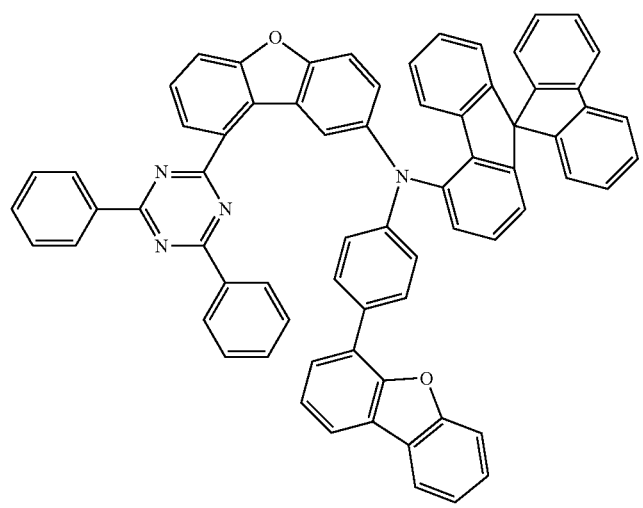
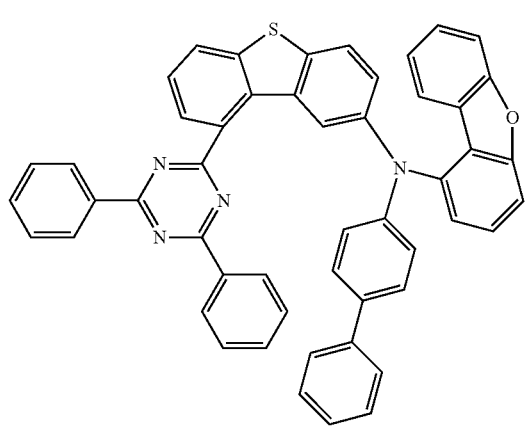

-continued
89
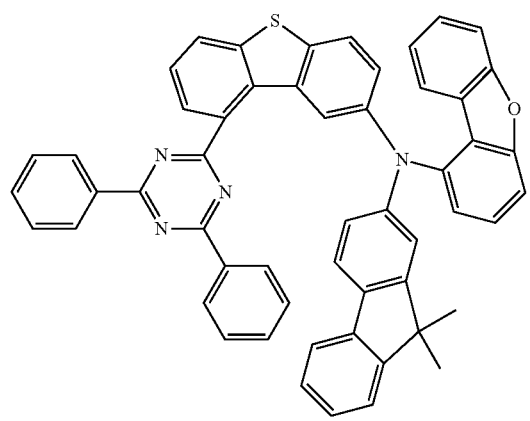
90
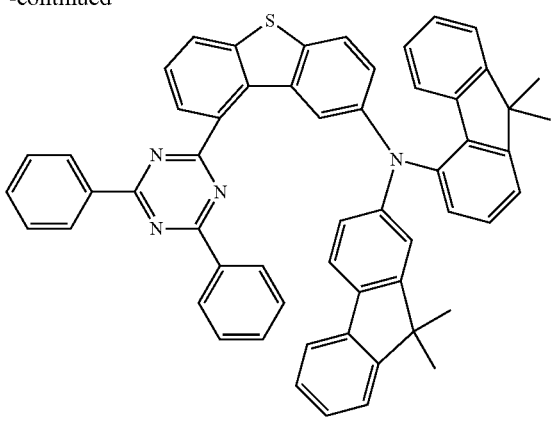
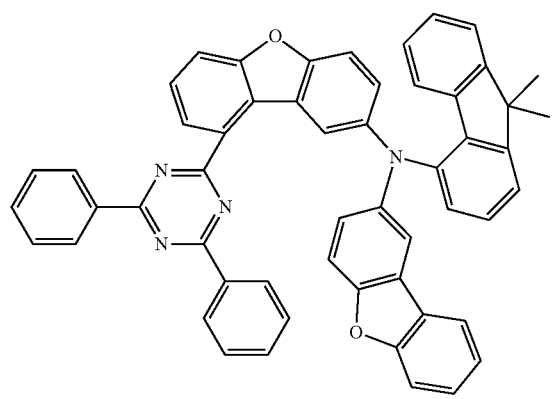
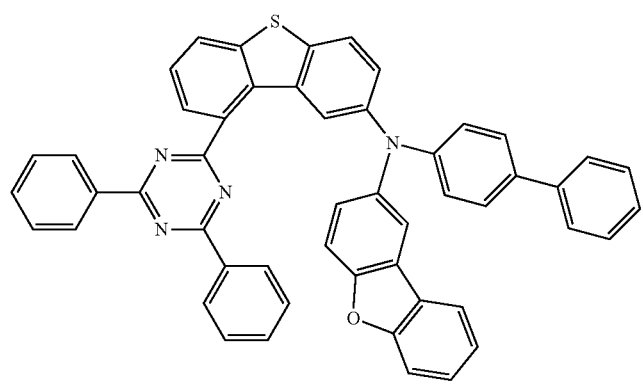
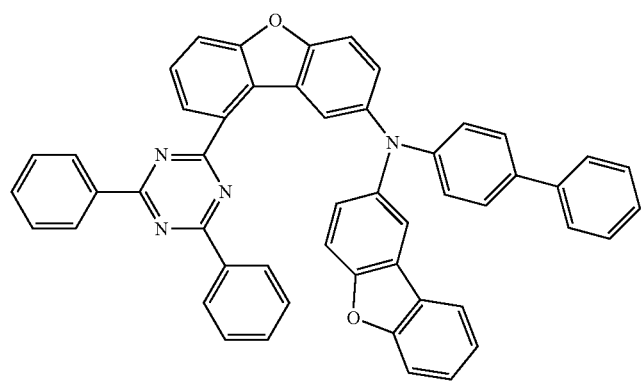

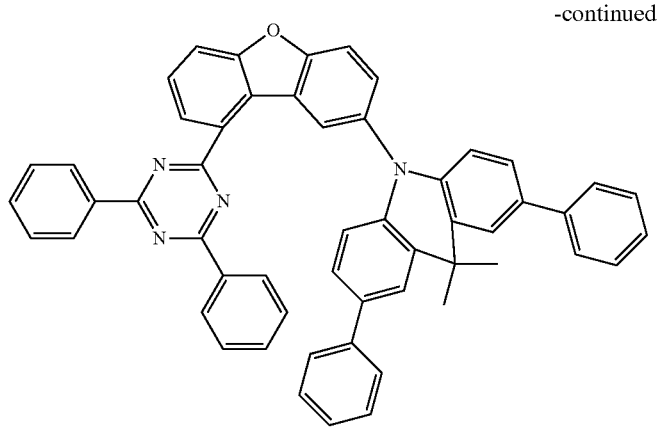
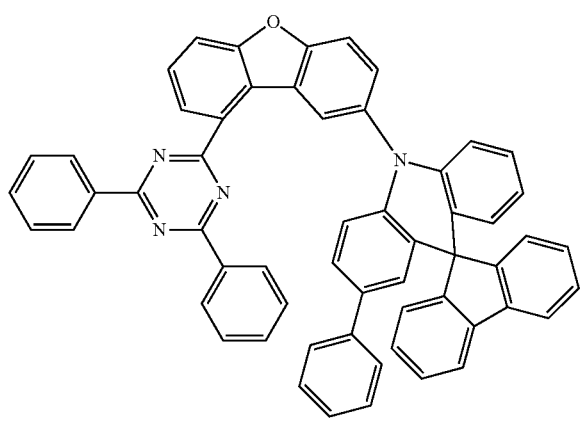
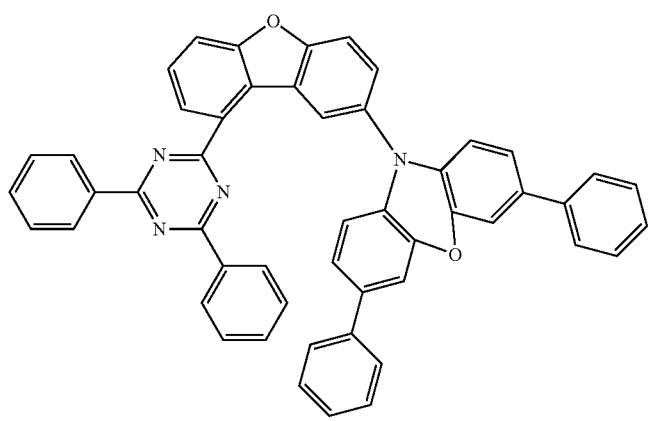
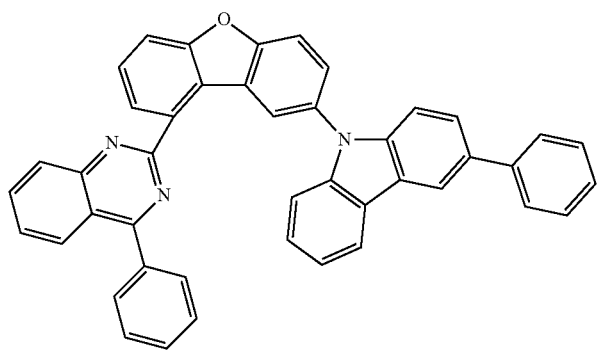

-continued
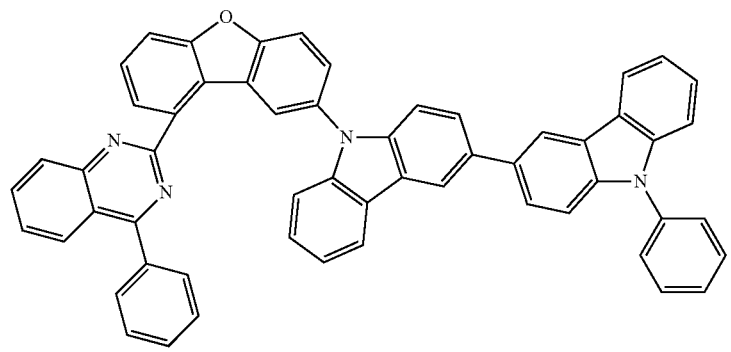
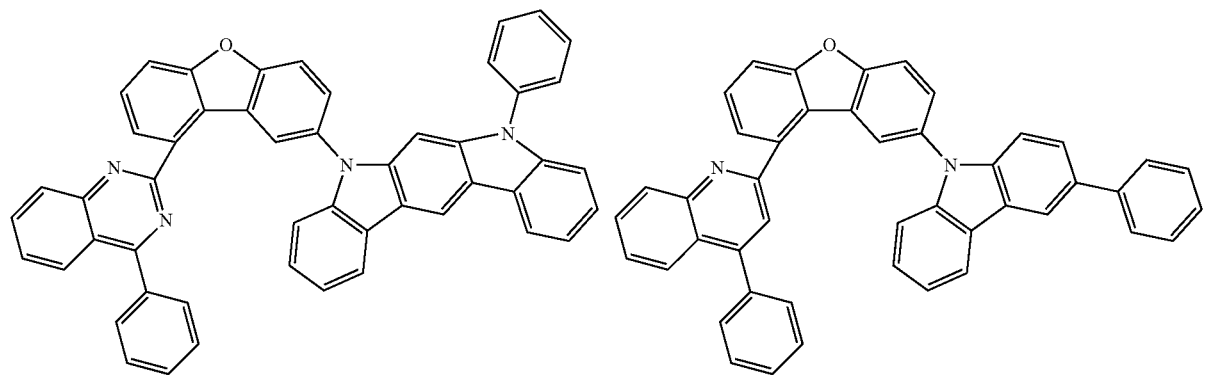
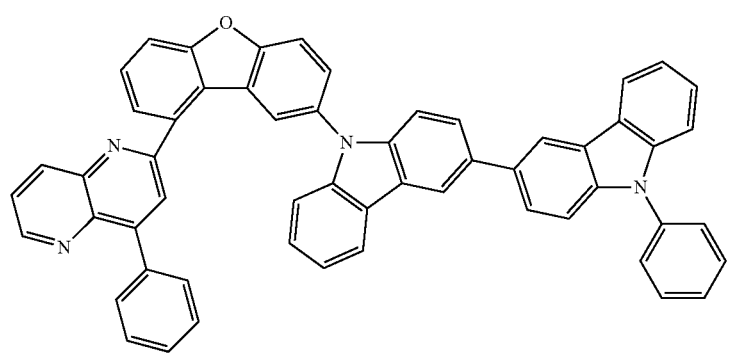
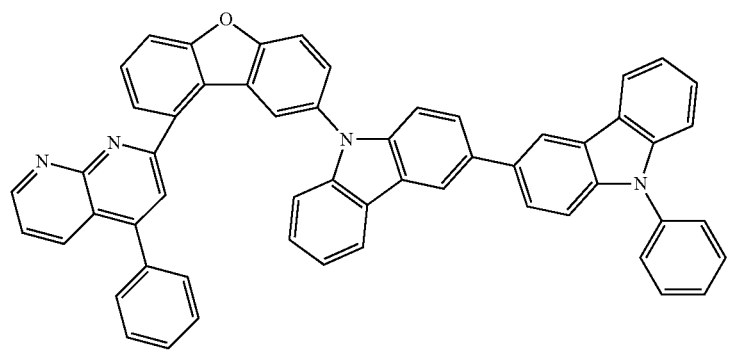

-continued
95 96
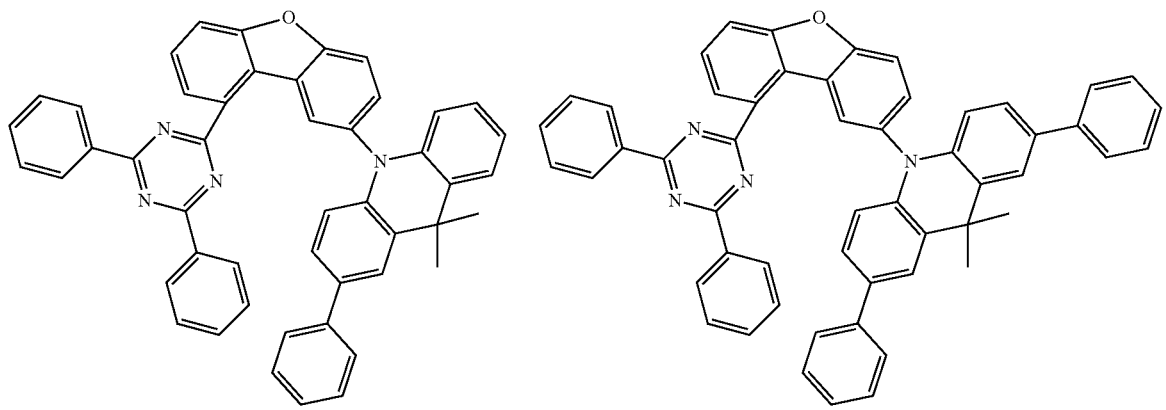
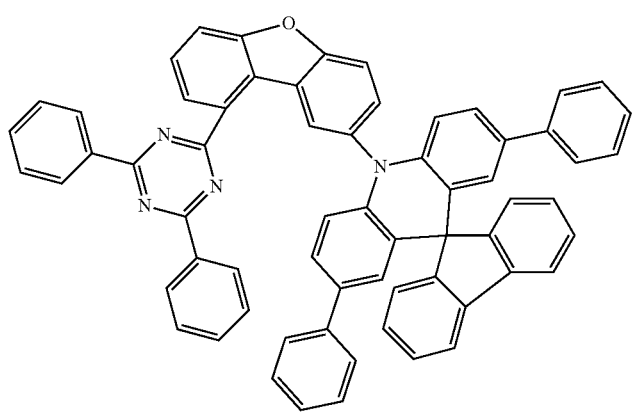
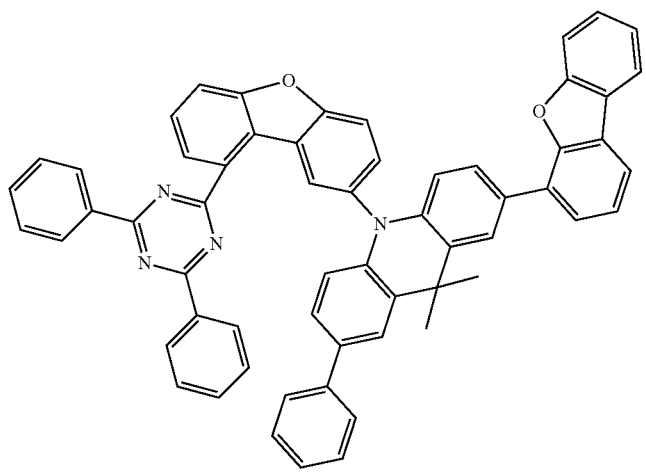

-continued
97 98
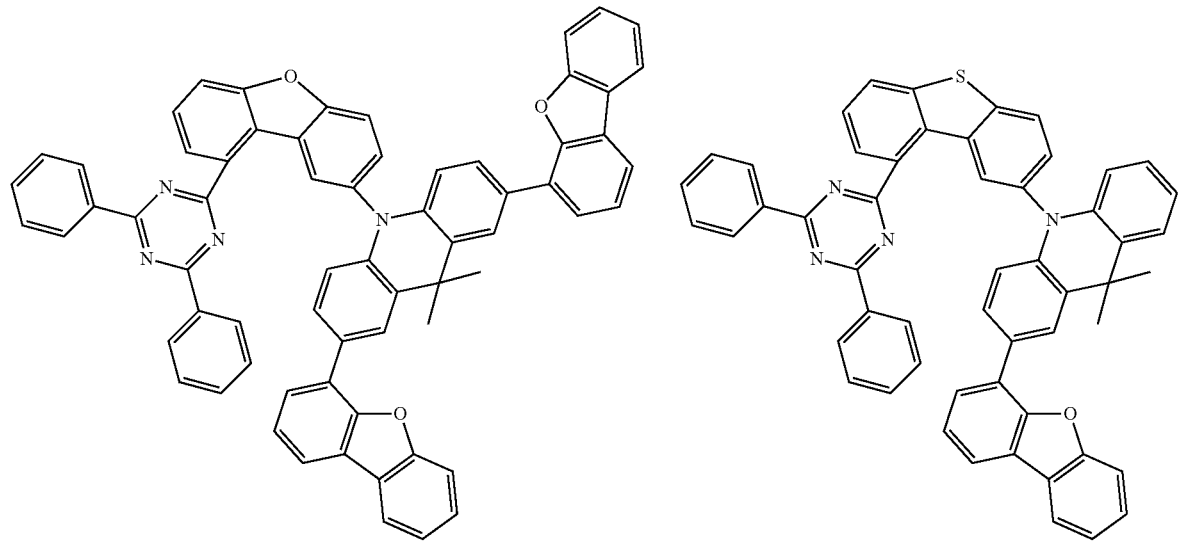
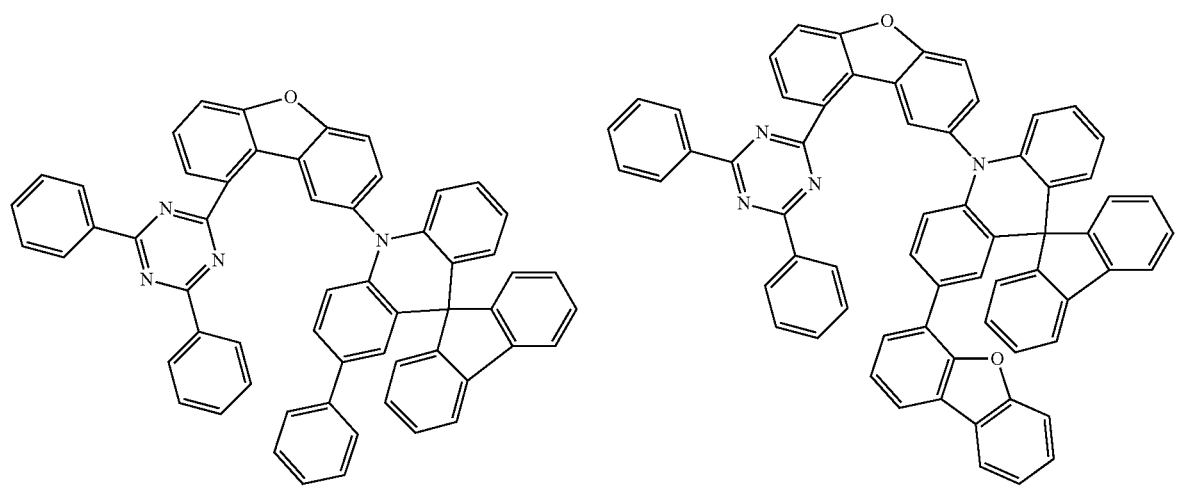
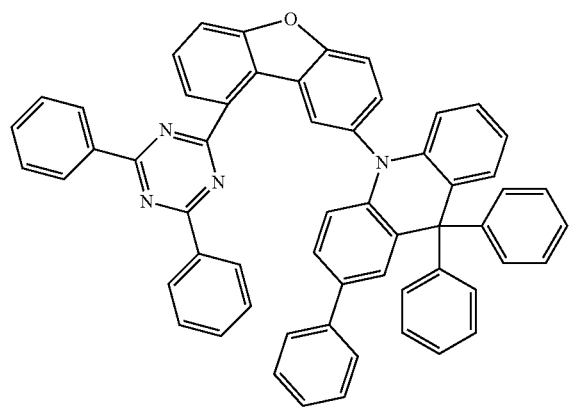

-continued
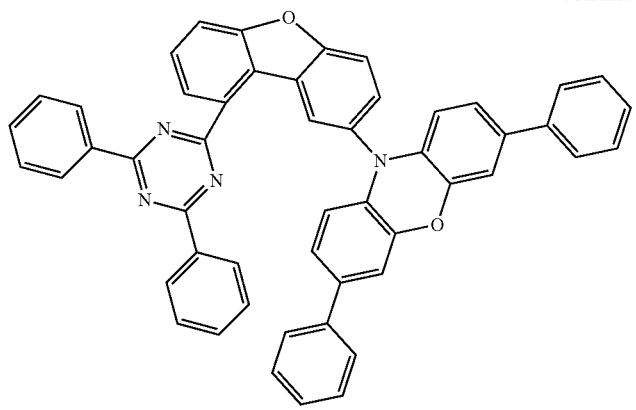
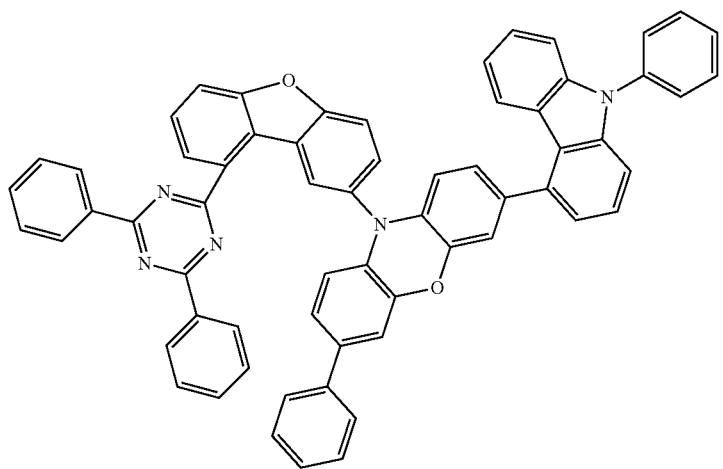
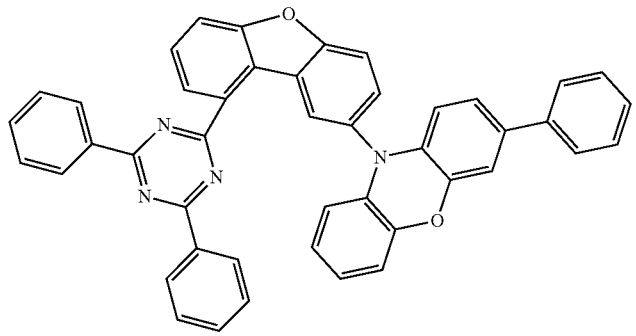
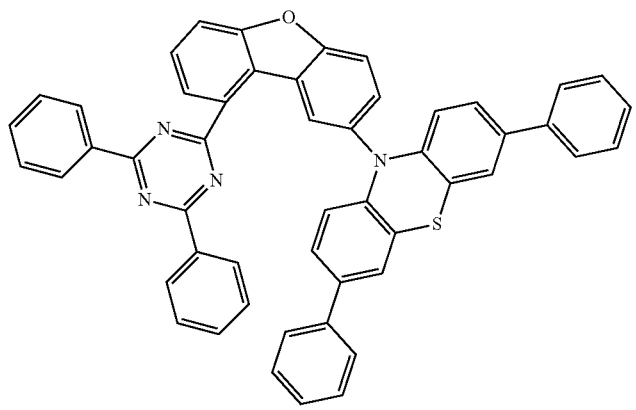

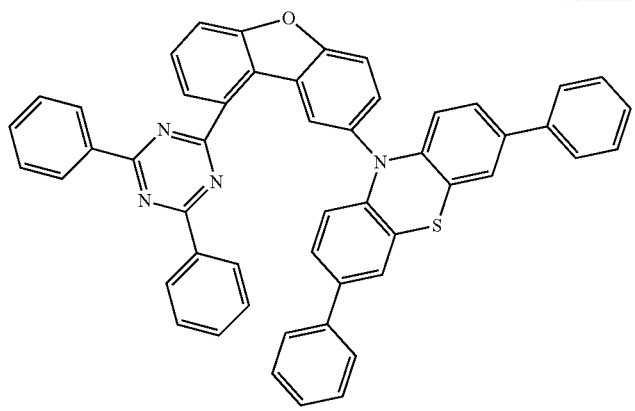
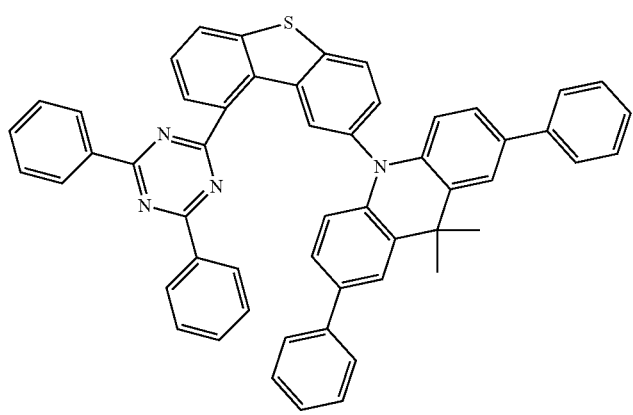
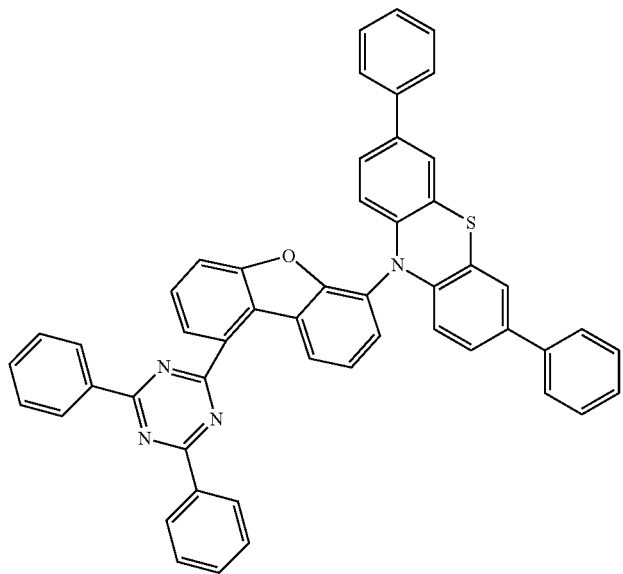

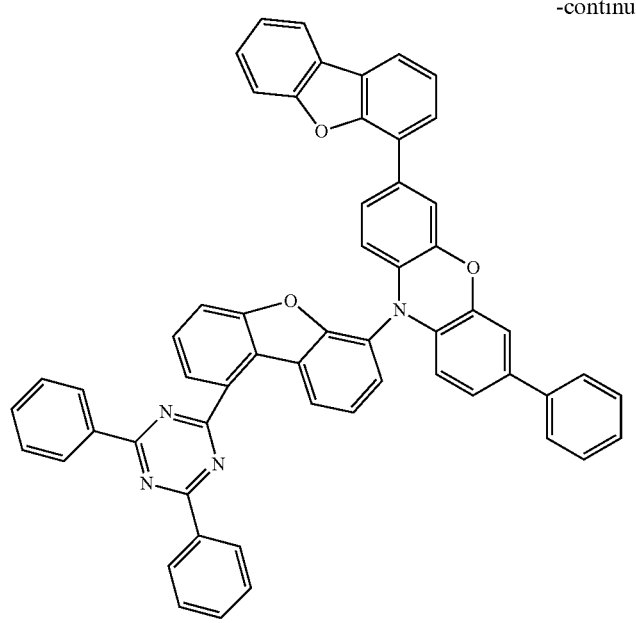
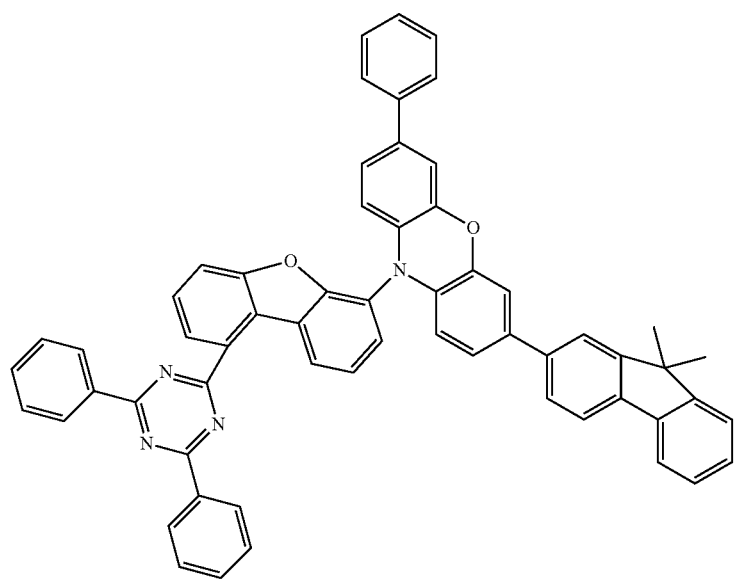
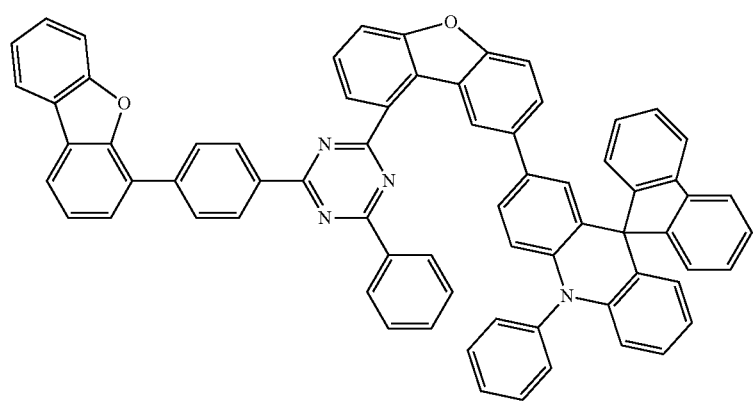

-continued

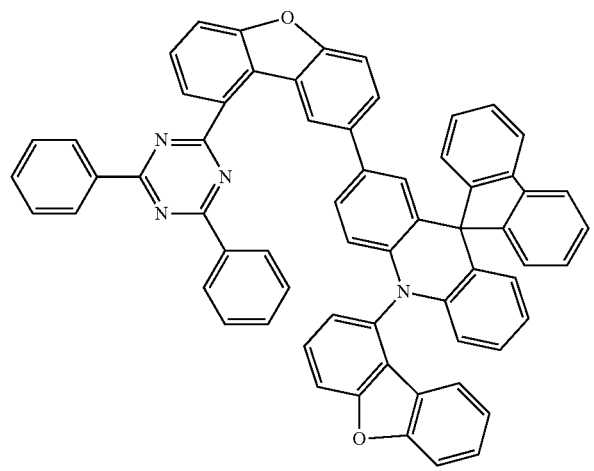

105

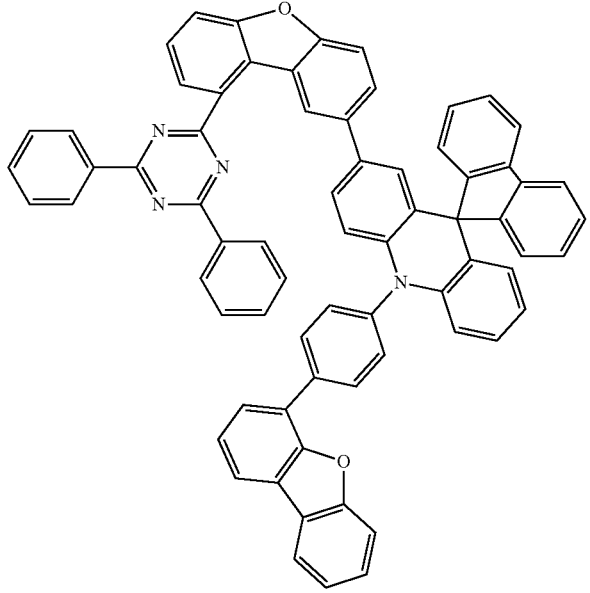

106

The compounds according to the invention can be prepared by synthesis steps known to the person skilled in the art, such as, for example, bromination, Suzuki coupling, Ullmann coupling, Hartwig-Buchwald coupling, etc. A suitable synthesis process is depicted in general terms in Scheme 1 below.

The synthesis starts from 1-halodibenzofuran or -dibenzothiophene, which is converted into the corresponding boronic acid or a boronic acid derivative. In the next step, the group HetAr can be introduced by Suzuki coupling. The halogenation, for example using NBS, takes place selectively in the 8-position of the dibenzofuran or dibenzothi- Scheme 1

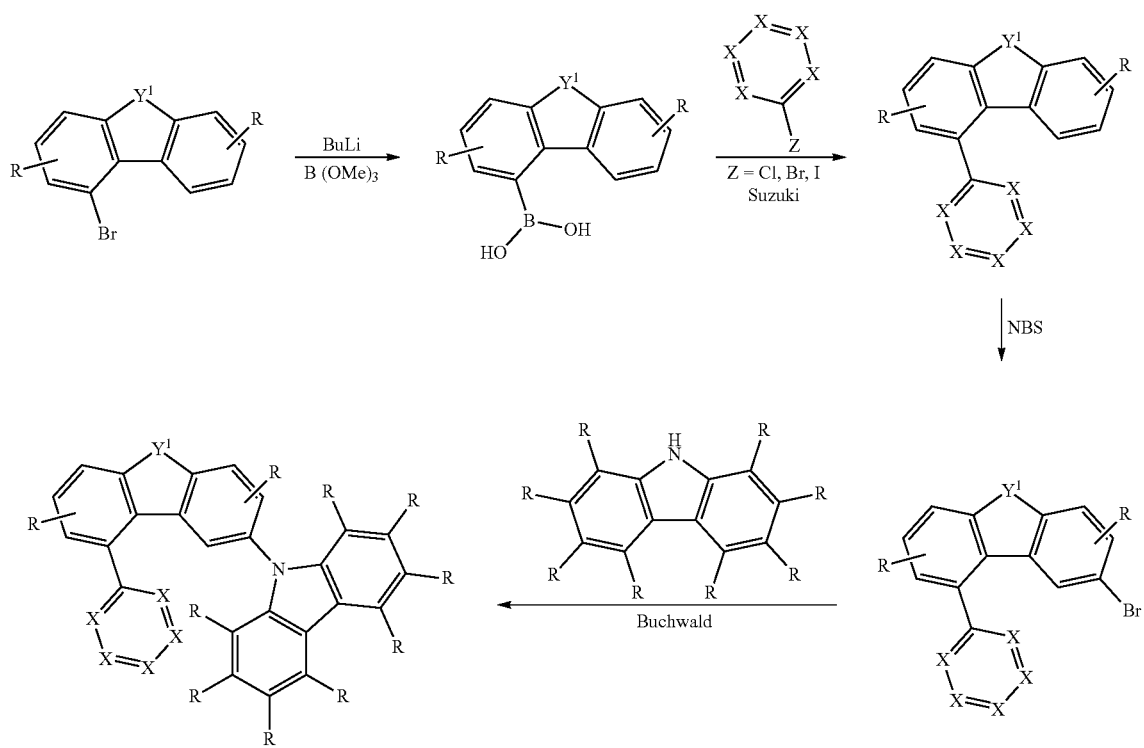

ophene. In the final step, the group $N^1$ can be introduced in this position, for example by a Hartwig-Buchwald coupling.

The general process shown for the synthesis of the compounds according to the invention is illustrative. The person skilled in the art will be able to develop alternative synthetic routes in the bounds of his general expert knowledge.

The present invention furthermore relates to a process for the synthesis of the compounds according to the invention, starting from 1-halodibenzofuran or 1-halodibenzothiophene, where the halogen is preferably bromine, characterised by the following steps:
(1) optionally conversion of the halogen group into a boronic acid or a boronic acid derivative;
(2) introduction of the group HetAr by a coupling reaction, in particular a Suzuki coupling;
(3) halogenation, in particular bromination, of the dibenzofuran or dibenzothiophene in the 8-position;
(4) introduction of the group $N^1$ by a coupling reaction, in particular a Hartwig-Buchwald coupling.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Preferred co-host materials are triarylamine derivatives, in particular monoamines, lactams, carbazole derivatives and indenocarbazole derivatives.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961 or WO 2014/094960. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-blocking or electron-transport layer. This applies, in particular, to compounds according to the invention which do not have a carbazole structure. These may preferably also be substituted by one or more further electron-transporting groups, for example benzimidazole groups.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or in accordance with the preferred embodiments.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention generally have very good properties on use in organic electroluminescent devices. In particular, the lifetime on use of the compounds according to the invention in organic electroluminescent devices is significantly better compared with similar compounds in accordance with the prior art. The other properties of the organic electroluminescent device, in particular the efficiency and the voltage, are likewise better or at least comparable. Furthermore, the compounds have a high glass transition temperature and high thermal stability.

The invention will now be explained in greater detail by the following examples, without wishing to restrict it thereby.

EXAMPLES

The following syntheses are carried out, unless indicated otherwise, under a protective-gas atmosphere in dried solvents. The solvents and reagents can be purchased, for example, from Sigma-ALDRICH or ABCR. The corresponding CAS numbers are also indicated in each case from the compounds known from the literature.

a) Synthesis of 6-bromo-2-fluoro-2'-methoxybiphenyl

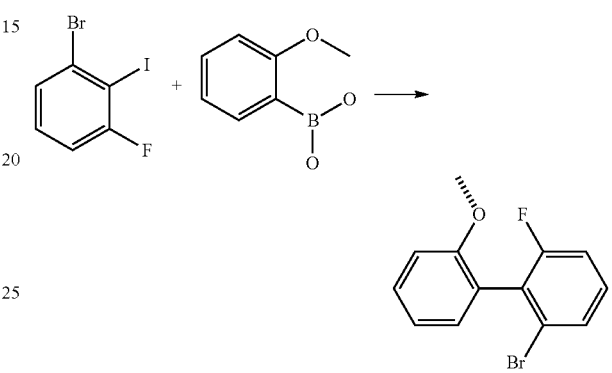

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water and degassed. 9.3 g (13.3 mmol) of bis(triphenylphosphine)palladium(II) chloride and 1 g (20 mmol) of hydrazinium hydroxide are added. The reaction mixture is subsequently stirred at 70° C. under a protective-gas atmosphere for 48 h. The cooled solution is replenished with toluene, washed a number of times with water, dried and evaporated. The product is purified by column chromatography on silica gel with toluene/heptane (1:2). Yield: 155 g (553 mmol), 83% of theory.

The following compounds are prepared analogously:

| | Starting material 1 | Starting material 2 | Product | Yield |
|---|---|---|---|---|
| a1 | 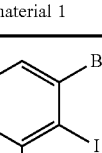 [1000576-09-9] | 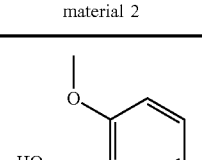 | 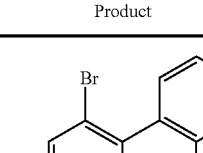 | 77% |
| a2 | 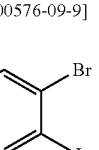 | 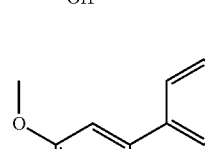 [1379680-54-2] | 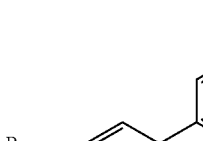 | 74% |

| | Starting material 1 | Starting material 2 | Product | Yield |
|---|---|---|---|---|
| a3 | (2-bromo-6-fluoro-1-iodobenzene) | [1199350-14-5] | | 76% |
| a4 | (2-bromo-6-fluoro-1-iodobenzene) | [1114496-44-4] | | 71% | b) Synthesis of 6'-bromo-2'-fluorobiphenyl-2-ol

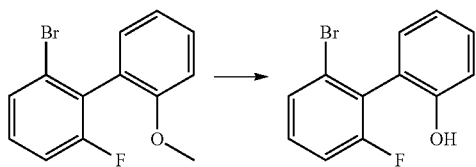 [SMILES: COc1ccccc1-c1c(F)cccc1Br ; Oc1ccccc1-c1c(F)cccc1Br]

112 g (418 mmol) of 6-bromo-2-fluoro-2'-methoxybiphenyl are dissolved in 2 l of dichloromethane and cooled to 5° C. 41.0 ml (431 mmol) of boron tribromide are added dropwise to this solution over the course of 90 min., and stirring is continued overnight. Water is slowly added to the mixture, and the organic phase is washed three times with water, dried over Na$_2$SO$_4$, evaporated in a rotary evaporator and purified by chromatography. Yield: 104 g (397 mmol), 98% of theory.

The following compounds are prepared analogously:

| | Starting material 1 | Product | Yield |
|---|---|---|---|
| b1 | | | 92% |
| b2 | | | 90% |

| | Starting material 1 | Product | Yield |
|---|---|---|---|
| b3 | ![b3 start] | ![b3 product] | 93% |
| b4 | ![b4 start] | ![b4 product] | 94% | c) Synthesis of 1-bromodibenzofuran

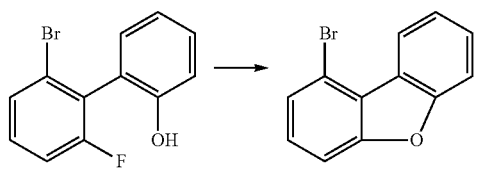 [SMILES: Oc1ccccc1-c1c(F)cccc1Br ; Brc1cccc2oc3ccccc3c12]

111 g (416 mmol) of 6'-bromo-2'-fluorobiphenyl-2-ol are dissolved in 2 l of SeccoSolv® DMF (max. 0.003% of $H_2O$) and cooled to 5° C. 20 g (449 mmol) of sodium hydride (60% suspension in paraffin oil) are added in portions to this solution, and the mixture is stirred for a further 20 min. after the addition is complete and then heated at 100° C. for 45 min. After cooling, 500 ml of ethanol are slowly added to the mixture, which is then evaporated to dryness in a rotary evaporator and purified by chromatography. Yield: 90 g (367 mmol), 88.5% of theory.

The following compounds are prepared analogously:

| | Starting material 1 | Product | Yield |
|---|---|---|---|
| c1 | ![c1 start] | ![c1 product] | 81% |
| c2 | ![c2 start] | ![c2 product] | 78% |

| | Starting material 1 | Product | Yield |
|---|---|---|---|
| c3 | (structure) | (structure) | 73% |
| c4 | (structure) | (structure) | 79% | d) Synthesis of dibenzofuran-1-boronic acid

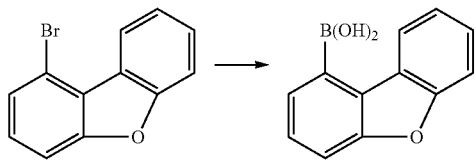 [SMILES: Brc1cccc2oc3ccccc3c12 ; OB(O)c1cccc2oc3ccccc3c12]

180 g (728 mmol) of 1-bromodibenzofuran are dissolved in 1500 ml of dry THF and cooled to −78° C. 305 ml (764 mmol/2.5 M in hexane) of n-butyllithium are added over the course of about 5 min. at this temperature, and stirring is subsequently continued at −78° C. for 2.5 h. 151 g (1456 mmol) of trimethyl borate are added as rapidly as possible at this temperature, and the reaction mixture is allowed to come slowly to room temperature (about 18 h). The reaction solution is washed with water, and the precipitated solid and the organic phase are dried azeotropically with toluene. The crude product is washed by stirring with toluene/methylene chloride at about 40° C. and filtered off with suction. Yield: 146 g (690 mmol), 95% of theory.

The following compounds are prepared analogously.

| | Starting material 1 | Product | Yield |
|---|---|---|---|
| d1 | (structure) | (structure) | 81% |
| d2 | (structure) | (structure) | 78% |

| | Starting material 1 | Product | Yield |
|---|---|---|---|
| d3 | 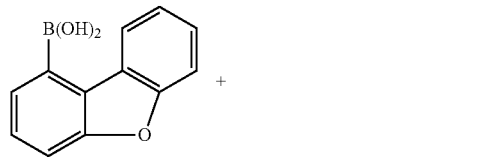 | | 73% |
| d4 | [65642-94-6] | | 73% | e) Synthesis of 2-chloro-4-dibenzofuran-1-yl-6-phenyl-1,3,5-triazine

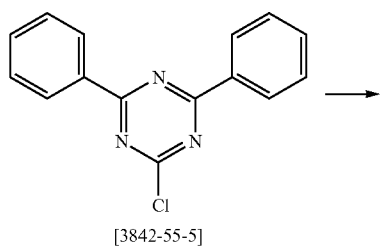 +

[3842-55-5]

→

-continued

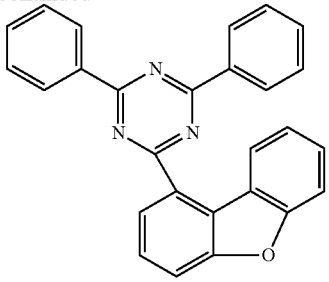

23 g (110.0 mmol) of dibenzofuran-1-boronic acid, 29.5 g (110.0 mmol) of 2-chloro-4,6-diphenyl-1,3,5-triazine and 21 g (210.0 mmol) of sodium carbonate are suspended in 500 ml of ethylene glycol diamine ether and 500 ml of water. 913 mg (3.0 mmol) of tri-o-tolylphosphine and then 112 mg (0.5 mmol) of palladium(ii) acetate are added to this suspension, and the reaction mixture is heated under reflux for 16 h. After cooling, the organic phase is separated off, filtered through silica gel, washed three times with 200 ml of water each time and subsequently evaporated to dryness. The residue is recrystallised from toluene and from dichloromethane/heptane. The yield is 37 g (94 mmol), corresponding to 87% of theory.

The following compounds are prepared analogously:

| | Starting material 1 | Starting material 2 | Product | Yield |
|---|---|---|---|---|
| e1 | 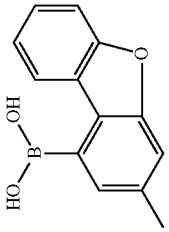 | 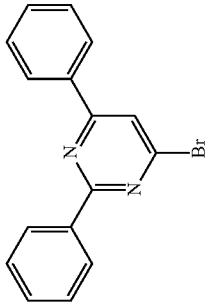[40734-24-5] | 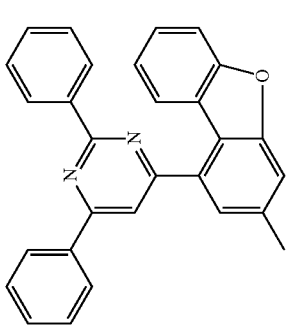 | 73% |
| e2 | 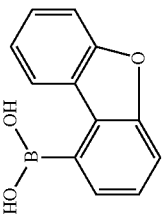 | 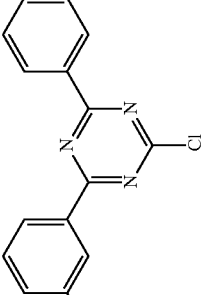 | 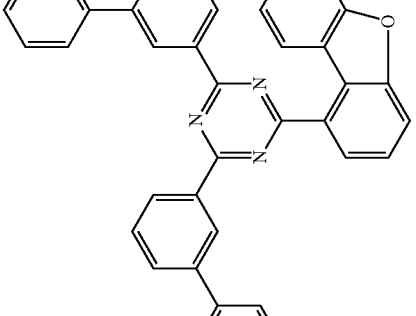 | 82% |
| e3 | 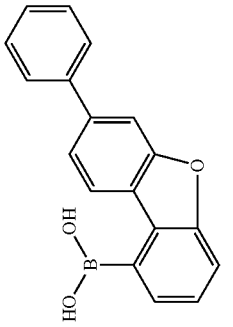 | 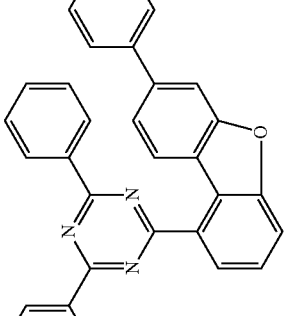[3842-55-5] | | 73% |

-continued

| Starting material 1 | Starting material 2 | Product | Yield |
|---|---|---|---|
| e4 | [40734-4-5] | | 72% |
| e5 | | | 63% |
| e6 [1434286-69-7] | | | 76% | f) Synthesis of 2-(8-bromodibenzofuran-1-yl)-4,6-diphenyl-1,3,5-triazine

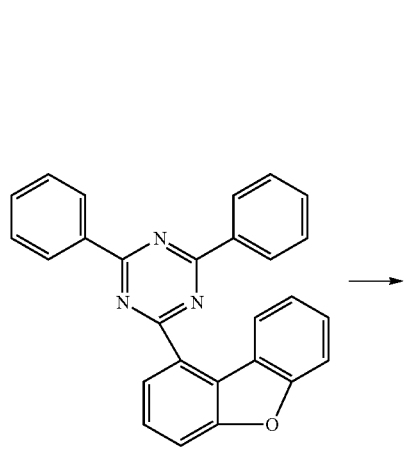

→

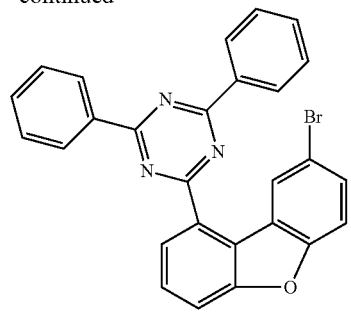

70 g (190.0 mmol) of 2-dibenzofuran-1-yl-4,6-diphenyl-1,3,5-triazine are suspended in 2000 ml of aceetic acid (100%) and 2000 ml of sulfuric acid (95-98%). 34 g (190 mmol) of NBS are added to this suspension in portions, and the mixture is stirred in the dark for 2 h. Water/ice is then added, and the solid is separated off and rinsed with ethanol. The residue is recrystallised from toluene. The yield is 80 g (167 mmol), corresponding to 87% of theory.

The following compounds are prepared analogously.

| | Starting material 1 | Product | Yield |
|---|---|---|---|
| f1 | 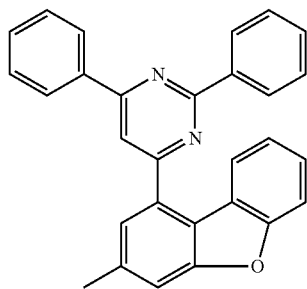 [SMILES: Cc1cc(-c2cc(-c3ccccc3)nc(-c3ccccc3)n2)c2c(c1)oc1ccccc12] | 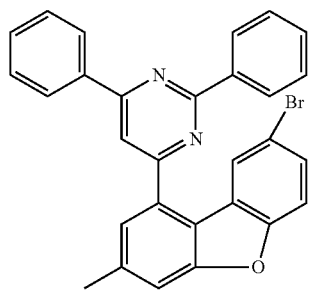 [SMILES: Cc1cc(-c2cc(-c3ccccc3)nc(-c3ccccc3)n2)c2c(c1)oc1ccc(Br)cc12] | 80% |
| f2 | 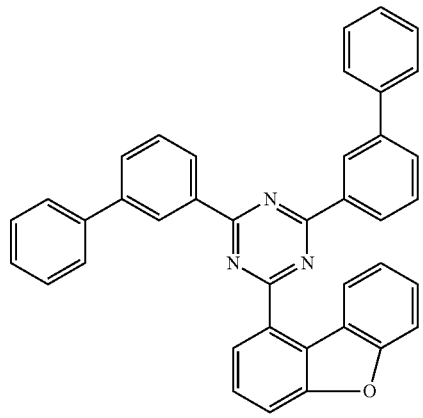 [SMILES: c1ccc(-c2cccc(-c3nc(-c4cccc(-c5ccccc5)c4)nc(-c4cccc5oc6ccccc6c45)n3)c2)cc1] | 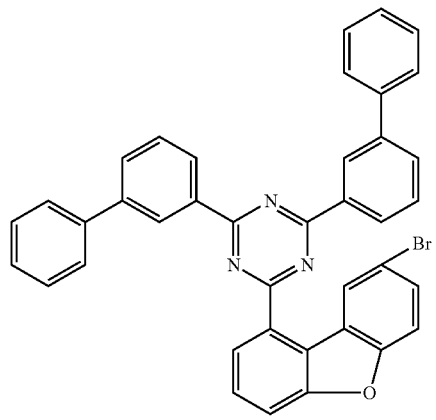 [SMILES: Brc1ccc2oc3cccc(-c4nc(-c5cccc(-c6ccccc6)c5)nc(-c5cccc(-c6ccccc6)c5)n4)c3c2c1] | 41% |

-continued

| | Starting material 1 | Product | Yield |
|---|---|---|---|
| f3 | | | 52% |
| f4 | | | 64% |

In the case of thiophene derivatives, nitrobenzene is employed instead of sulfuric acid and elemental bromine is employed instead of NBS:

| | | | |
|---|---|---|---|
| f5 | | | 55% |
| f6 | | | 52% | g) Synthesis of 9-[9-(4,6-diphenyl-1,3,5-triazin-2-yl)dibenzofuran-2-yl]-3-phenyl-9H-carbazole

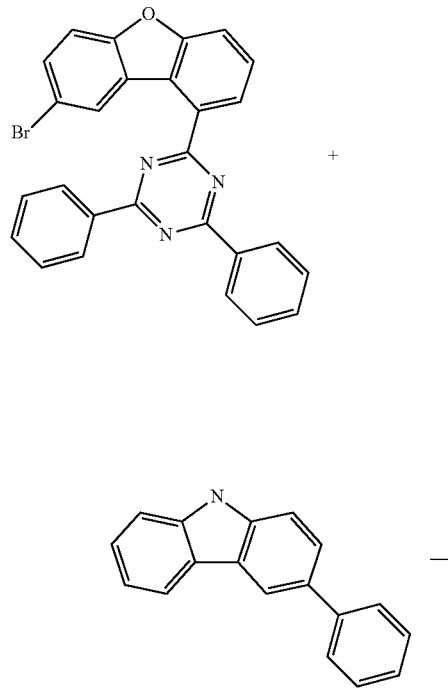

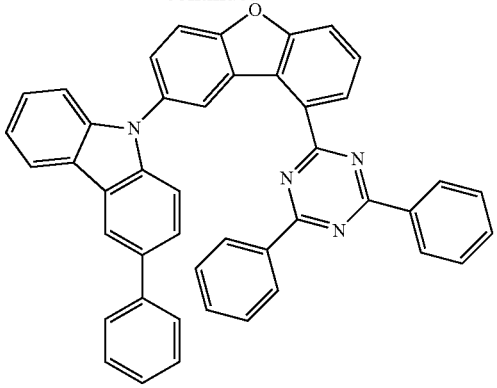

A degassed solution of 70 g (147 mmol) of 2-(8-bromodibenzofuran-1-yl)-4,6-diphenyl-1,3,5-triazine and 35.7 g (147 mmol) of 3-phenyl-9H-carbazole in 600 ml of toluene is saturated with $N_2$ for 1 h. Firstly 2.09 ml (8.6 mmol) of P(tBu)$_3$, then 1.38 g (6.1 mmol) of plladium(II) acetate are added to the solution, and 17.7 g (185 mmol) of NaOtBu in the solid state are subsequently added. The reaction mixture is heated under reflux for 1 h. After cooling to room temperature, the mixture is washed with 3×50 ml of toluene, dried over MgSO$_4$, and the solvent is removed in vacuo. The cruse product is purified by chromatography on silica gel with heptane/ethyl acetate (20/1). The residue is recrystallised from toluene and finally sublimed in a high vacuum (p=5×10$^{-6}$ mbar). The yield is 74.8 g (116 mmol), corresponding to 80% of theory.

The following compounds are prepared analogously:

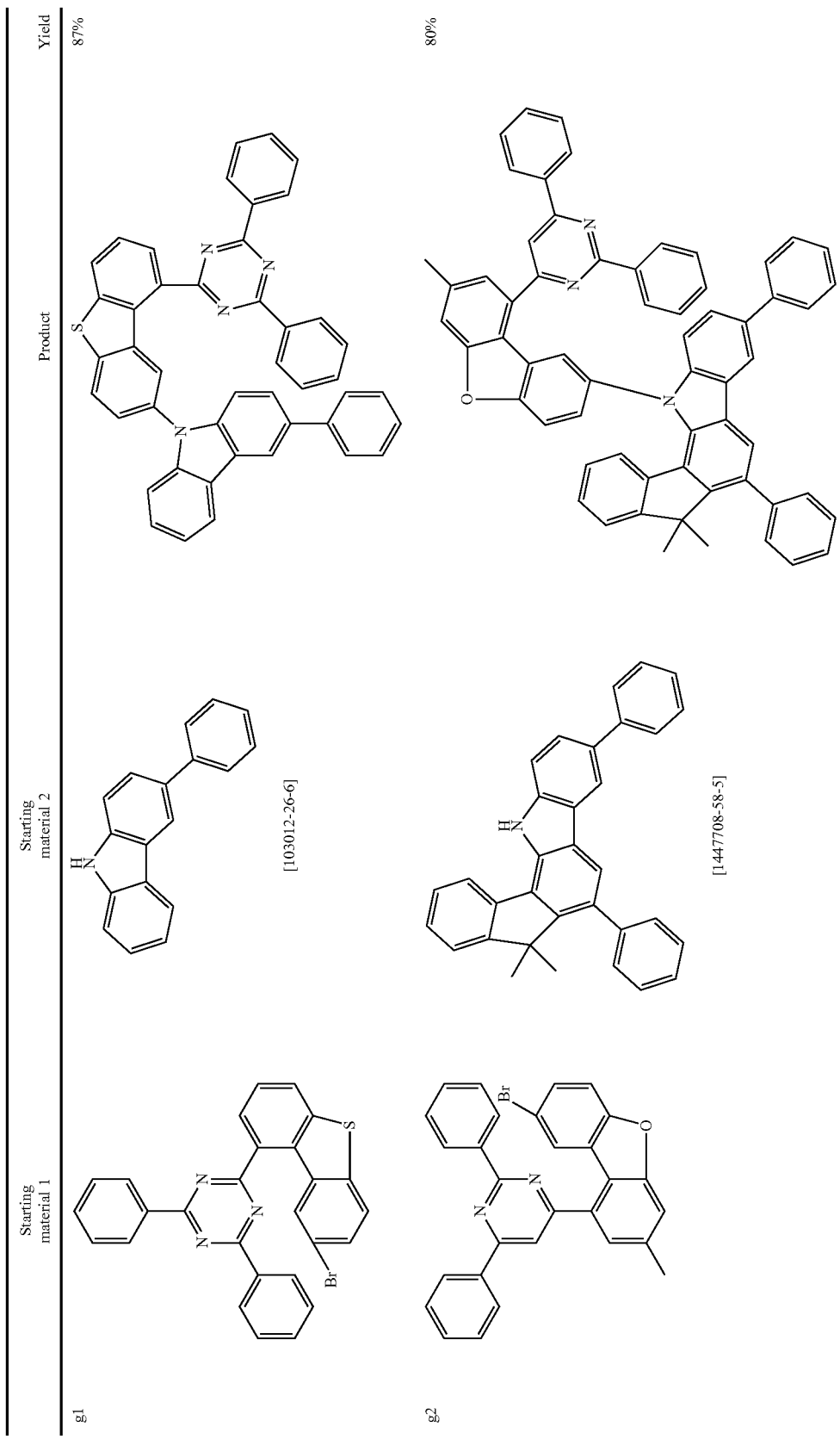

| | Starting material 1 | Starting material 2 | Product | Yield |
|---|---|---|---|---|
| g3 | 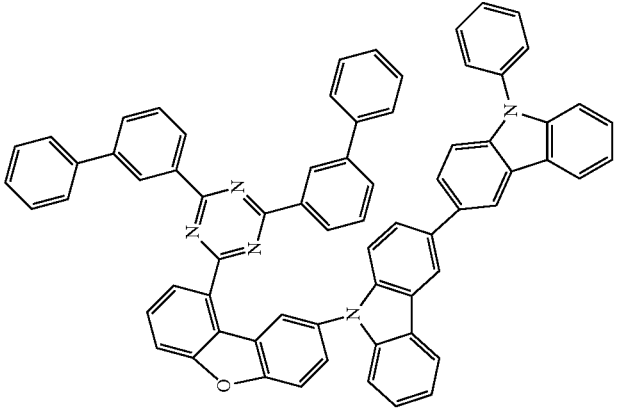 | 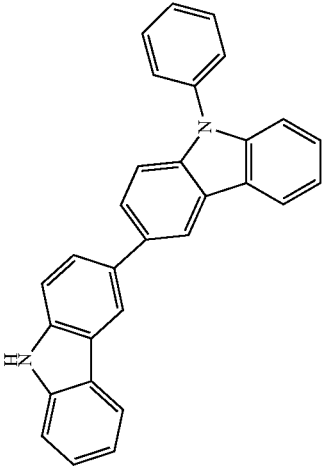 [1060735-14-9] | 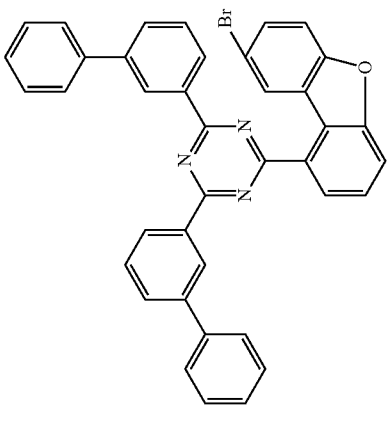 | 67% |

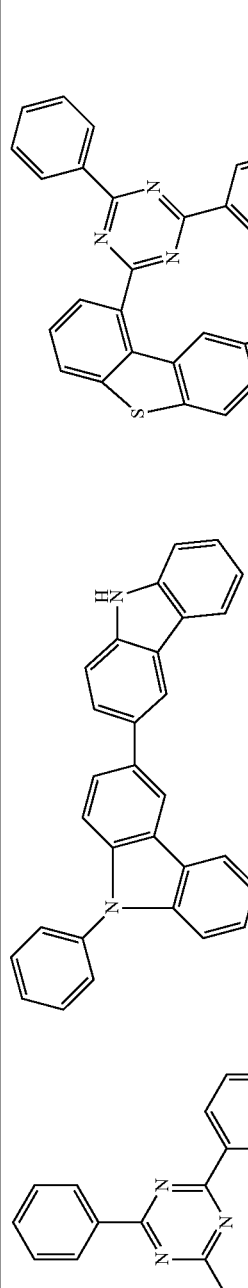

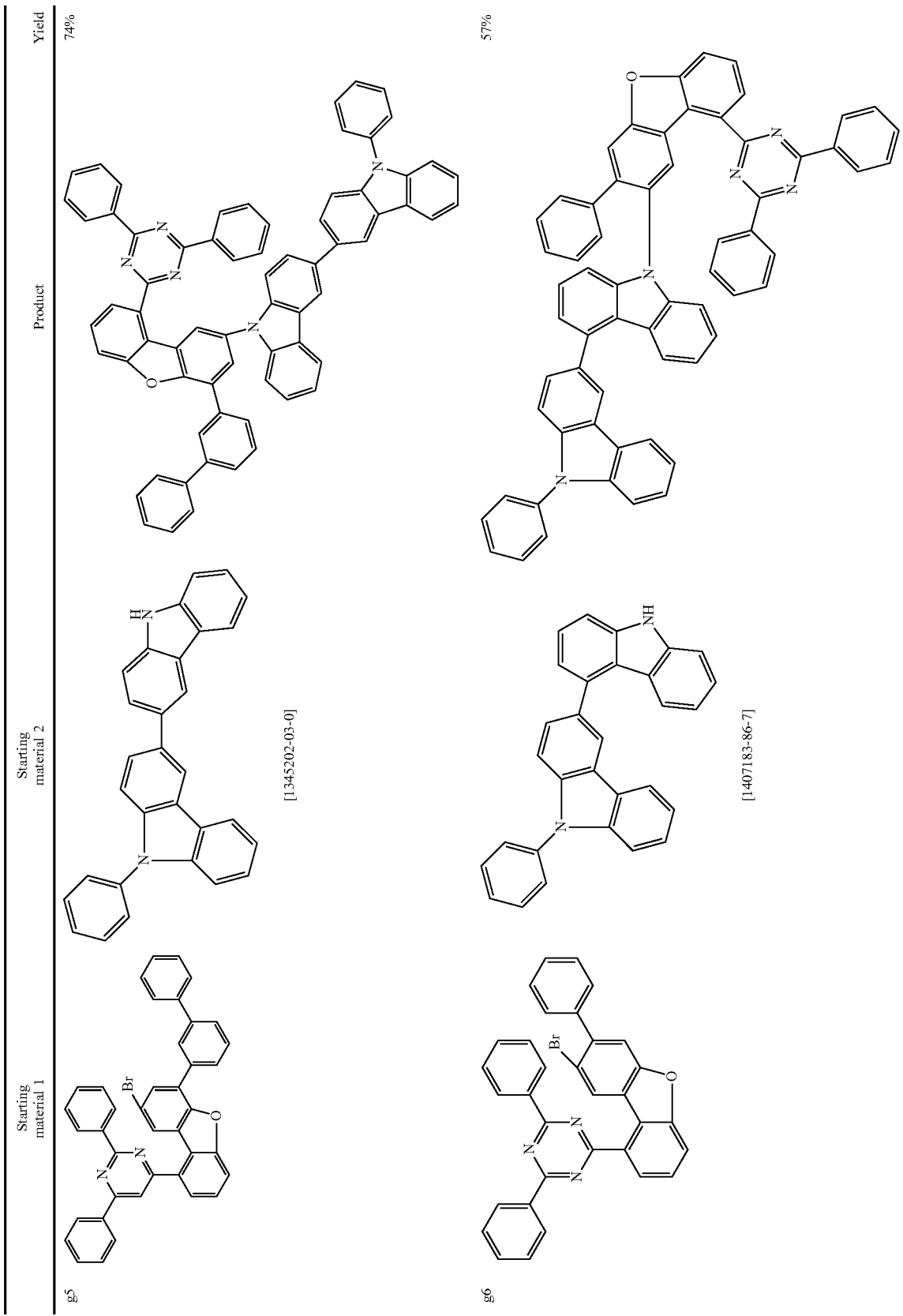

-continued

| Starting material 1 | Starting material 2 | Product | Yield |
|---|---|---|---|
| g7 | [1257220-47-5] | | 81% |
| g8 | [1257220-47-5] | | 83% |

| | Starting material 1 | Starting material 2 | Product | Yield |
|---|---|---|---|---|
| g9 | | [1024598-06-8] | | 87% |
| g10 | | [1024598-06-8] | | 80% |

-continued

| | Starting material 1 | Starting material 2 | Product | Yield |
|---|---|---|---|---|
| g11 | | [1338919-70-2] | | 81% |
| g12 | | [103012-26-6] | | 88% |

-continued
| | Starting material 1 | Starting material 2 | Product | Yield |
|---|---|---|---|---|
| g13 | 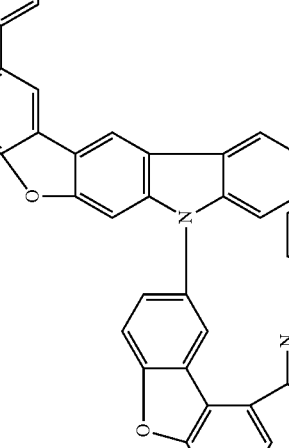 | 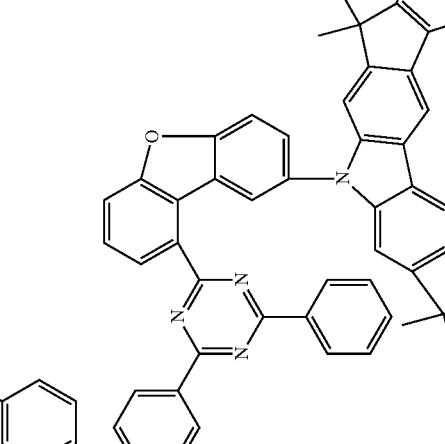 [1439927-96-4] | 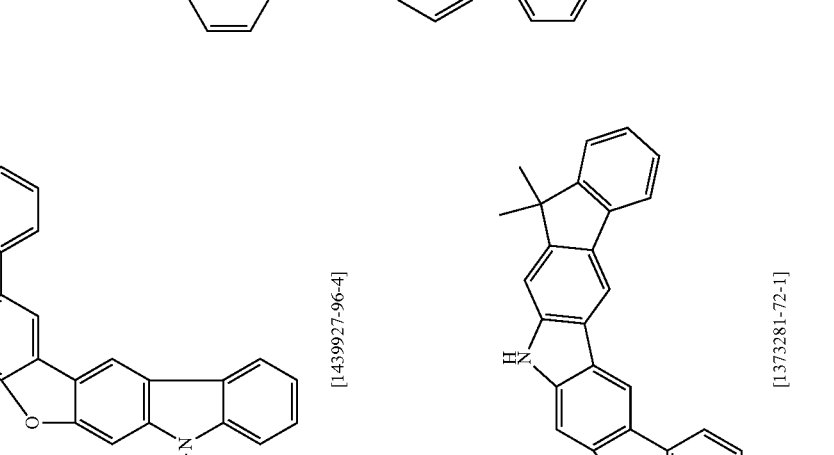 | 73% |
| g14 | 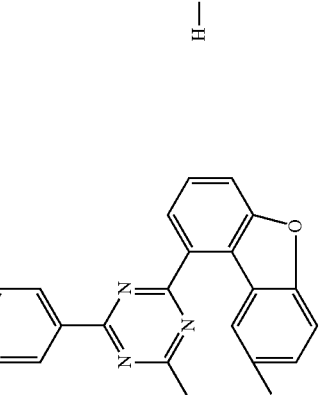 | 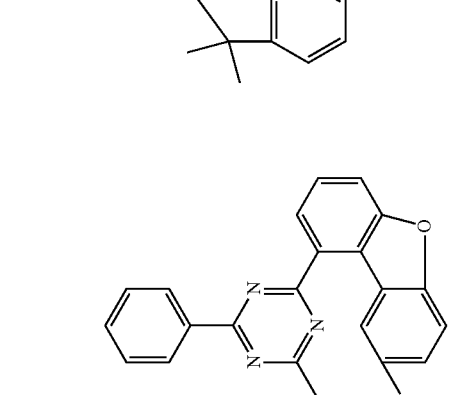 [1373281-72-1] |  | 79% |

-continued

| | Starting material 1 | Starting material 2 | Product | Yield |
|---|---|---|---|---|
| g15 | (structure with triazine, dibenzofuran, Br) | (structure [1316311-27-9]) | (product structure) | 84% |
| g16 | (structure with triazine, dibenzofuran, Br) | (structure [1260228-95-2]) | (product structure) | 59% |

| | Starting material 1 | Starting material 2 | Product | Yield |
|---|---|---|---|---|
| g17 | | [1199350-22-5] | | 62% |
| g18 | | [1257248-14-8] | | 72% |

| | Starting material 1 | Starting material 2 | Product | Yield |
|---|---|---|---|---|
| g19 | 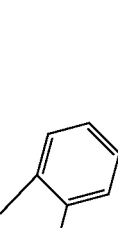 | 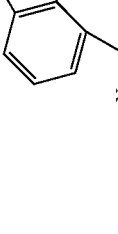
[1255309-04-6] | 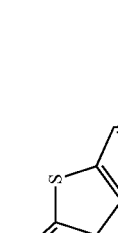 | 69% |
| g20 | 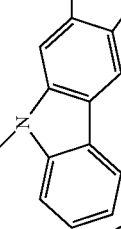 | 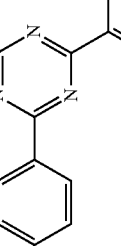
[1345202-03-0] | 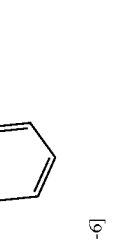 | 72% |

| Starting material 1 | Starting material 2 | Product | Yield |
|---|---|---|---|
| g21 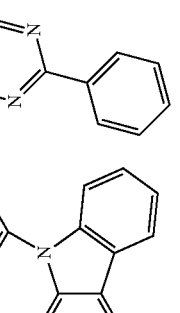 |  [1316311-27-9] | 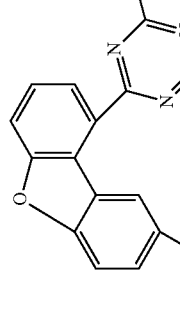 | 62% |
| g22 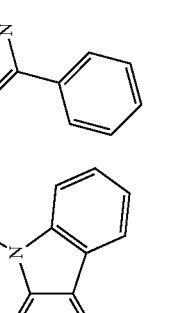 |  [1361126-04-6] | 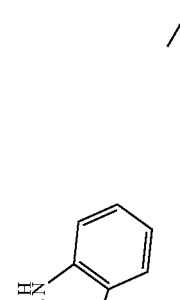 | 65% |

| | Starting material 1 | Starting material 2 | Product | Yield |
|---|---|---|---|---|
| g23 | | [1247053-55-9] | | 61% |
| g24 | | [1246308-90-6] | | 73% |

-continued

| | Starting material 1 | Starting material 2 | Product | Yield |
|---|---|---|---|---|
| g25 | (triazine-phenyl-dibenzofuran-Br) | (phenyl-carbazole fused pyridoindole, NH) | | 80% |
| g26 | (triazine-phenyl-dibenzofuran-Br) | (dimethyl-indeno-biscarbazole, [1246308-88-2] and [1257246-71-7]) | | 69% |

| | Starting material 1 | Starting material 2 | Product | Yield |
|---|---|---|---|---|
| g27 | | [1219841-59-4] | | 71% |
| g28 | | [1247053-55-9] | | 72% |

-continued

| | Starting material 1 | Starting material 2 | Product | Yield |
|---|---|---|---|---|
| g29 | (structure) | (structure) [1246308-85-9] | (structure) | 63% |
| g30 | (structure) | (structure) [1259280-39-1] | (structure) | 72% |

| | -continued | | |
|---|---|---|---|
| | Starting material 1 | Starting material 2 | Product | Yield |
| g31 | 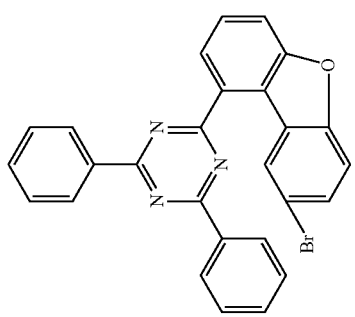 | 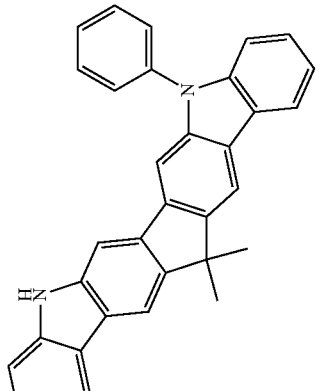 [1430889-64-1] | 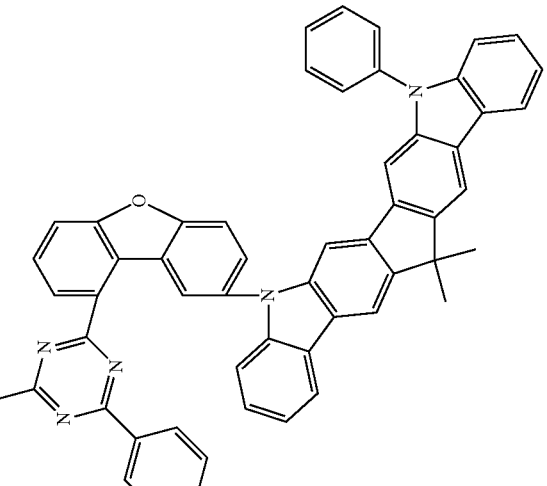 | 82% |

| | Starting material 1 | Starting material 2 | Product | Yield |
|---|---|---|---|---|
| g32 | (structure with triazine-diphenyl and dibenzofuran-Br) | (structure [1255308-97-4]) | (product structure) | 63% |

167 h) Biphenyl-4-yl-(9,9-dimethyl-9H-fluoren-2-yl) amine

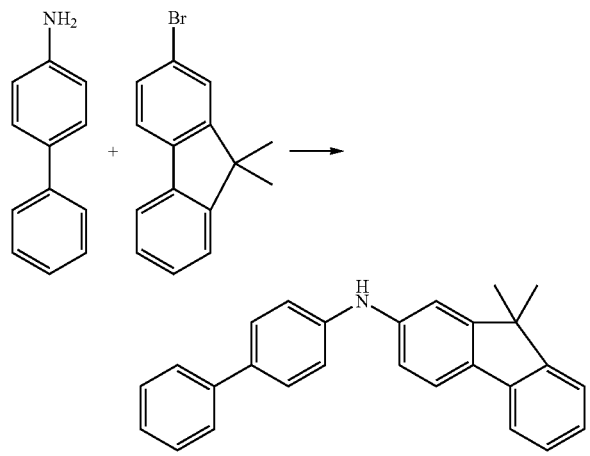

168

24.0 g (142 mmol, 1.2 eq.) of 4-aminobiphenyl (CAS 92-67-1) are initially introduced in 950 ml of toluene together with 32.0 g (117 mmol, 1.0 eq.) of 2-bromo-9,9'-dimethylfluorene (CAS 28320-31-2) and saturated with argon for 30 minutes. 1.0 g (1.8 mmol, 0.02 eq.) of 1,1'-bis (diphenylphosphino)ferrocene (CAS 12150-46-8), 350 mg (1.6 mmol, 0.01 eq.) of palladium(II) acetate (CAS 3375-31-3) and 29 g (300 mmol, 2.6 eq.) of sodium tertbutoxide (CAS 865-48-5) are subsequently added, and the mixture is heated under reflux overnight. When the reaction is complete, the batch is diluted with 300 ml of toluene and extracted with water. The organic phase is dried over sodium sulfate, and the solvent is removed in a rotary evaporator. 50 ml of ethyl acetate are added to the brown oil, and the mixture is added to a mixture of heptane/ethyl acetate 20:1. The solid formed is filtered off with suction and washed with heptane. Drying gives 29 g (80 mmol, 69%) of the desired product h having an HPLC purity of 99.1%.

The following compounds are prepared analogously:

| No. | Starting material 1 | Starting material 2 | Product | Yield |
|---|---|---|---|---|
| h1 | NH₂ (92-67-1) | Br (2052-07-5) | | 71% |
| h2 | NH₂ (92-67-1) | Br (942615-32-9) | | 61% |

-continued
| No. | Starting material 1 | Starting material 2 | Product | Yield |
|---|---|---|---|---|
| h3 | 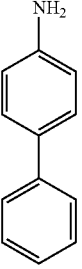 [SMILES: Nc1ccc(-c2ccccc2)cc1]<br>92-67-1 | 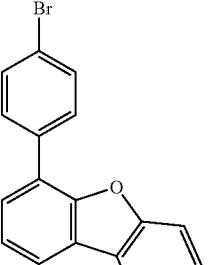<br>955959-84-9 | 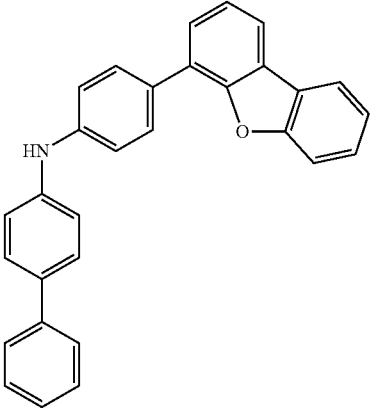 [SMILES: c1ccc(-c2ccc(Nc3ccc(-c4cccc5c4oc4ccccc45)cc3)cc2)cc1] | 78% |
| h4 | 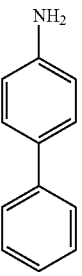 [SMILES: Nc1ccc(-c2ccccc2)cc1]<br>92-67-1 | 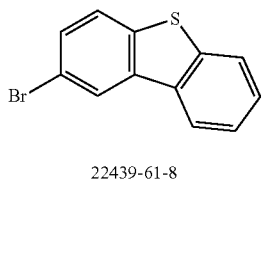<br>22439-61-8 | 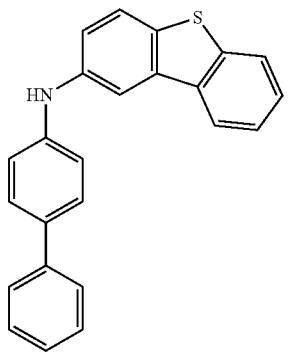 [SMILES: c1ccc(-c2ccc(Nc3ccc4sc5ccccc5c4c3)cc2)cc1] | 82% |
| h5 | 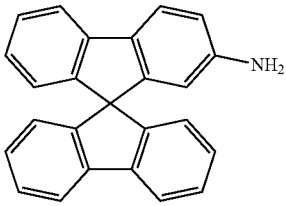 [SMILES: Nc1ccc2c(c1)C1(c3ccccc3-c3ccccc31)c1ccccc1-2]<br>118951-68-1 | 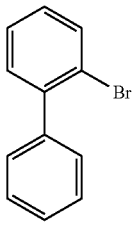 [SMILES: Brc1ccccc1-c1ccccc1]<br>2052-07-5 | 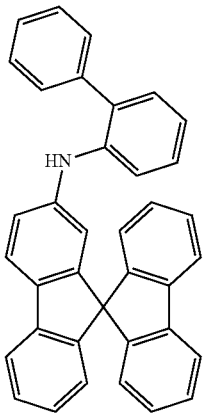 [SMILES: c1ccc(-c2ccccc2Nc2ccc3c(c2)C2(c4ccccc4-c4ccccc42)c2ccccc2-3)cc1] | 62% |

-continued
| No. | Starting material 1 | Starting material 2 | Product | Yield |
|---|---|---|---|---|
| h6 | 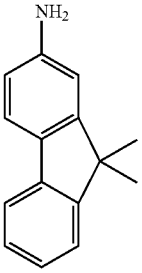<br>108714-73-4 | 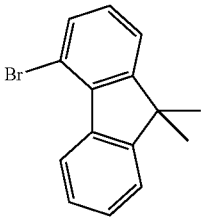 [SMILES: CC1(C)c2ccccc2-c2c(Br)cccc21]<br>942615-32-9 | 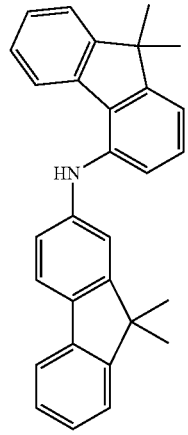 [SMILES: CC1(C)c2ccccc2-c2ccc(Nc3cccc4c3-c3ccccc3C4(C)C)cc21] | 47% |
| h7 | 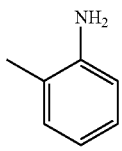<br>95-53-4 | 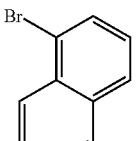<br>90-11-9 | 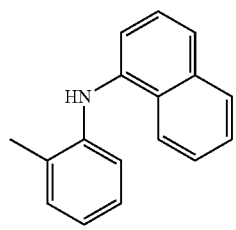 [SMILES: Cc1ccccc1Nc1cccc2ccccc12] | 92% |
| h8 | 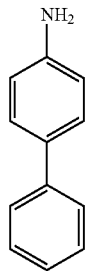 [SMILES: Nc1ccc(-c2ccccc2)cc1]<br>92-67-1 | 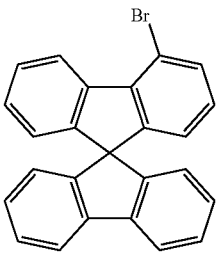 [SMILES: Brc1cccc2c1-c1ccccc1C21c2ccccc2-c2ccccc21]<br>171408-76-7 | 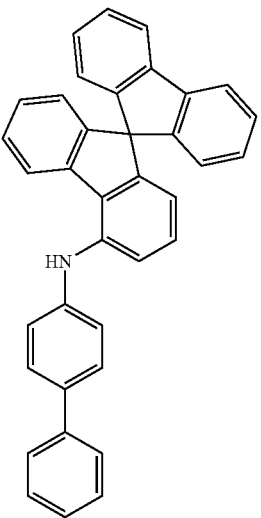 [SMILES: c1ccc(-c2ccc(Nc3cccc4c3-c3ccccc3C43c4ccccc4-c4ccccc43)cc2)cc1] | 75% |

| No. | Starting material 1 | Starting material 2 | Product | Yield |
|---|---|---|---|---|
| h9 | 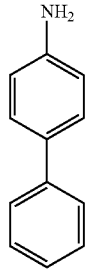 [SMILES: Nc1ccc(-c2ccccc2)cc1] 92-67-1 | 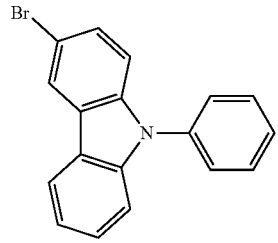 [SMILES: Brc1ccc2c(c1)c1ccccc1n2-c1ccccc1] 1153-85-1 | 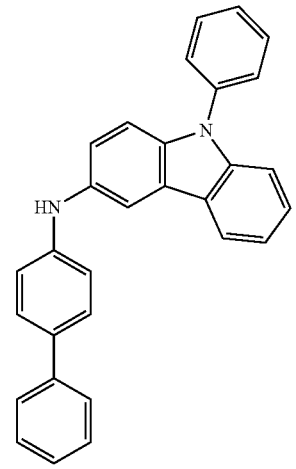 [SMILES: c1ccc(-c2ccc(Nc3ccc4c(c3)c3ccccc3n4-c3ccccc3)cc2)cc1] | 84% |
| h10 | 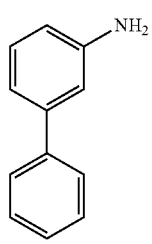 [SMILES: Nc1cccc(-c2ccccc2)c1] 90-41-5 | 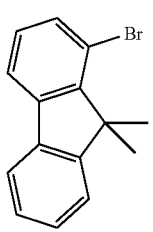 [SMILES: CC1(C)c2ccccc2-c2cccc(Br)c21] 1225053-54-2 | 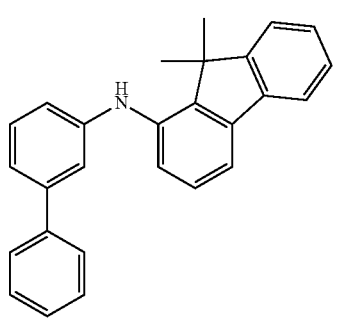 [SMILES: CC1(C)c2ccccc2-c2cccc(Nc3cccc(-c4ccccc4)c3)c21] | 62% |
The following compounds are prepared analogously to the procedure Indicated above under g):

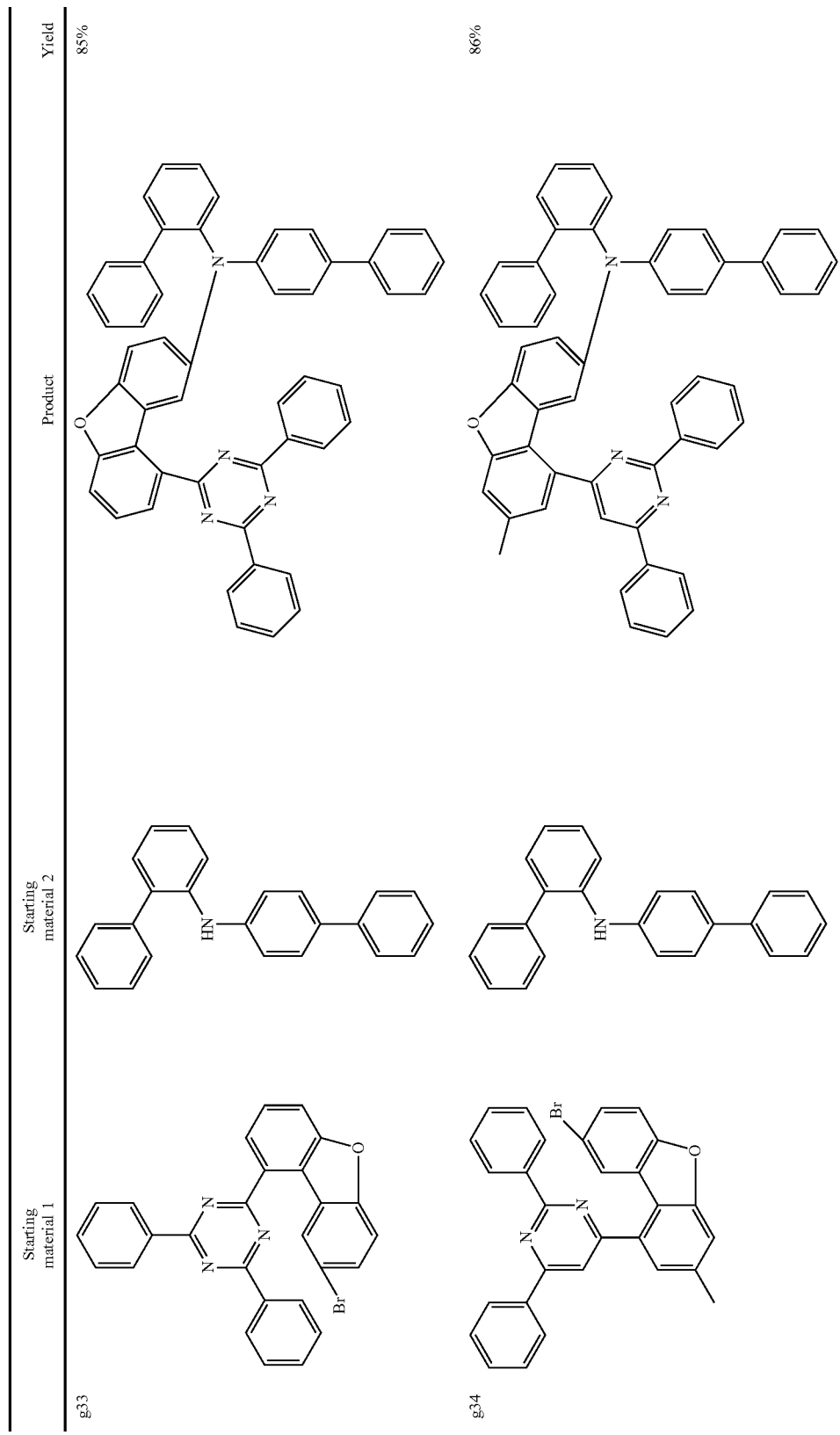

-continued

| | Starting material 1 | Starting material 2 | Product | Yield |
|---|---|---|---|---|
| g35 | | | | 83% |
| g36 | | | | 80% |

| | Starting material 1 | Starting material 2 | Product | Yield |
|---|---|---|---|---|
| g37 | 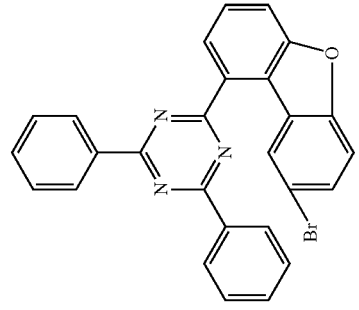 | 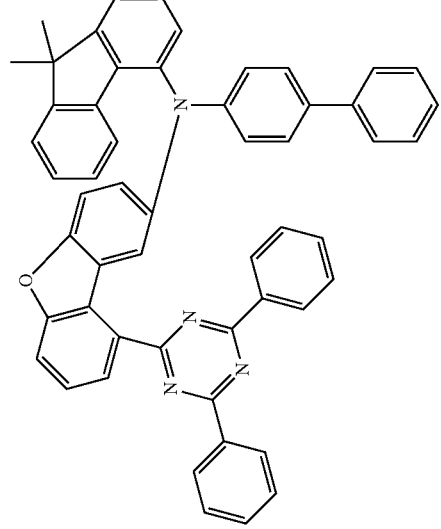 | 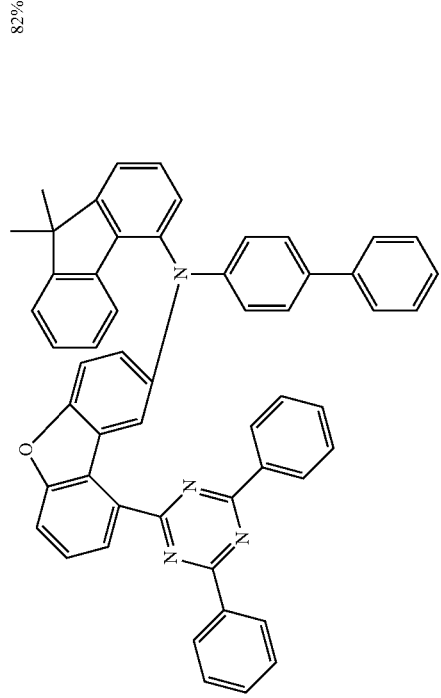 | 82% |
| g38 | 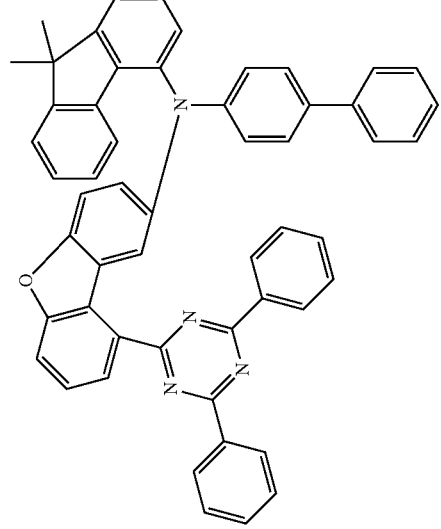 | 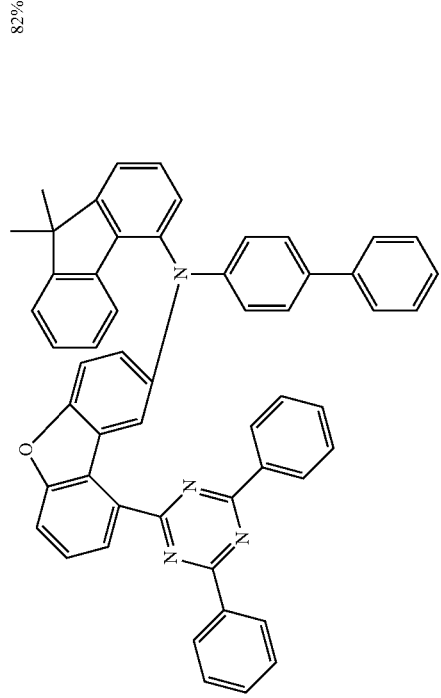 | 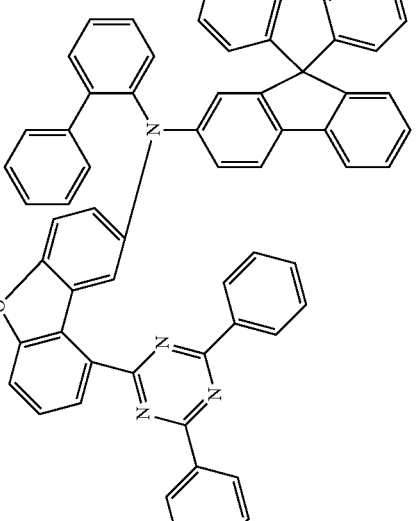 | 81% |

| | Starting material 1 | Starting material 2 | Product | Yield |
|---|---|---|---|---|
| g39 | 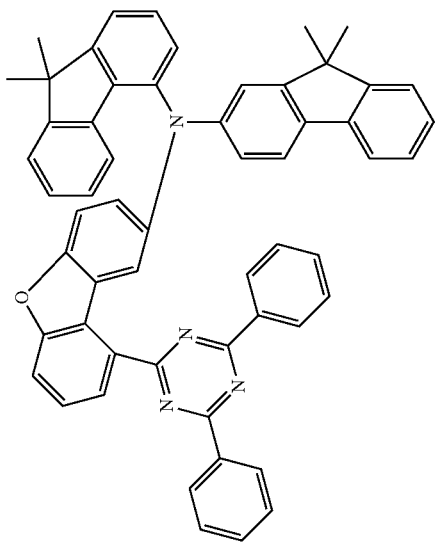 | 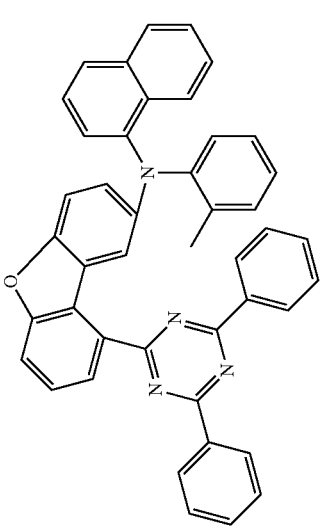 | 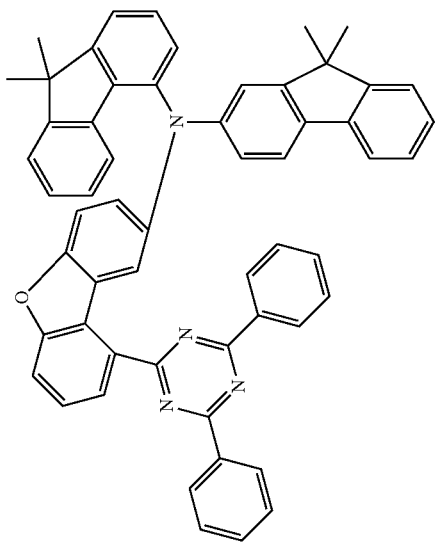 | 87% |
| g40 | 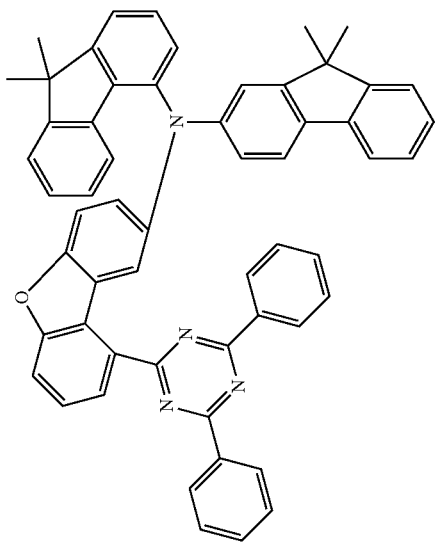 | 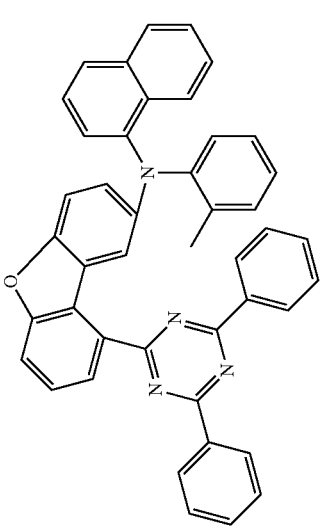 | 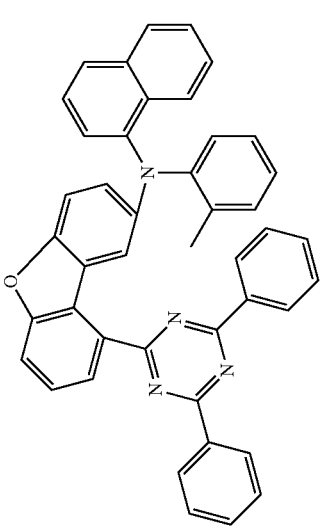 | 86% |

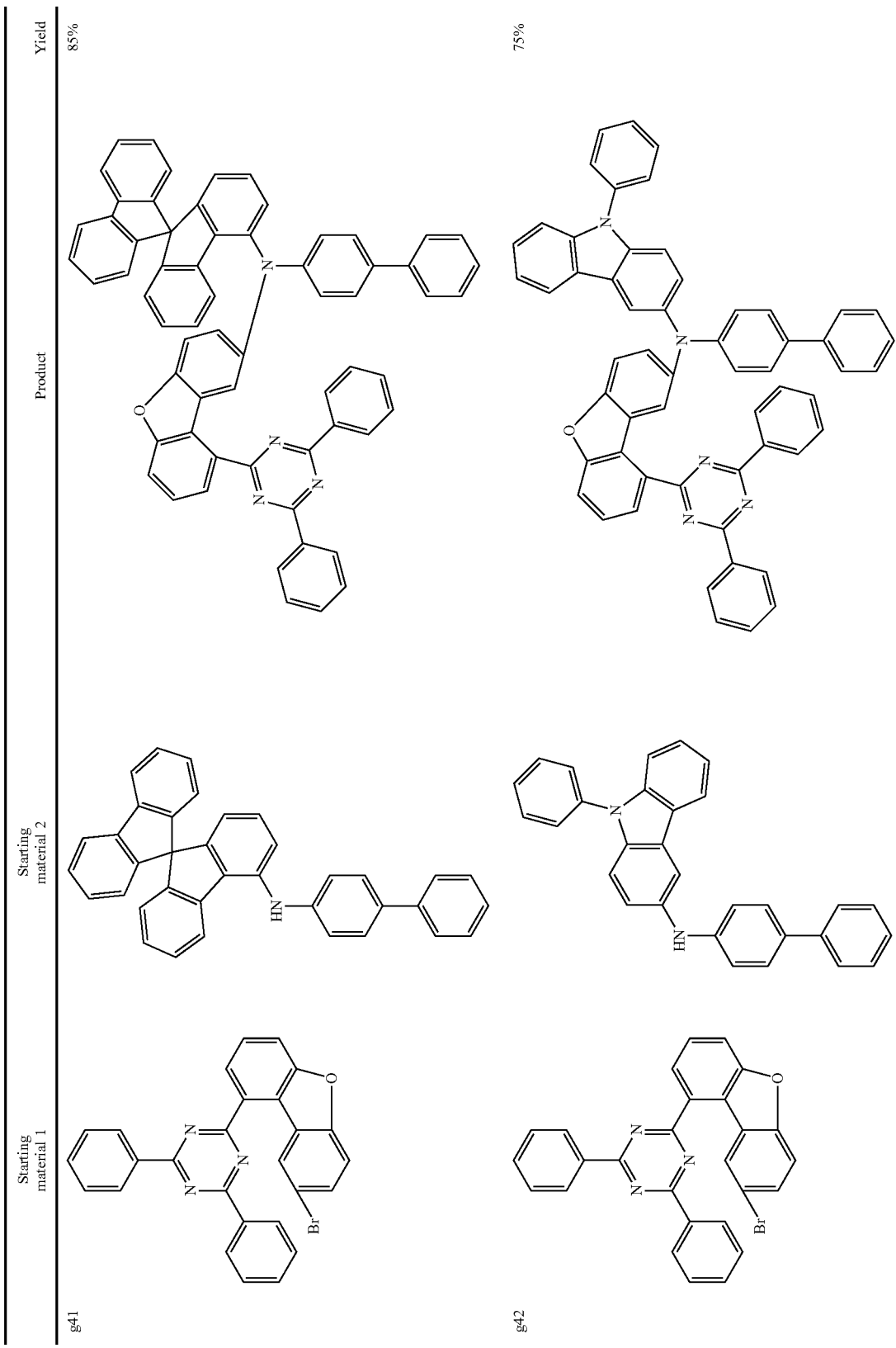

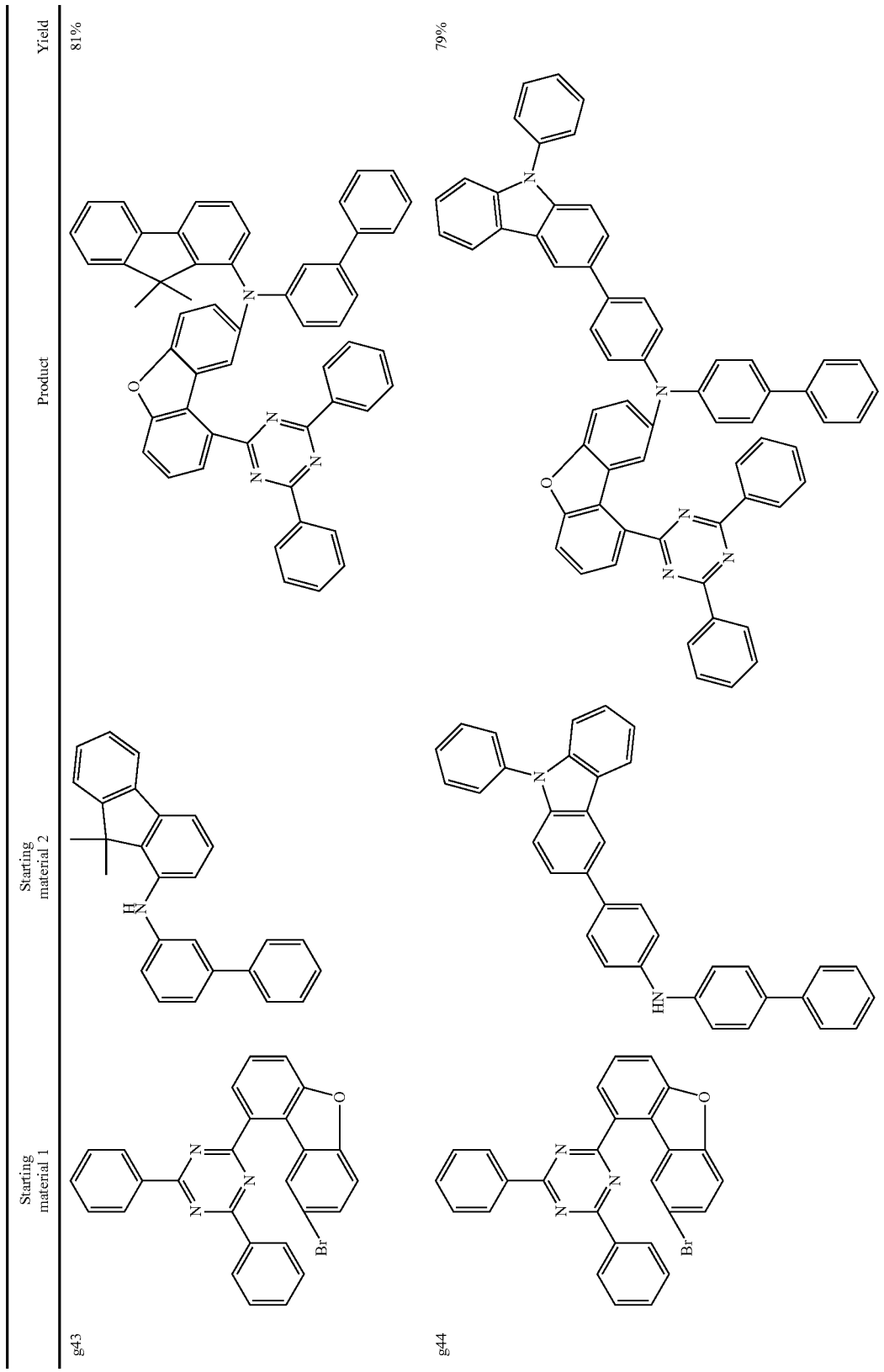

-continued
| Starting material 1 | Starting material 2 | Product | Yield |
|---|---|---|---|
| g45 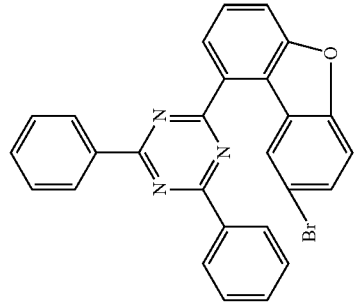 | 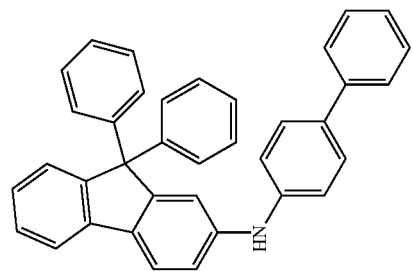 | 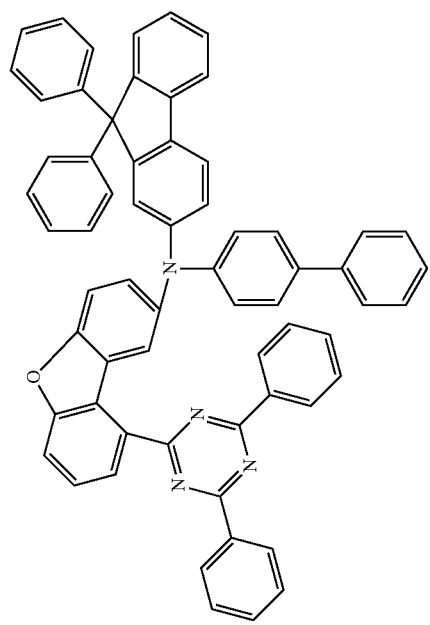 | 85% |
| g46 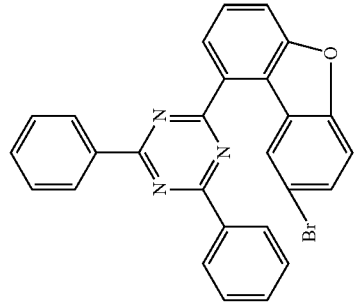 | 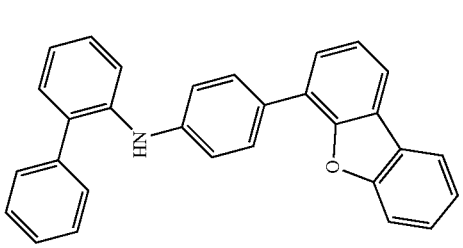 | 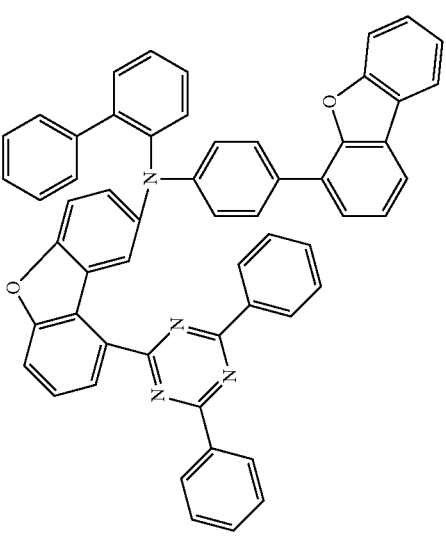 | 79% |

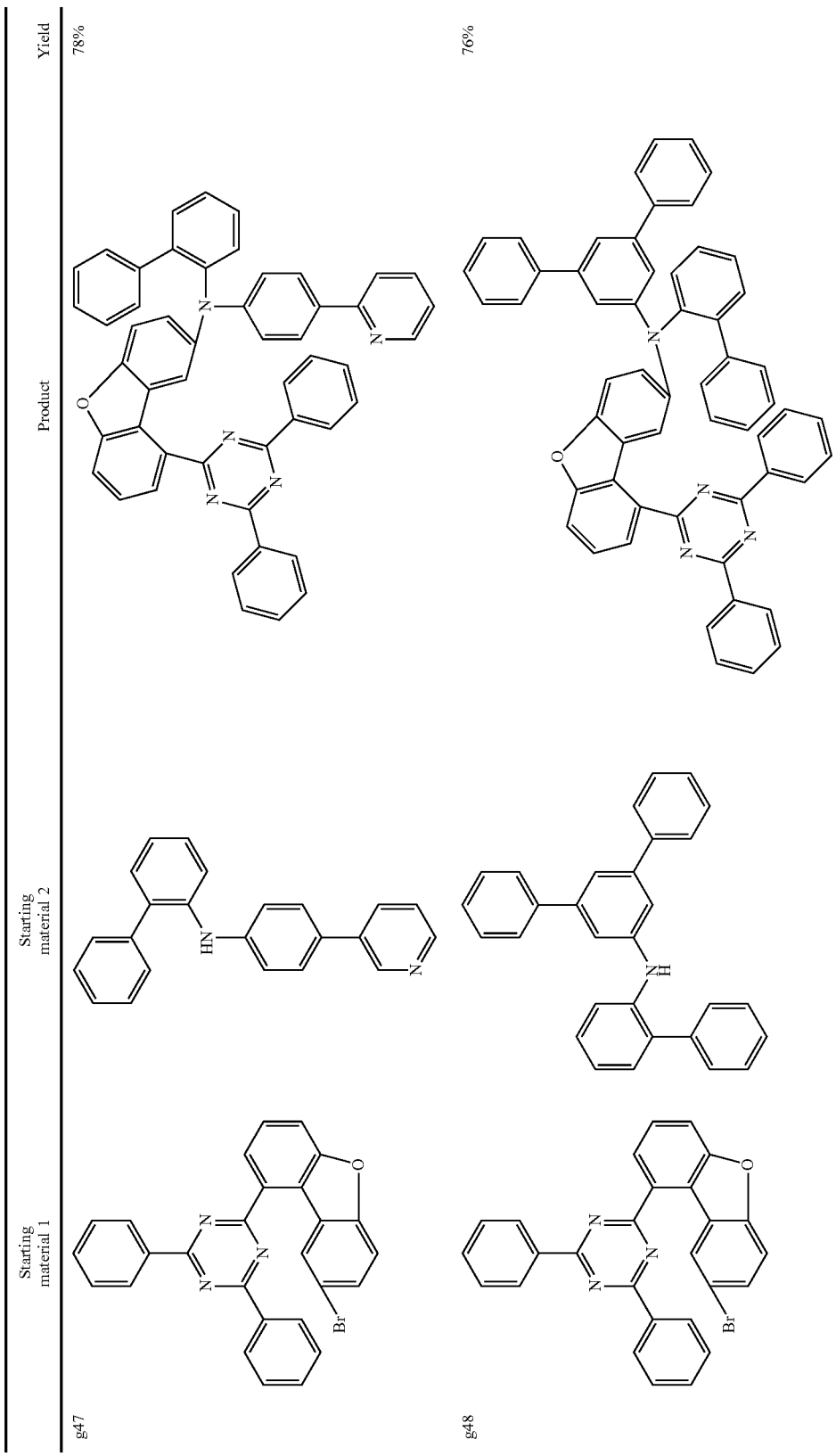

| | Starting material 1 | Starting material 2 | Product | Yield |
|---|---|---|---|---|
| g49 | 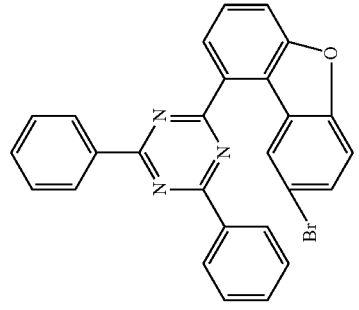 | 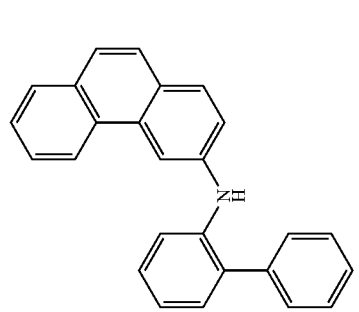 | 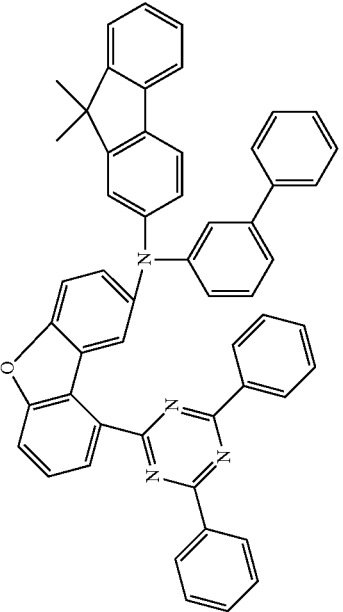 | 80% |
| g50 | 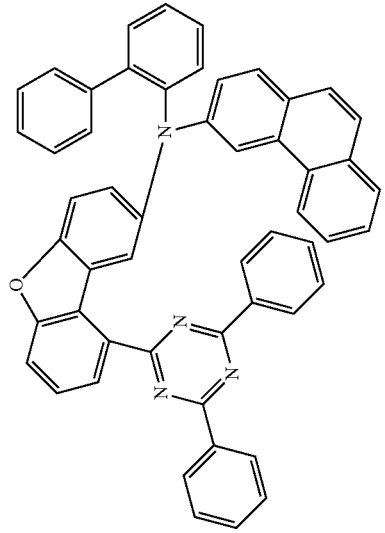 | 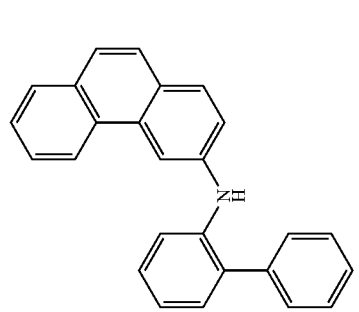 | 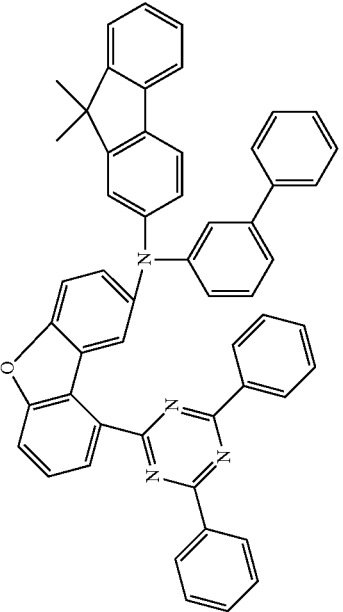 | 74% |

Production of the OLEDs

The data of various OLEDs are presented in the following Examples V1 to E20 (see Tables 1 and 2).

Pre-Treatment for Examples V1-E20:

Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL) I/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium cathode with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. An expression such as IC1:IC3:TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 denotes the external quantum efficiency at an operating luminous density of 1000 cd/m$^2$. The lifetime LT is defined as the time after which the luminous density drops to a certain proportion L1 from the initial luminous density on operation at constant current. An expression of L0; j0=4000 cd/m$^2$ and L1=70% in Table 2 means that the lifetime indicated in column LT corresponds to the time after which the initial luminous density drops from 4000 cd/m$^2$ to 2800 cd/m$^2$. Analogously, L0; j0=20 mA/cm$^2$, L1=80% means that the luminous density on operation at 20 mA/cm$^2$ drops to 80% of its initial value after time LT.

The data of the various OLEDs are summarised in Table 2. Examples V1-V5 are OLEDs comparative examples in accordance with the prior art, Examples E1-E20 show data of OLEDs according to the invention.

Some of the examples are explained in greater detail below in order to illustrate the advantages of the compounds according to the invention.

Use of Mixtures According to the Invention in the Emission Layer of Phosphorescent OLEDs On use as matrix materials in phosphorescent OLEDs, the materials according to the invention give rise to significant improvements over the prior art with respect to the lifetime of the components. Use of compounds EG1 to EG4 according to the invention in combination with the green-emitting dopant TEG1 enables an increase in the lifetime by over 200% compared with the prior art to be observed (comparison of Examples V1 with E1 and V2 with E2 as well as V3 with E3 and V4, V5 with E4).

TABLE 1

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| V1 | SpA1 70 nm | HATCN 5 nm | SpMA1 90 nm | SdT1:TEG1 (90%:10%) 30 nm | ST2 10 nm | ST2:LiQ (50%:50%) 30 nm | — |
| V2 | SpA1 70 nm | HATCN 5 nm | SpMA1 90 nm | SdT2:TEG1 (90%:10%) 30 nm | ST2 10 nm | ST2:LiQ (50%:50%) 30 nm | — |
| V3 | SpA1 70 nm | HATCN 5 nm | SpMA1 90 nm | SdT3:TEG1 (90%:10%) 30 nm | ST2 10 nm | ST2:LiQ (50%:50%) 30 nm | — |
| V4 | SpA1 70 nm | HATCN 5 nm | SpMA1 90 nm | SdT4:TEG1 (90%:10%) 30 nm | ST2 10 nm | ST2:LiQ (50%:50%) 30 nm | — |
| V5 | SpA1 70 nm | HATCN 5 nm | SpMA1 90 nm | SdT5:TEG1 (90%:10%) 30 nm | ST2 10 nm | ST2:LiQ (50%:50%) 30 nm | — |
| E1 | SpA1 70 nm | HATCN 5 nm | SpMA1 90 nm | EG1:TEG1 (90%:10%) 30 nm | ST2 10 nm | ST2:LiQ (50%:50%) 30 nm | — |
| E2 | SpA1 70 nm | HATCN 5 nm | SpMA1 90 nm | EG2:TEG1 (90%:10%) 30 nm | ST2 10 nm | ST2:LiQ (50%:50%) 30 nm | — |
| E3 | SpA1 70 nm | HATCN 5 nm | SpMA1 90 nm | EG3:TEG1 (90%:10%) 30 nm | ST2 10 nm | ST2:LiQ (50%:50%) 30 nm | — |
| E4 | SpA1 70 nm | HATCN 5 nm | SpMA1 90 nm | EG4:TEG1 (90%:10%) 30 nm | ST2 10 nm | ST2:LiQ (50%:50%) 30 nm | — |

TABLE 1-continued

Structure of the OLEDs

| Ex. | HTL Thickness | IL Thickness | EBL Thickness | EML Thickness | HBL Thickness | ETL Thickness | EIL Thickness |
|---|---|---|---|---|---|---|---|
| E5 | SpA1 90 nm | HATCN 5 nm | SpMA1 130 nm | EG5:TER1 (92%:8%) 30 nm | — | ST2:LiQ (50%:50%) 40 nm | — |
| E6 | SpA1 90 nm | HATCN 5 nm | SpMA1 130 nm | EG6:TER1 (92%:8%) 30 nm | — | ST2:LiQ (50%:50%) 40 nm | — |
| E7 | SpA1 70 nm | HATCN 5 nm | SpMA1 90 nm | EG7:TEG1 (90%:10%) 30 nm | — | ST2:LiQ (50%:50%) 40 nm | — |
| E8 | SpA1 70 nm | HATCN 5 nm | SpMA1 90 nm | EG8:TEG1 (90%:10%) 30 nm | — | ST2:LiQ (50%:50%) 40 nm | — |
| E9 | SpA1 70 nm | HATCN 5 nm | SpMA1 90 nm | EG9:IC3:TEG1 (45%:45%:10%) 30 nm | IC1 10 nm | ST2:LiQ (50%:50%) 30 nm | — |
| E10 | SpA1 70 nm | HATCN 5 nm | SpMA1 90 nm | EG10:IC3:TEG1 (45%:45%:10%) 30 nm | IC1 10 nm | ST2:LiQ (50%:50%) 30 nm | — |
| E11 | SpA1 70 nm | HATCN 5 nm | SpMA1 90 nm | EG11:IC3:TEG1 (45%:45%:10%) 30 nm | IC1 10 nm | ST2:LiQ (50%:50%) 30 nm | — |
| E12 | SpA1 70 nm | HATCN 5 nm | SpMA1 90 nm | IC1:TEG1 (90%:10%) 30 nm | — | EG8 40 nm | LiQ 3 nm |
| E13 | SpA1 70 nm | HATCN 5 nm | SpMA1 90 nm | IC1:TEG1 (90%:10%) 30 nm | IC1 10 nm | EG9:LiQ (50%:50%) 30 nm | — |
| E14 | SpA1 70 nm | HATCN 5 nm | SpMA1 90 nm | EG14:IC3:TEG1 (65%:25%:10%) 30 nm | IC1 10 nm | ST2:LiQ (50%:50%) 30 nm | — |
| E15 | SpA1 70 nm | HATCN 5 nm | SpMA1 90 nm | IC1:TEG1 (90%:10%) 30 nm | EG15 10 nm | ST2:LiQ (50%:50%) 30 nm | — |
| E16 | HATCN 5 nm | SpMA1 70 nm | SpMA2 15 nm | EG16:L1:TEY1 (45%:45%:10%) 25 nm | — | ST1 45 nm | LiQ 3 nm |
| E17 | SpA1 70 nm | HATCN 5 nm | SpMA1 90 nm | EG17:TEG1 (90%:10%) 30 nm | ST2 10 nm | ST2:LiQ (50%:50%) 30 nm | — |
| E18 | SpA1 70 nm | HATCN 5 nm | SpMA1 90 nm | EG18:IC3:TEG1 (45%:45%:10%) 30 nm | IC1 10 nm | ST2:LiQ (50%:50%) 30 nm | — |
| E19 | HATCN 5 nm | SpMA1 70 nm | SpMA2 15 nm | EG16:L1:TEY1 (45%:45%:10%) 25 nm | — | ST1 45 nm | LiQ 3 nm |
| E20 | SpA1 70 nm | HATCN 5 nm | SpMA1 90 nm | IC1:TEG1 (90%:10%) 30 nm | EG20 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y at 1000 cd/m$^2$ | $L_0$; $j_0$ | L1 % | LT (h) |
|---|---|---|---|---|---|---|---|---|
| V1 | 3.6 | 51 | 44 | 13.7% | 0.33/0.63 | 20 mA/cm$^2$ | 80 | 95 |
| V2 | 4.2 | 50 | 37 | 14.3% | 0.33/0.62 | 20 mA/cm$^2$ | 80 | 10 |
| V3 | 4.3 | 55 | 40 | 14.7% | 0.33/0.64 | 20 mA/cm$^2$ | 80 | 15 |
| V4 | 3.5 | 48 | 43 | 12.8% | 0.32/0.64 | 20 mA/cm$^2$ | 80 | 190 |
| V5 | 3.7 | 59 | 50 | 15.7% | 0.33/0.64 | 20 mA/cm$^2$ | 80 | 125 |
| E1 | 3.5 | 40 | 36 | 11.6% | 0.33/0.62 | 20 mA/cm$^2$ | 80 | 290 |
| E2 | 4.3 | 51 | 37 | 14.5% | 0.33/0.62 | 20 mA/cm$^2$ | 80 | 20 |
| E3 | 4.4 | 55 | 39 | 15.0% | 0.33/0.63 | 20 mA/cm$^2$ | 80 | 35 |
| E4 | 3.6 | 41 | 36 | 11.9% | 0.32/0.63 | 20 mA/cm$^2$ | 80 | 300 |
| E5 | 4.4 | 13 | 9 | 12.4% | 0.66/0.34 | 4000 cd/m$^2$ | 80 | 340 |
| E6 | 4.6 | 11 | 8 | 11.4% | 0.67/0.34 | 4000 cd/m$^2$ | 80 | 370 |
| E7 | 3.4 | 59 | 55 | 15.9% | 0.33/0.63 | 20 mA/cm$^2$ | 80 | 115 |
| E8 | 3.6 | 56 | 49 | 15.2% | 0.33/0.62 | 20 mA/cm$^2$ | 80 | 125 |
| E9 | 3.4 | 62 | 57 | 16.5% | 0.34/0.63 | 20 mA/cm$^2$ | 80 | 240 |
| E10 | 3.5 | 60 | 54 | 16.1% | 0.33/0.63 | 20 mA/cm$^2$ | 80 | 350 |
| E11 | 3.6 | 57 | 50 | 15.5% | 0.33/0.63 | 20 mA/cm$^2$ | 80 | 290 |

TABLE 2-continued
Data of the OLEDs
| Ex. | U1000 (V) | CE1000 (cd/A) | PE1000 (lm/W) | EQE 1000 | CIE x/y at 1000 cd/m² | $L_0; j_0$ | L1 % | LT (h) |
|---|---|---|---|---|---|---|---|---|
| E12 | 3.3 | 64 | 61 | 17.1% | 0.33/0.63 | 20 mA/cm² | 80 | 125 |
| E13 | 3.7 | 62 | 53 | 16.5% | 0.34/0.63 | 20 mA/cm² | 80 | 165 |
| E14 | 3.3 | 60 | 57 | 16.7% | 0.32/0.63 | 20 mA/cm² | 80 | 270 |
| E15 | 3.5 | 59 | 53 | 16.0% | 0.34/0.63 | 20 mA/cm² | 80 | 145 |
| E16 | 2.9 | 75 | 81 | 22.4% | 0.44/0.55 | 50 mA/cm² | 90 | 85 |
| E17 | 3.4 | 41 | 37 | 11.7% | 0.33/0.63 | 20 mA/cm² | 80 | 140 |
| E18 | 3.5 | 60 | 53 | 16.3% | 0.33/0.63 | 20 mA/cm² | 80 | 260 |
| E19 | 2.8 | 77 | 86 | 23.1% | 0.45/0.55 | 50 mA/cm² | 90 | 100 |
| E20 | 3.7 | 59 | 50 | 15.8% | 0.33/0.63 | 20 mA/cm² | 80 | 155 |
TABLE 3
Structural formulae of the materals for the OLEDs
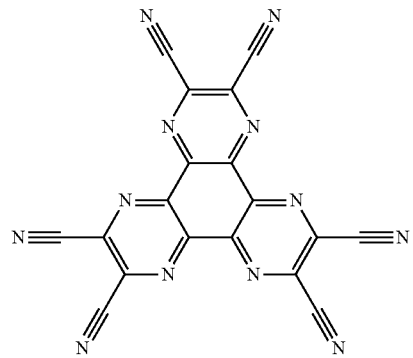 [SMILES: N#Cc1nc2c3nc(C#N)c(C#N)nc3c3nc(C#N)c(C#N)nc3c2nc1C#N]
HATCN
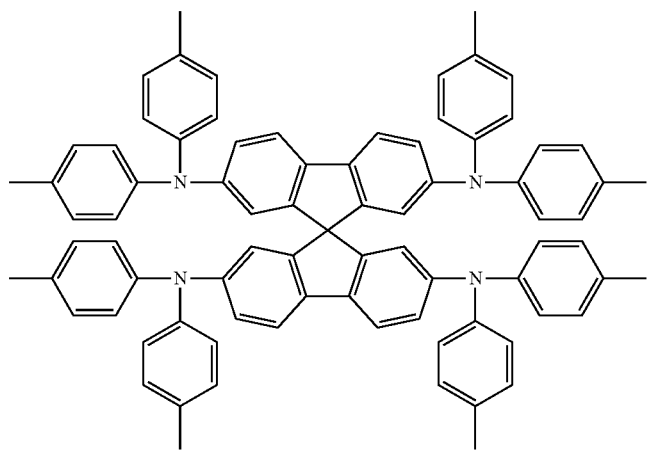
SpA1

TABLE 3-continued
Structural formulae of the materials for the OLEDs
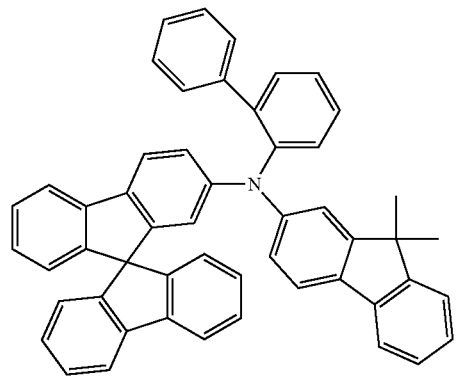 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
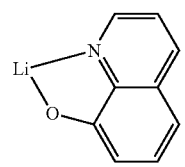
LiQ
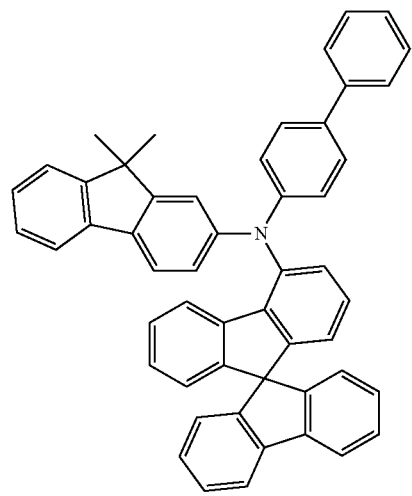 [SMILES: CC1(C)c2ccccc2-c2ccc(N(c3ccc(-c4ccccc4)cc3)c3cccc4c3-c3ccccc3C43c4ccccc4-c4ccccc43)cc21]
SpMA2
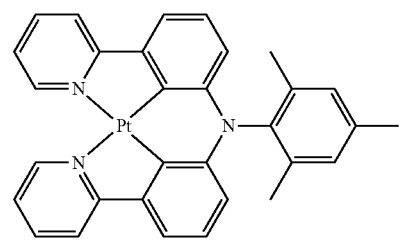
TER1

TABLE 3-continued
Structural formulae of the materals for the OLEDs
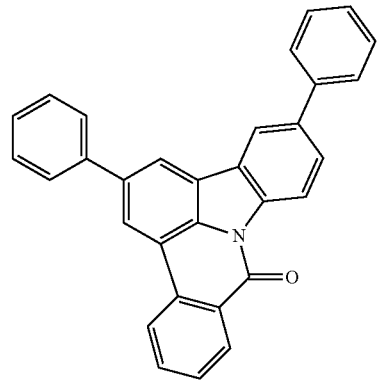 [SMILES: O=c1c2ccccc2c2cc(-c3ccccc3)cc3c4cc(-c5ccccc5)ccc4n1c23]
L1
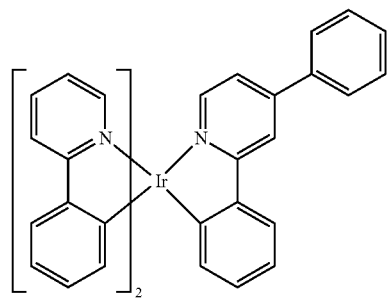
TEY1
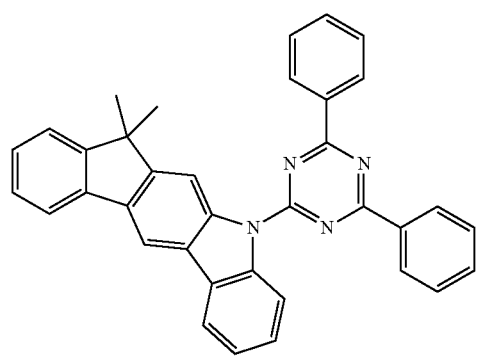 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materals for the OLEDs
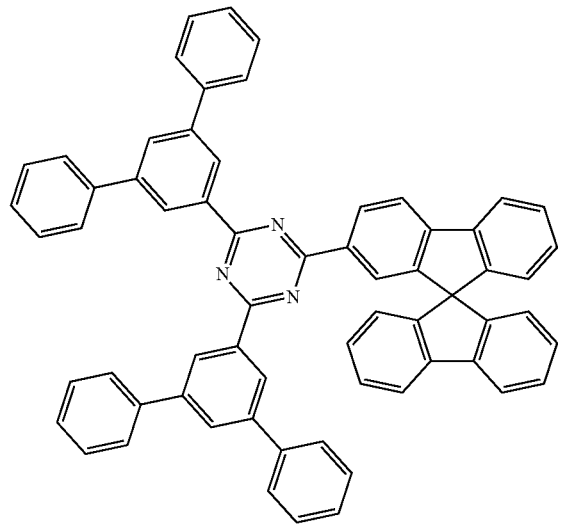 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
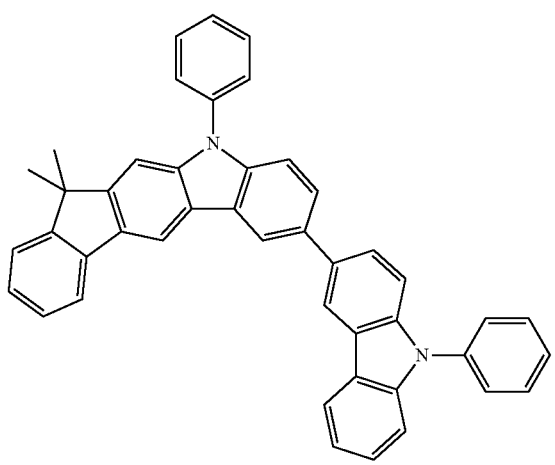 [SMILES: CC1(C)c2ccccc2-c2cc3c4cc(-c5ccc6c(c5)c5ccccc5n6-c5ccccc5)ccc4n(-c4ccccc4)c3cc21]
IC3
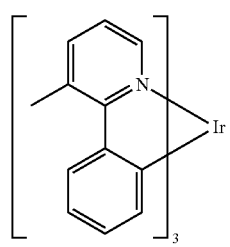
TEG1

TABLE 3-continued
Structural formulae of the materals for the OLEDs
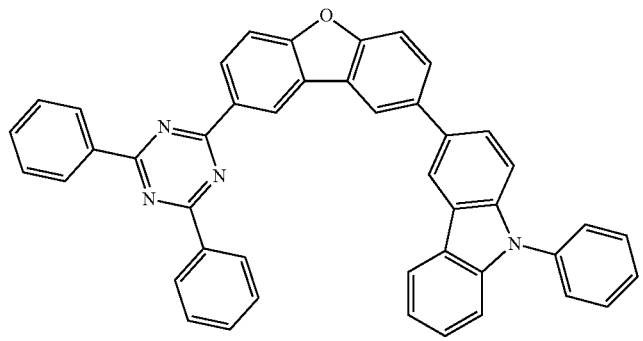 [SMILES: c1ccc(-c2nc(-c3ccccc3)nc(-c3ccc4oc5ccc(-c6ccc7c(c6)c6ccccc6n7-c6ccccc6)cc5c4c3)n2)cc1]
SdT1
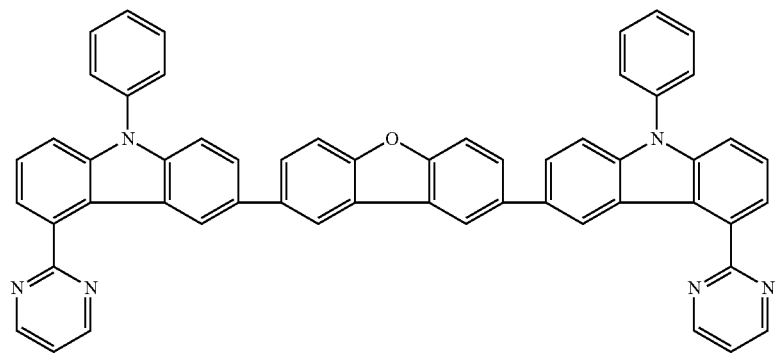 [SMILES: c1ccc(-n2c3ccc(-c4ccc5oc6ccc(-c7ccc8c(c7)c7c(-c9ncccn9)cccc7n8-c7ccccc7)cc6c5c4)cc3c3c(-c4ncccn4)cccc32)cc1]
SdT2
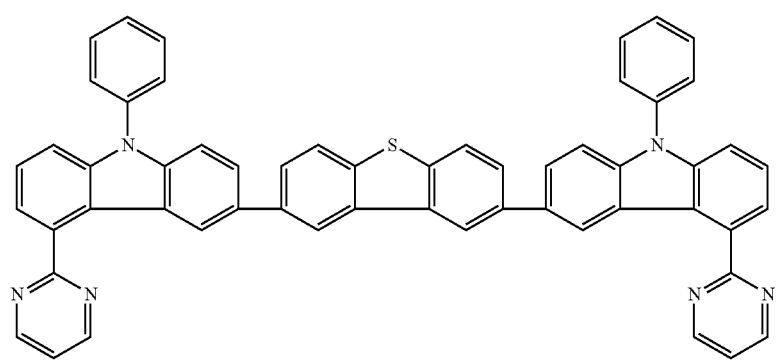 [SMILES: c1ccc(-n2c3ccc(-c4ccc5sc6ccc(-c7ccc8c(c7)c7c(-c9ncccn9)cccc7n8-c7ccccc7)cc6c5c4)cc3c3c(-c4ncccn4)cccc32)cc1]
SdT3

TABLE 3-continued
Structural formulae of the materals for the OLEDs
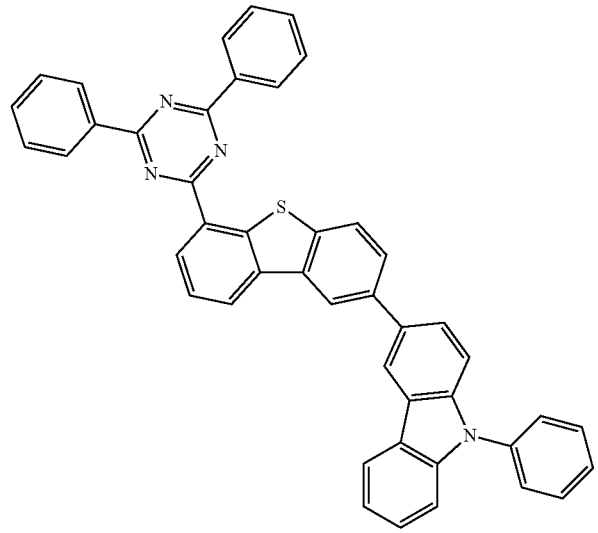 [SMILES: c1ccc(-c2nc(-c3ccccc3)nc(-c3cccc4c3sc3ccc(-c5ccc6c(c5)c5ccccc5n6-c5ccccc5)cc34)n2)cc1]
SdT4
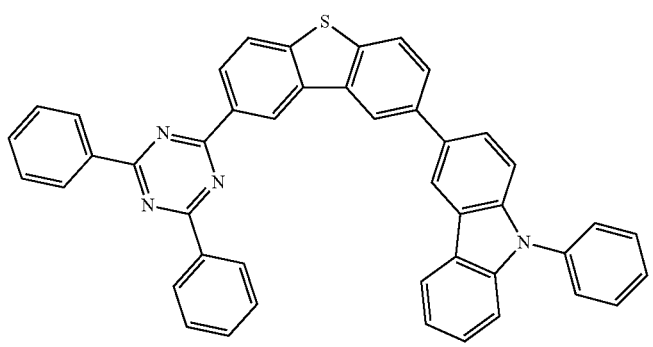 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]
SdT5
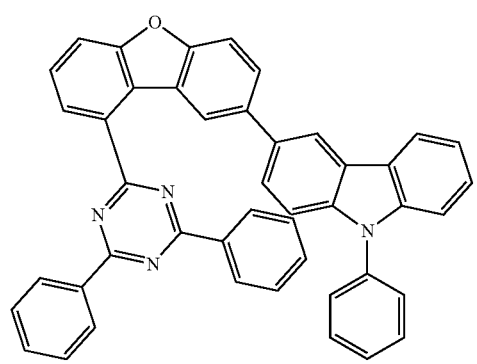 [SMILES: c1ccc(-c2nc(-c3ccccc3)nc(-c3cccc4oc5ccc(-c6ccc7c(c6)c6ccccc6n7-c6ccccc6)cc5c34)n2)cc1]
EG1

TABLE 3-continued
Structural formulae of the materals for the OLEDs
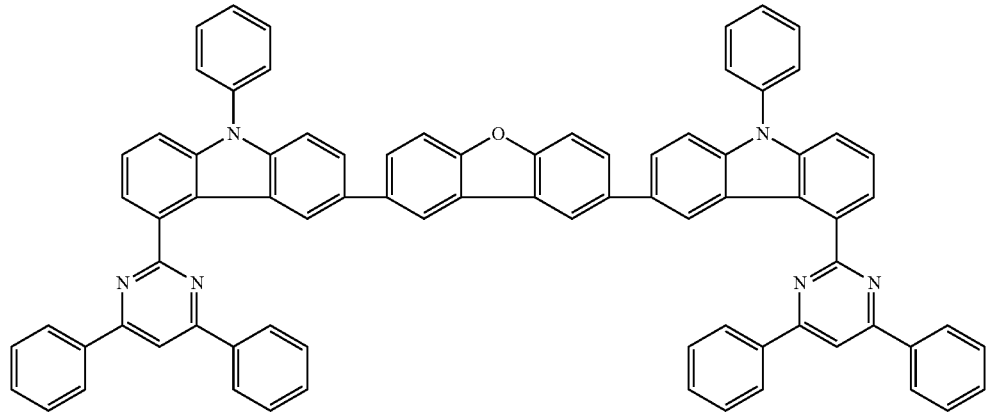 [SMILES: c1ccc(-c2cc(-c3ccccc3)nc(-c3cccc4c3c3cc(-c5ccc6oc7ccc(-c8ccc9c(c8)c8c(-c%10nc(-c%11ccccc%11)cc(-c%11ccccc%11)n%10)cccc8n9-c8ccccc8)cc7c6c5)ccc3n4-c3ccccc3)n2)cc1]
EG2
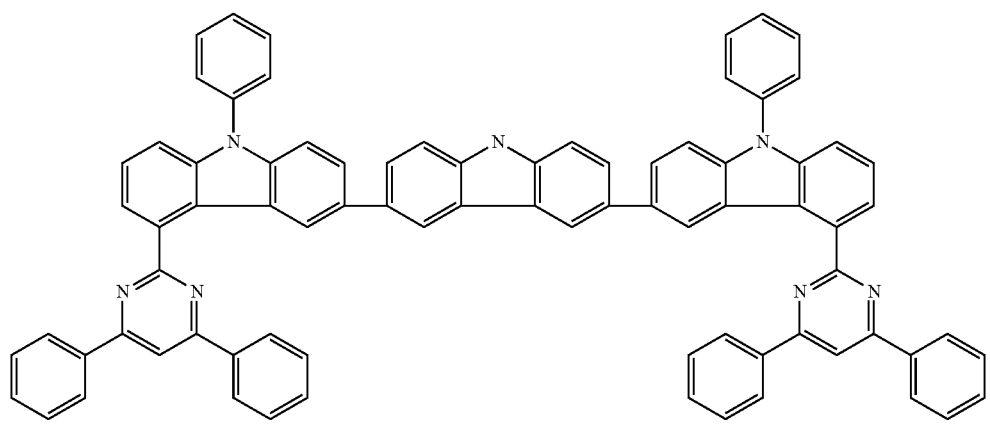 [SMILES: c1ccc(-c2cc(-c3ccccc3)nc(-c3cccc4c3c3cc(-c5ccc6[nH]c7ccc(-c8ccc9c(c8)c8c(-c%10nc(-c%11ccccc%11)cc(-c%11ccccc%11)n%10)cccc8n9-c8ccccc8)cc7c6c5)ccc3n4-c3ccccc3)n2)cc1]
EG3
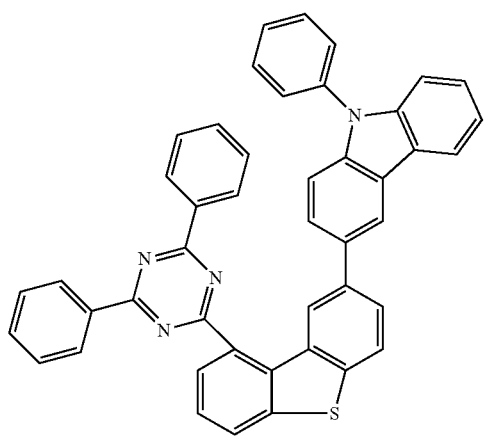 [SMILES: c1ccc(-c2nc(-c3ccccc3)nc(-c3cccc4sc5ccc(-c6ccc7c(c6)c6ccccc6n7-c6ccccc6)cc5c34)n2)cc1]
EG4

TABLE 3-continued
Structural formulae of the materals for the OLEDs
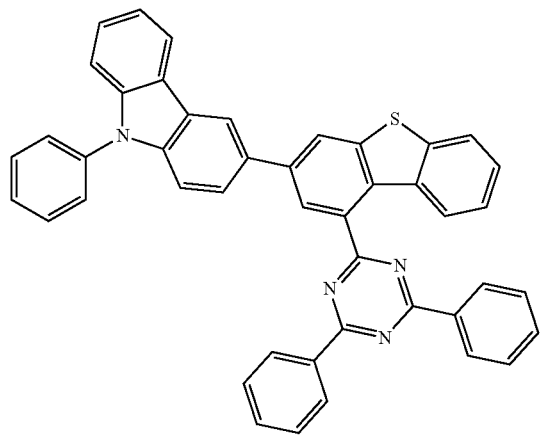 [SMILES: c1ccc(-c2nc(-c3ccccc3)nc(-c3cc(-c4ccc5c(c4)c4ccccc4n5-c4ccccc4)cc4sc5ccccc5c34)n2)cc1]
EG5
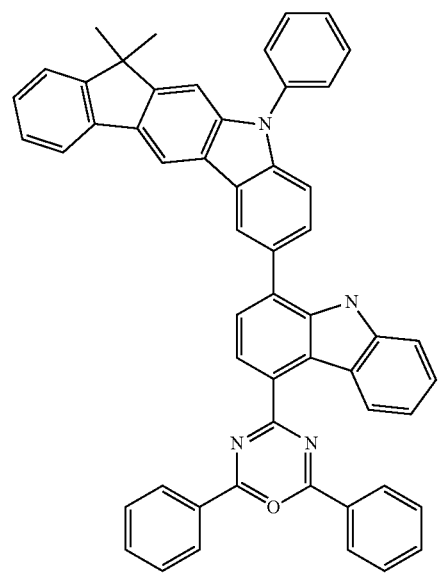
EG6

TABLE 3-continued
Structural formulae of the materals for the OLEDs
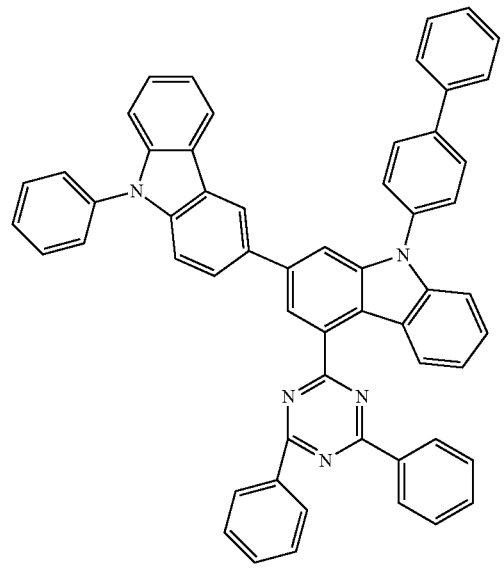 [SMILES: c1ccc(-c2ccc(-n3c4ccccc4c4c(-c5nc(-c6ccccc6)nc(-c6ccccc6)n5)cc(-c5ccc6c(c5)c5ccccc5n6-c5ccccc5)cc43)cc2)cc1]
EG7
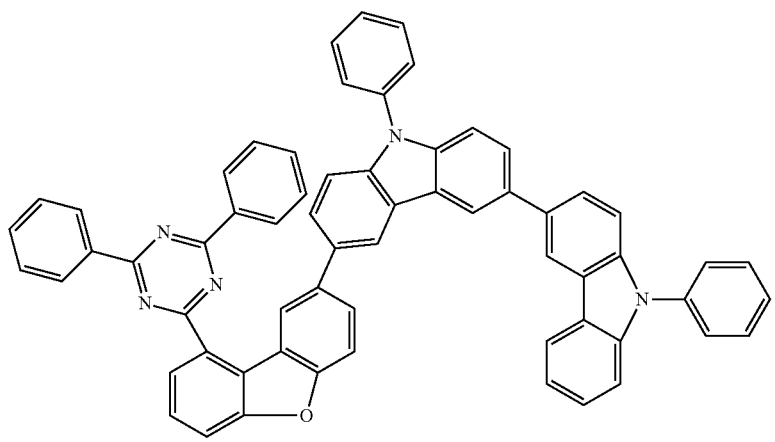 [SMILES: c1ccc(-c2nc(-c3ccccc3)nc(-c3cccc4oc5ccc(-c6ccc7c(c6)c6cc(-c8ccc9c(c8)c8ccccc8n9-c8ccccc8)ccc6n7-c6ccccc6)cc5c34)n2)cc1]
EG8
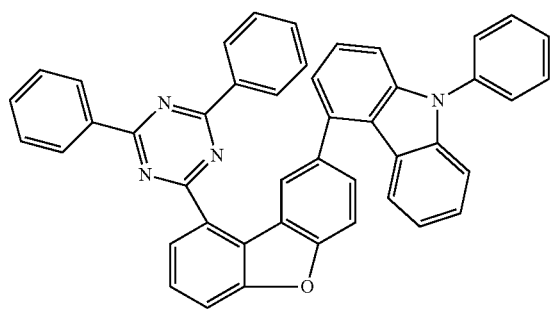 [SMILES: c1ccc(-c2nc(-c3ccccc3)nc(-c3cccc4oc5ccc(-c6cccc7c6c6ccccc6n7-c6ccccc6)cc5c34)n2)cc1]
EG9

TABLE 3-continued
Structural formulae of the materals for the OLEDs
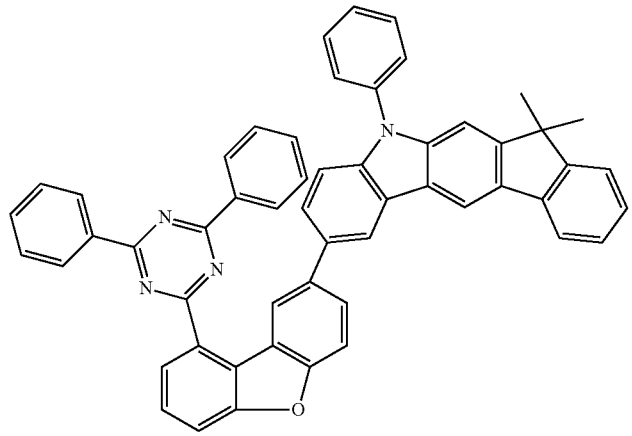 [SMILES: CC1(C)c2ccccc2-c2cc3c4cc(-c5ccc6oc7cccc(-c8nc(-c9ccccc9)nc(-c9ccccc9)n8)c7c6c5)ccc4n(-c4ccccc4)c3cc21]
EG10
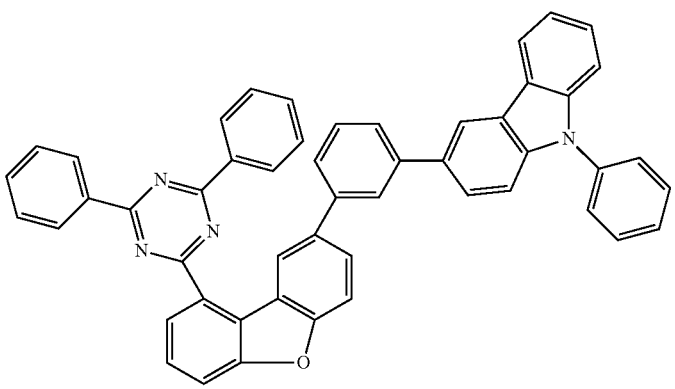 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1]
EG11
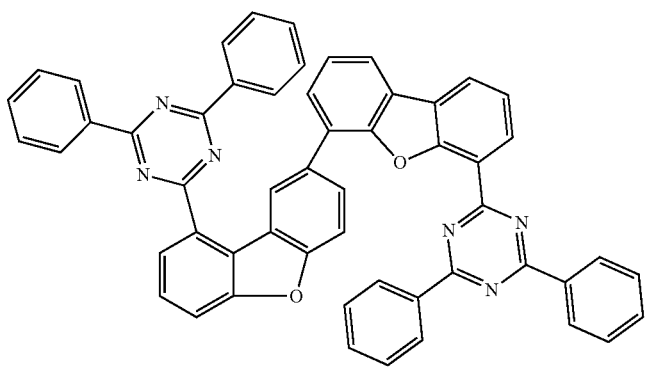 [SMILES: c1ccc(-c2nc(-c3ccccc3)nc(-c3cccc4c3oc3c(-c5ccc6oc7cccc(-c8nc(-c9ccccc9)nc(-c9ccccc9)n8)c7c6c5)cccc34)n2)cc1]
E12

TABLE 3-continued
Structural formulae of the materials for the OLEDs
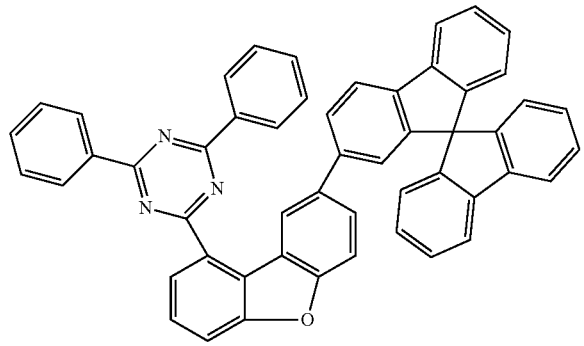 [SMILES: c1ccc(-c2nc(-c3ccccc3)nc(-c3cccc4oc5ccc(-c6ccc7c(c6)C6(c8ccccc8-c8ccccc86)c6ccccc6-7)cc5c34)n2)cc1]
EG13
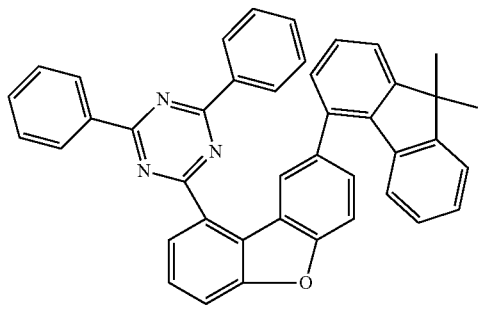 [SMILES: CC1(C)c2ccccc2-c2c(-c3ccc4oc5cccc(-c6nc(-c7ccccc7)nc(-c7ccccc7)n6)c5c4c3)cccc21]
EG14
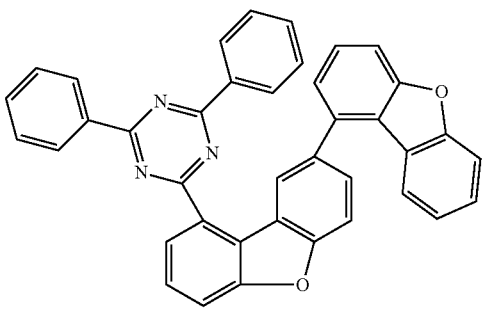 [SMILES: c1ccc(-c2nc(-c3ccccc3)nc(-c3cccc4oc5ccc(-c6cccc7oc8ccccc8c67)cc5c34)n2)cc1]
EG15
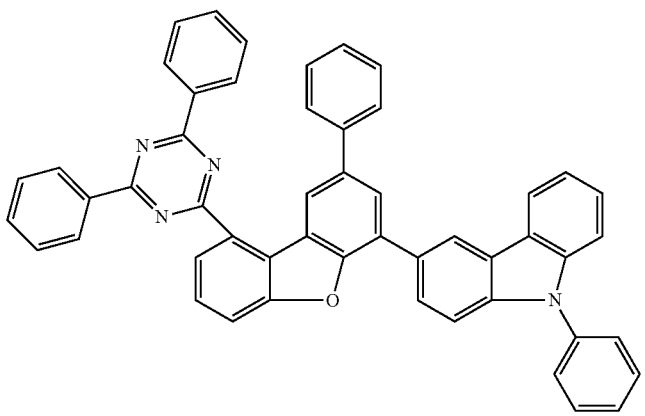 [SMILES: c1ccc(-c2cc(-c3ccc4c(c3)c3ccccc3n4-c3ccccc3)c3oc4cccc(-c5nc(-c6ccccc6)nc(-c6ccccc6)n5)c4c3c2)cc1]
EG16

TABLE 3-continued
Structural formulae of the materals for the OLEDs
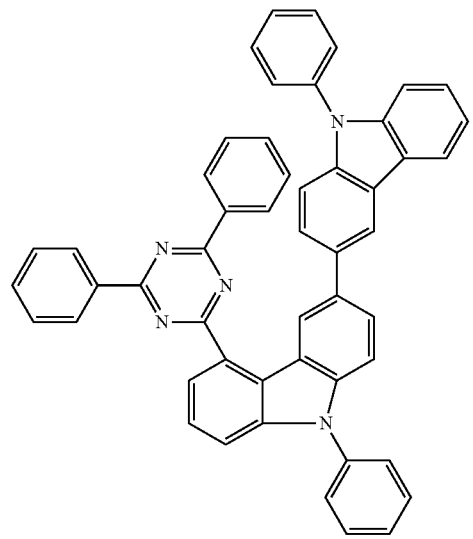 [SMILES: c1ccc(-c2nc(-c3ccccc3)nc(-c3cccc4c3c3cc(-c5ccc6c(c5)c5ccccc5n6-c5ccccc5)ccc3n4-c3ccccc3)n2)cc1]
EG17
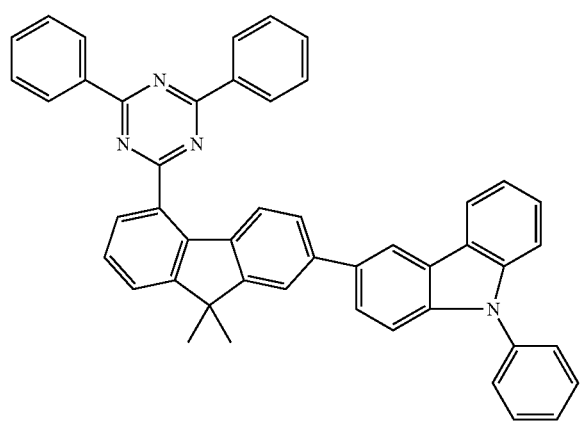 [SMILES: CC1(C)c2cc(-c3ccc4c(c3)c3ccccc3n4-c3ccccc3)ccc2-c2c(-c3nc(-c4ccccc4)nc(-c4ccccc4)n3)cccc21]
EG18
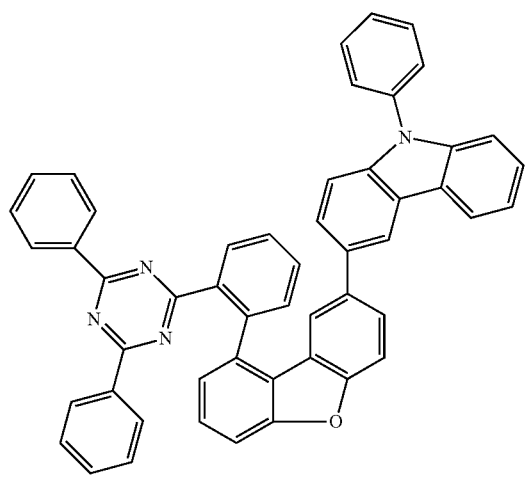 [SMILES: c1ccc(-c2nc(-c3ccccc3)nc(-c3ccccc3-c3cccc4oc5ccc(-c6ccc7c(c6)c6ccccc6n7-c6ccccc6)cc5c34)n2)cc1]
EG19

TABLE 3-continued

Structural formulae of the materials for the OLEDs

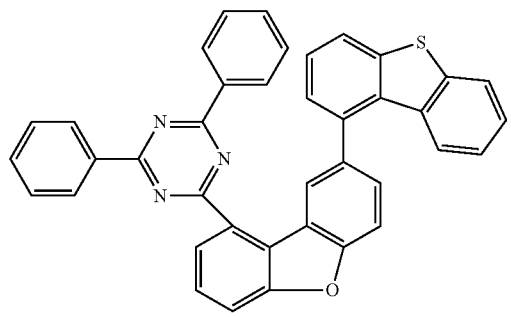 [SMILES: c1ccc(-c2nc(-c3ccccc3)nc(-c3cccc4oc5ccc(-c6cccc7sc8ccccc8c67)cc5c34)n2)cc1]

EG20

The invention claimed is:

1. An organic electroluminescent device comprising in the emissive layer a mixture of a phosphorescent emitter and a compound of the formula (1),

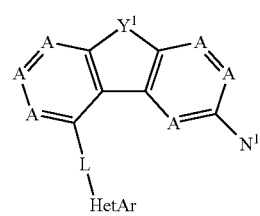

formula (1)

where the following applies to the symbols used:

A is on each occurrence, identically or differently, $CR^1$;
$Y^1$ is O or S;
L is on each occurrence, identically or differently, a single bond or an aromatic or heteroaromatic ring system having 5 to 30 aromatic ring atoms, which may be substituted by one or more radicals $R^1$;
HetAr is a group of the formula (2), (3) or (4),

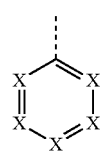

formula (2)

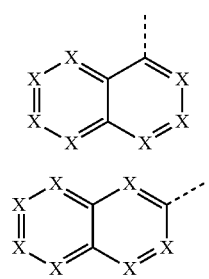

formula (3)

formula (4)

where the dashed bond represents the linking of this group;

X is on each occurrence, identically or differently, $CR^2$ or N, with the proviso that at least one symbol X stands for N;
$N^1$ is a group of formula (6),

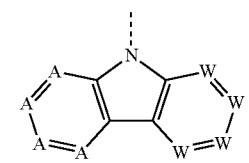

formula (6)

where the dashed bond represents the linking of this group;
precisely two adjacent groups W together stand for a group of the formula (7), and the remaining groups W stand, identically or differently on each occurrence, for $CR^1$ or N,

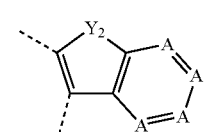

formula (7)

where the dashed bonds indicate the linking of this group;
$Y^2$ are, identically or differently on each occurrence, O, $NR^4$, S, $C(R^4)_2$, $Si(R^4)_2$, $BR^4$ or C=O, where the radical $R^4$ which is bonded to N is not equal to H for the groups of formulae (7) and (8);
$R^1$ is selected on each occurrence, identically or differently, from the group consisting of H, D, F, a straight-chain alkyl group having 1 to 20 C atoms or a branched or cyclic alkyl group having 3 to 20 C atoms, each of which may be substituted by one or more radicals $R^5$, where one or more H atoms may be replaced by D, F, or CN or, an aromatic ring system having 5 to 40 aromatic ring atoms, which may in each case be substituted by one or more radicals $R^5$;
$R^2$, $R^4$ are selected on each occurrence, identically or differently, from the group consisting of H, D, F, CN, a straight-chain alkyl group having 1 to 20 C atoms or a branched or cyclic alkyl group having 3 to 20 C atoms, each of which may be substituted by one or more radicals R⁵, where one or more H atoms may be replaced by D, F, or CN or, an aromatic or heteroaromatic ring system having 5 to 40 aromatic ring atoms, which may in each case be substituted by one or more radicals R⁵; two adjacent substituents R⁴ may form an aliphatic or aromatic ring system, which may be substituted by one or more radicals R⁵;

R⁵ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents R⁵ here may form an aliphatic ring system with one another.

2. The device according to claim 1 wherein the compound is of the formula (1a),

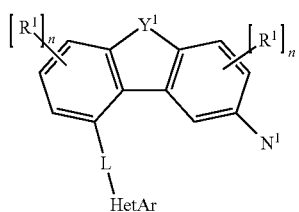

formula (1a)

where symbols used have the meanings given in claim 1 and n stands, identically or differently on each occurrence, for 0, 1, 2 or 3.

3. The device according to claim 1 of one of the formulae (1b) to (1g),

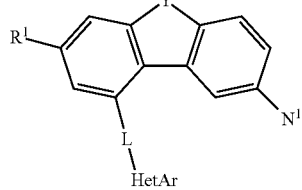

formula (1b)

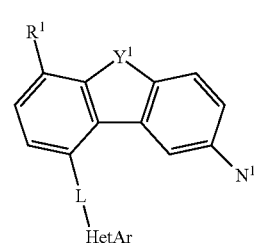

formula (1c)

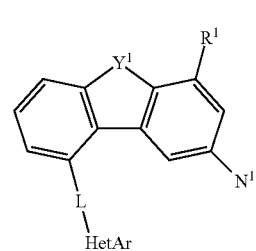

formula (1d)

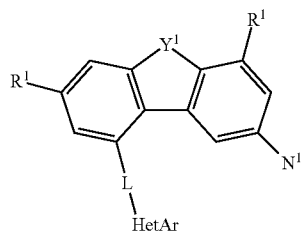

formula (1e)

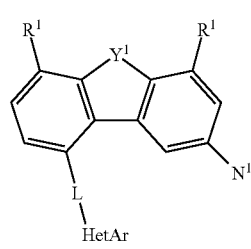

formula (1f)

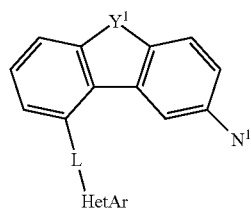

formula (1g)

where the symbols used have the meanings given in claim 1.

4. The device according to claim 1, wherein the groups of the formulae (2), (3) and (4) are selected from the groups of the formulae (2-1) to (2-10), (3-1) and (4-1),

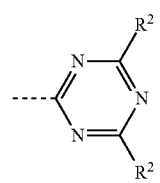

formula (2-1)

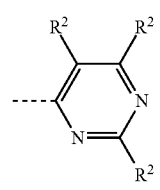

formula (2-2)

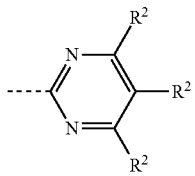

formula (2-3)

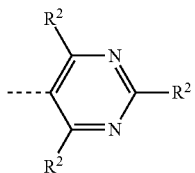

formula (2-4)

-continued

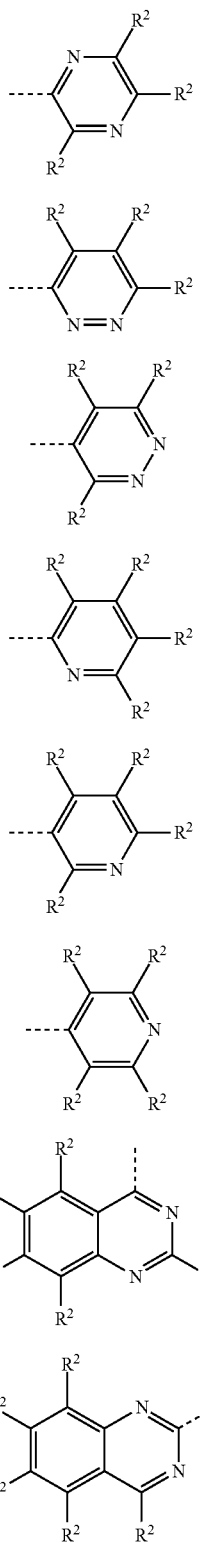

formula (2-5)

formula (2-6)

formula (2-7)

formula (2-8)

formula (2-9)

formula (2-10)

formula (3-1)

formula (4-1)

where the dashed bond represents the linking of these groups and $R^2$ has the meanings claim 1.

5. The device according to claim 1, wherein the group of the formula (6) is selected from the groups of the formula (6-2),

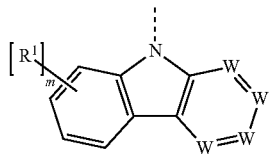

formula (6-2)

where $R^1$ has the meanings given in claim 1 and wherein two adjacent groups W together stand for a group of the formula (7a) and the other two groups W stand for $CR^1$,

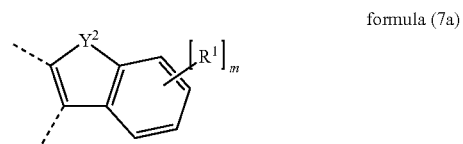

formula (7a)

where $Y^2$ and $R^1$ have the meanings given in claim 1;

m is, identically or differently on each occurrence, 0, 1, 2, 3 or 4.

6. The device according to claim 1, wherein the group of the formula (6) is selected from the groups of the formulae (6-2a) to (6-2f),

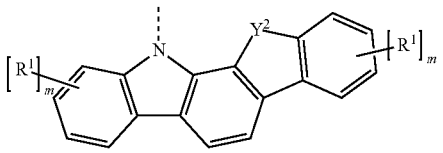

Formel (6-2a)

Formel (6-2b)

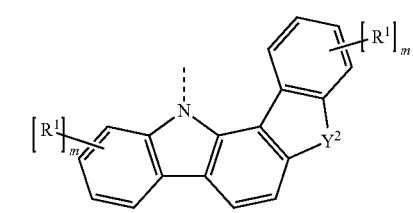

Formel (6-2c)

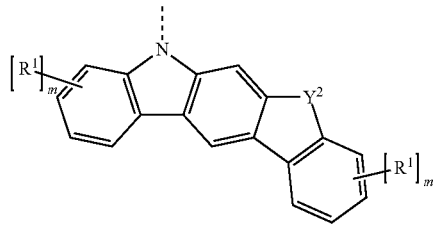

Formel (6-2d)

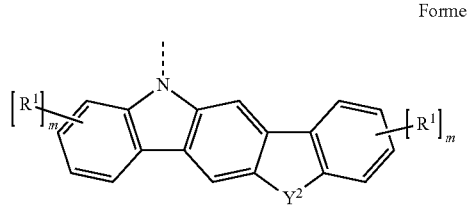

-continued

Formel (6-2e)

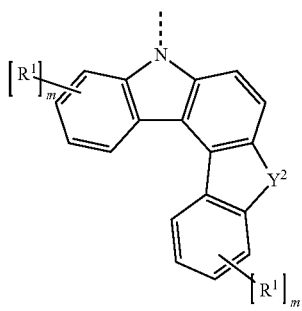

Formel (6-2f)

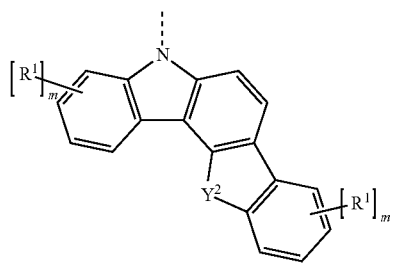

where the symbols and indices used have the meanings given in claim 1;

m is, identically or differently on each occurrence, 0, 1, 2, 3 or 4.

7. The device according to claim 1, wherein $Y^2$ stand, identically or differently on each occurrence, for O, $C(R^4)_2$ or $NR^4$, where the radical $R^4$ which is bonded to the nitrogen is not equal to H.

8. The device according to claim 2 wherein the compound is of the formula (1a), where the symbols used have the meanings given in claim 1 and n stands, identically or differently on each occurrence, for 0, 1, 2 or 3, and wherein $N^1$ is selected from the groups of the formula (6-2), formula (6-2)

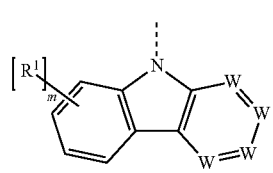

where $R^1$ has the meanings given in claim 1 and wherein two adjacent groups W together stand for a group of the formula (7a) and the other two groups W stand for $CR^1$, formula (7a)

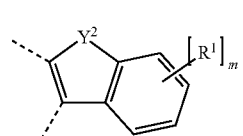

where $Y^2$ and $R^1$ have the meanings given in claim 1;
m is, identically or differently on each occurrence, 0, 1, 2, 3 or 4.

9. A compound of formula (1), formula (1)

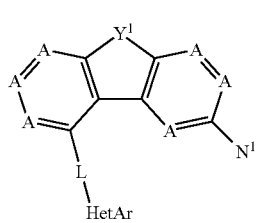

where the following applies to the symbols used:

A is on each occurrence, identically or differently, $CR^1$;

$Y^1$ is O or S;

L is on each occurrence, identically or differently, a single bond or an aromatic or heteroaromatic ring system having 5 to 30 aromatic ring atoms, which may be substituted by one or more radicals $R^1$;

HetAr is a group of the formula (2), (3) or (4), formula (2)

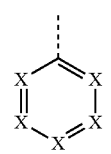

formula (3)

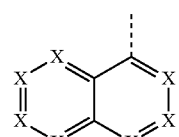

formula (4)

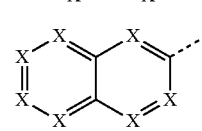

where the dashed bond represents the linking of this group;

X is on each occurrence, identically or differently, $CR^2$ or N, with the proviso that at least one symbol X stands for N;

$N^1$ is a group of formula (6), formula (6)

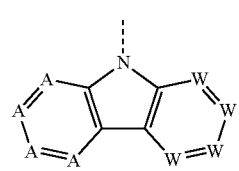

where the dashed bond represents the linking of this group;

precisely two adjacent groups W together stand for a group of the formula (7), and the remaining groups W stand, identically or differently on each occurrence, for $CR^1$ or N,

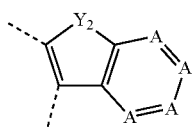

formula (7)

where the dashed bonds indicate the linking of this group;

$Y^2$ are, identically or differently on each occurrence, O, $NR^4$, S, $C(R^4)_2$, $Si(R^4)_2$, $BR^4$ or C=O, where the radical $R^4$ which is bonded to N is not equal to H for the groups of formulae (7) and (8);

$R^1$ is selected on each occurrence, identically or differently, from the group consisting of H, D, F, CN, a straight-chain alkyl group having 1 to 20 C atoms or a branched or cyclic alkyl group having 3 to 20 C atoms, each of which may be substituted by one or more radicals $R^5$, where one or more H atoms may be replaced by D, F, or CN or, an aromatic ring system having 5 to 40 aromatic ring atoms, which may in each case be substituted by one or more radicals $R^5$;

$R^2$, $R^4$ are selected on each occurrence, identically or differently, from the group consisting of H, D, F, CN, a straight-chain alkyl group having 1 to 20 C atoms or a branched or cyclic alkyl group having 3 to 20 C atoms, each of which may be substituted by one or more radicals $R^5$, where one or more H atoms may be replaced by D, F, or CN or, an aromatic or heteroaromatic ring system having 5 to 40 aromatic ring atoms, which may in each case be substituted by one or more radicals $R^5$, two adjacent substituents $R^4$ may form an aliphatic or aromatic ring system, which may be substituted by one or more radicals $R^5$;

$R^5$ is selected on each occurrence, identically or differently, from the group consisting of H, D, F, CN, an aliphatic hydrocarbon radical having 1 to 20 C atoms or an aromatic or heteroaromatic ring system having 5 to 30 aromatic ring atoms, in which one or more H atoms may be replaced by D, F, Cl, Br, I or CN and which may be substituted by one or more alkyl groups, each having 1 to 4 carbon atoms; two or more adjacent substituents $R^5$ here may form an aliphatic ring system with one another.

* * * * *